US011434229B2

(12) United States Patent
Wong et al.

(10) Patent No.: US 11,434,229 B2
(45) Date of Patent: Sep. 6, 2022

(54) 4,9-DIOXO-4,9-DIHYDRONAPHTHO[2,3-B]FURAN-3-CARBOXAMIDE DERIVATIVES AND USES THEREOF FOR TREATING PROLIFERATIVE DISEASES AND INFECTIOUS DISEASES

(71) Applicants: Academia Sinica, Taipei (TW); National Taiwan University, Taipei (TW)

(72) Inventors: Chi-Huey Wong, Rancho Santa Fe, CA (US); Pan-Chyr Yang, Taipei (TW); Rong-Jie Chein, Taipei (TW); Szu-Hua Pan, Taipei (TW); Ting-Jen R. Cheng, New Taipei (TW)

(73) Assignees: Academia Sinica, Taipei (TW); National Taiwan UJniversity, Taipei (TW)

( * ) Notice: Subject to any disclaimer, the term of this patent is extended or adjusted under 35 U.S.C. 154(b) by 0 days.

(21) Appl. No.: 16/081,490

(22) PCT Filed: Feb. 28, 2017

(86) PCT No.: PCT/US2017/019964
§ 371 (c)(1),
(2) Date: Aug. 31, 2018

(87) PCT Pub. No.: WO2017/151625
PCT Pub. Date: Sep. 8, 2017

(65) Prior Publication Data
US 2020/0095233 A1    Mar. 26, 2020

Related U.S. Application Data

(60) Provisional application No. 62/301,717, filed on Mar. 1, 2016.

(51) Int. Cl.
*C07D 405/12*    (2006.01)
*C07D 307/92*    (2006.01)
(Continued)

(52) U.S. Cl.
CPC ......... *C07D 405/12* (2013.01); *C07D 307/92* (2013.01); *C07D 403/12* (2013.01); *C07D 413/12* (2013.01)

(58) Field of Classification Search
CPC ... C07D 413/12; C07D 405/12; C07D 403/12
See application file for complete search history.

(56) References Cited

U.S. PATENT DOCUMENTS 5,663,197 A      9/1997   Ueda et al.
8,877,803 B2 *  11/2014   Jiang ..................... A61P 43/00
                                                            514/468

FOREIGN PATENT DOCUMENTS

CN          1086815 A        5/1994
CN        101854937 A       10/2010
(Continued)

OTHER PUBLICATIONS

Vukomanovic et al. (Medical Gas Research 2014 4:4).*
(Continued)

*Primary Examiner* — Valerie Rodriguez-Garcia
(74) *Attorney, Agent, or Firm* — Huan-Yi Lin

(57) ABSTRACT

The present disclosure provides compounds of Formulas (I), (II), and pharmaceutically acceptable salts thereof. The compounds described herein are useful in treating proliferative diseases, for example, cancer (e.g., lung cancer), and infectious diseases (e.g., bacterial infections).

(Continued)

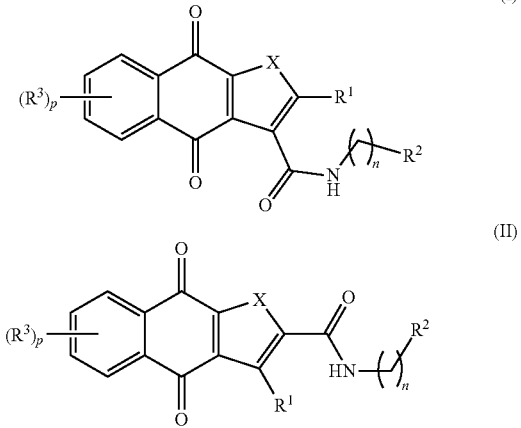

3 Claims, 12 Drawing Sheets

(51) Int. Cl.
*C07D 403/12* (2006.01)
*C07D 413/12* (2006.01)

(56) References Cited

FOREIGN PATENT DOCUMENTS

| WO | WO 2009/036059 A2 | 3/2009 |
|---|---|---|
| WO | 2015120304 A1 | 8/2015 |
| WO | WO 2015/120304 A1 | 8/2015 |

OTHER PUBLICATIONS

Wermuth, C.G. (The Practice of Medicinal Chemistry. Chapter 13 Molecular Variations Based on Isoteric Replacements. Academic Press, 2003. "A. Fluorine-hydrogen isosterism"; p. 226-228).*
Patani (Chem. Rev. 1996, 96, 3147-3176).*
Wikipedia "Bioisostere" (https://en.wikipedia.org/wiki/Bioisostere—available online as of Sep. 27, 2015).*
Lindenschmidt et al. (European Journal of Medicinal Chemistry 110 (2016) p. 280-290).*
Dennery et al. (J. Clin. Invest. vol. 101, No. 5, 1998,p. 1001-1011).*
Chemical Abstract Compound, STN express. RN 879919-29-6 (Apr. 10, 2006), RN 879783-11-6 (Apr. 9, 2006),RN 879783-07-0 (Apr. 9, 2006), RN 867135-83-9 (Nov. 9, 2005), RN 867135-82-8 (Nov. 9, 2005), RN 867135-78-2 (Nov. 9, 2005), RN 867135-77-1 (Nov. 9, 2005), RN 690641-02-2 (Jun. 8, 2004), RN 690641-01-1 (Jun. 8, 2004), RN 690641-00-0 (Jun. 8, 2004), RN 690640-99-4 (Jun. 8, 2004), RN 690640-96-1 (Jun. 8, 2004), RN 690640-95-0 (Jun. 8, 2004), RN 690640-91-6 (Jun. 8, 2004), RN 631856-25-2 (Dec. 29, 2003).
Chemical Abstract Compound, STN express. RN 690641-03-3 (Jun. 8, 2004).
Guo et al., Mn(II)-catalyzed synthesis of benzo[f]indole-4,9-diones via vinyl azides and 2-hydroxynaphthoquinone. Tetrahedron. 2015;71:9371-9375.
Lindenschmidt et al., 8-Halo-substituted naphtho[2,3-b]thiophene-4,9-diones as redox-active inhibitors of keratinocyte hyperproliferation with reduced membrane-damaging properties. Eur J Med Chem. Mar. 3, 2016;110:280-90. doi: 10.1016/j.ejmech.2016.01.040. Epub Jan. 23, 2016.
Vukomanovic et al., In vitro Activation of heme oxygenase-2 by menadione and its analogs. Med Gas Res. Feb. 18, 2014;4(1):4. doi: 10.1186/2045-9912-4-4.
Chemical Abstract Compound, STN "RN:883247-26-5; 879919-29-6; 879783-11-6; 879783-07-0; 867135-83-9; 867135-82-8; 867135-77-1; 690641-00-0; 690640-99-4; 690640-96-1; 631856-25-2; 867135-78-2; 867135-76-0; 390641-03-3; 690641-02-2; 690641-01-1; 690640-95-06; 90640-94-9; 690640-93-8; 690640-91-6" published on May 8, 2006.
Medical Gas Research, Dragic Vukomanovic et al., "In vitro Activation of heme oxygenase-2 by menadione and its analogs" published on Dec. 31, 2014.
Tetrahedron, Guo Shanshan, "Mn(II)-catalyzed synthesis of benzo[f]indole-4, 9-diones via vinyl azides and 2-hydroxynaphthoquinone" published on Aug. 28, 2015.
European Journal of Medicinal Chemistry, Lindenschmidt Cathrin, "8-Halo-substituted naphtho[2,3-b]thiophene-4,9-diones as redox-active inhibitors of keratinocyte hyperproliferation with reduced membrane-damaging properties" published on Jan. 23, 2016.
Antimicrobial Agents and Chemotherapy, Kumiko Nagata, "Antimicrobial Activity of Novel Furanonaphthoquinone Analogs" pbulished on Dec. 31, 1998.
Org. Biomol Chem., Zong-Ze Wu, "A versatile and practical method for regioselective synthesis of polysubstituted furanonaphthoquinones" pulbished on Nov. 22, 2012.
Office Action of China counterpart application dated Nov. 17, 2021.

* cited by examiner

D

E

A

B

C

F

G

4,9-DIOXO-4,9-DIHYDRONAPHTHO[2,3-B]FURAN-3-CARBOXAMIDE DERIVATIVES AND USES THEREOF FOR TREATING PROLIFERATIVE DISEASES AND INFECTIOUS DISEASES

RELATED APPLICATIONS

This Application is a national stage filing under 35 U.S.C. 371 of International Patent Application Serial No. PCT/US2017/019964, filed Feb. 28, 2017, entitled "4,9-DIOXO-4,9-DIHYDRONAPHTHO[2,3-B]FURAN-3-CARBOXAMIDE DERIVATIVES AND USES THEREOF FOR TREATING PROLIFERATIVE DISEASES AND INFECTIOUS DISEASES," which claims priority under 35 U.S.C. § 119(e) to U.S. Provisional Application, U.S. Ser. No. 62/301,717 filed Mar. 1, 2016, the entire contents of each which is incorporated by reference herein.

RELATED APPLICATIONS

This application claims priority under 35 U.S.C. § 119(e) to U.S. Provisional Application, U.S. Ser. No. 62/301,717, filed Mar. 1, 2016, which is incorporated herein by reference.

BACKGROUND OF THE INVENTION

Lung cancer is the leading cause of cancer-related death worldwide. Despite advances in treatment, approximately 1.8 million patients are diagnosed with lung cancer each year in the world. Torre et al, Global cancer statistics, 2012., *CA Cancer J. Clin.*, 2015; 65: 87-108. Most of these lung cancer cases are of the non-small cell lung cancer (NSCLC) subtype. While advances in treatment have been made over the last 20 years, the response rate of lung cancer patients to chemotherapy is less than 30%, and the prognosis remains poor. Nguyen et al, (2009), *Clinical Lung Cancer*, 10(4): 281-289; and Nguyen et al, (2012), *Biologics*: targets & therapy 6:337-345. Although the development of specific tyrosine kinase inhibitors (TKIs) that target the epithelial growth factor receptor (EGFR) has significantly improved the treatment of lung cancer patients with an active EGFR mutation, resistance usually develops within a year after treatment. To circumvent this problem, developing new anti-cancer drugs for lung cancer patients, especially for those without a favorable response to EGFR-TKI, such as patients with the EGFR wild-type sequence, EGFR T790M or a c-Met amplification, is of current interest in lung cancer studies.

Uncontrolled proliferation is a significant characteristic of cancer cells. Therefore, DNA replication has traditionally been an important target for cancer therapy. For example, minichromosome maintenance (MCM) eukaryotic replicative helicase, an important component of the DNA replication system that ensures only one round of DNA replication per cell cycle. is a potential therapeutic target. Kubota et al, *Cell*, 81(4):601-609; hong et al, *Nature*, 375(6530):418-421; and Romagnoli, et al, *Am. J. Pathol.*, 174(3): 762-770. MCM replicative helicase is a hetero-hexameric complex formed by six subunits, numbered MCM2 through MCM7. It is a key target for loading and is strictly controlled during replication initiation Ishimi, et al., (2003), *Eur. J. Biochem.*, 270(6):1089-1101; and Bell et al, *Ann. Rev. Biochem.*, 71:333-374. Previous studies have shown that several proteins involved in the replication initiation, including Cdt1, Cdc6, and MCM2-7, are highly expressed in many types of cancers. Ishimi et al., 2003; Giaginis, et al. (2009), *Dig. Dis. Sci.*, 54(2): 282-291; Madine et al, *Nature*, 375(6530): 421-424; and Kikuchi, et al, (2011), *Lung Cancer*, 72(2): 229-237. Among them, MCM2-7 overexpression was significantly correlated with the malignant progression of cancer and could be used to predict poor prognosis in patients. Romagholi et al.; Bravou, et al, *Int. J. Oncol.*, 27(6):1511-1518; Williams, et al, *Proc. Natl. Acad. Sci. USA*, 95(25): 14932-14937; and Marnerides, et al, *Anticancer Res.*, 31(10):3585-3594. The report that both specific mutations in MCM2/5 cause different DNA binding at the MCM2/5 active site with putative regulatory significance indicated the importance of MCM2 regulation in DNA replication. Kikuchi et al., 2011. MCM2 is also a predictor of survival in patients with NSCLC. Giaginis et al., 2009; Kikuchi et al., 2011; Yang, et al, (2006), *BMC Cancer*, 6:203; and Yang, et al, *Oncol. Rep.*, 27(1):135-142. There is therefore a need to develop new agents that target MCM2 as potential therapeutic candidate for treating diseases associated with MCM2, for example, cancer.

SUMMARY OF THE INVENTION

The present disclosure provides compounds, such as compounds of Formulas (I) and (II) that inhibit MCM, for example, MCM2. The compounds described herein may be useful in treating diseases associated with MCM (e.g., any one of MCM2-MCM7), for example, proliferative diseases such as cancer (e.g., lung cancer, breast cancer, leukemia, lymphoma, melanoma, multiple myeloma, Ewing's sarcoma, osteosarcoma, brain cancer, neuroblastoma). The compounds described herein may also be useful in treating infectious diseases, such as bacterial infections, and useful in alleviating inflammatory conditions. Also provided are pharmaceutical compositions, kits, methods, and uses of any of the compounds described herein.

In one aspect, the present disclosure provides compounds of Formula (I) and Formula (II):

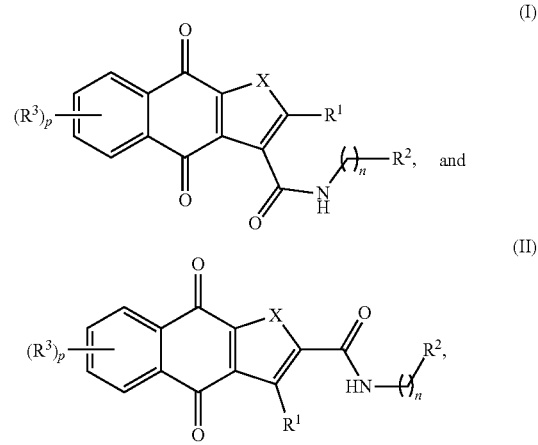

or pharmaceutically acceptable salts, wherein n is 1, 2, 3, 4, or 5; p is 1, 2, 3, or 4; and X is independently —O—, —S—, or —NR$^X$—. In addition, R$^X$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

$R^1$ is hydrogen, halogen, —CN, —NO$_2$, —N$_3$, optionally substituted alkyl, optionally substituted alkenyl, optionally substituted alkynyl, optionally substituted carbocyclyl, optionally substituted aryl, optionally substituted heterocyclyl, or optionally substituted heteroaryl;

$R^2$ is hydrogen, optionally substituted alkyl, optionally substituted alkenyl, optionally substituted alkynyl, optionally substituted carbocyclyl, optionally substituted aryl, optionally substituted heterocyclyl, or optionally substituted heteroaryl;

each instance of $R^3$ is independently hydrogen, halogen, —CN, —NO$_2$, —N$_3$, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^A$, —N(R$^B$)$_2$, —C(=O)R$^A$, or —SO$_2$R$^A$;

each instance of $R^A$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group; and each instance of $R^B$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two $R^B$ are taken together with the intervening nitrogen to form optionally substituted heterocyclyl or optionally substituted heteroaryl.

In certain embodiments, a compound of Formula (I) is of Formula (I-A):

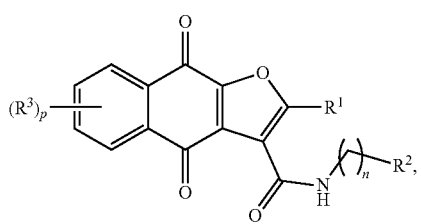

(I-A)

or a pharmaceutically acceptable salt, wherein $R^1$, $R^2$, $R^3$, n, and p are as described herein.

In certain embodiments, a compound of Formula (II) is of Formula (II-A):

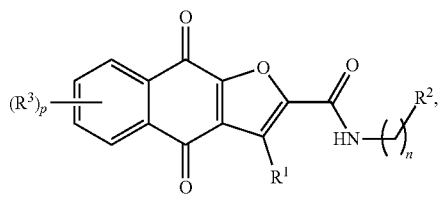

(II-A)

or a pharmaceutically acceptable salt, wherein $R^1$, $R^2$, $R^3$, n, and p are as described herein.

In certain embodiments, a compound of Formula (I) is of Formula (I-B):

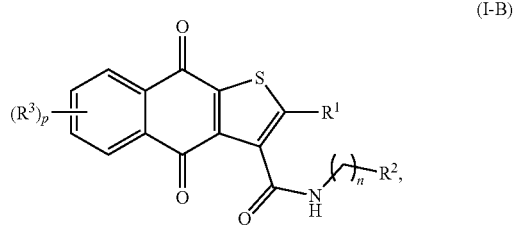

(I-B)

or a pharmaceutically acceptable salt, wherein $R^1$, $R^2$, $R^3$, n, and p are as described herein.

In certain embodiments, a compound of Formula (II) is of Formula (II-B):

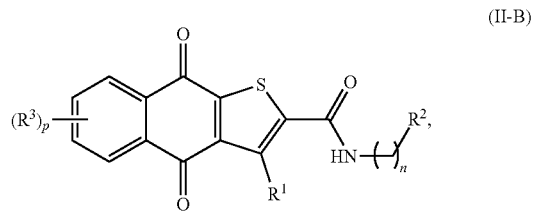

(II-B)

or a pharmaceutically acceptable salt, wherein $R^1$, $R^2$, $R^3$, n, and p are as described herein.

In certain embodiments, a compound of Formula (I) is of Formula (I-C):

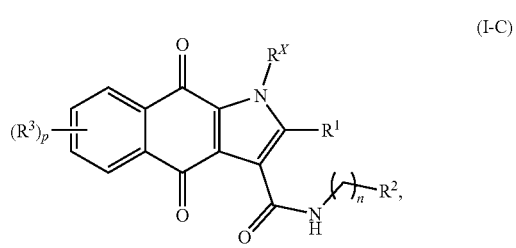

(I-C)

or a pharmaceutically acceptable salt, wherein $R^1$, $R^2$, $R^3$, $R^X$, n, and p are as described herein.

In certain embodiments, a compound of Formula (II) is of Formula (II-C):

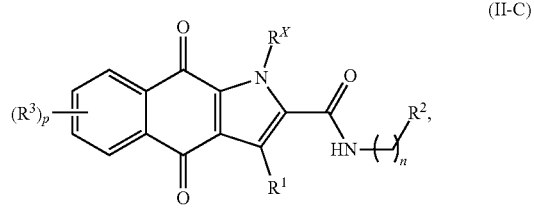

(II-C)

or a pharmaceutically acceptable salt, wherein $R^1$, $R^2$, $R^3$, $R^X$, n, and p are as described herein.

Exemplary compounds of Formula (I) include, but are not limited to:

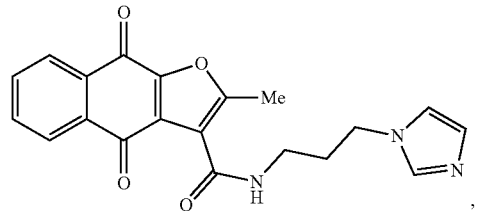

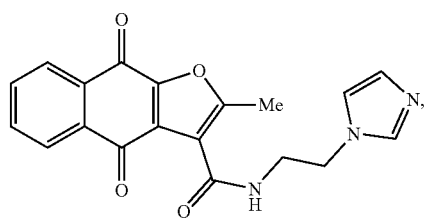

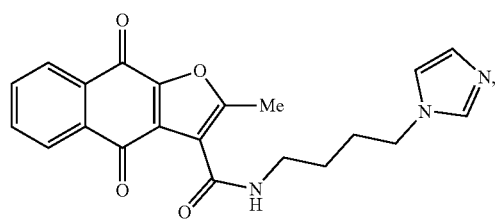

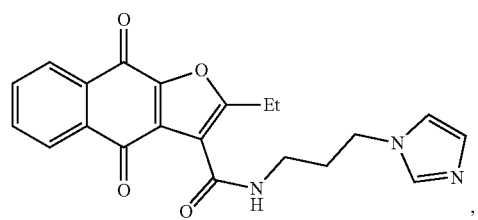

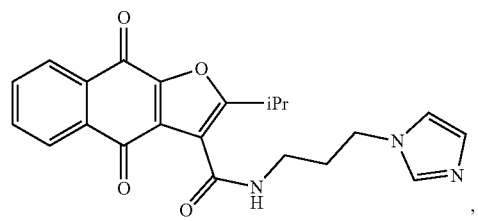

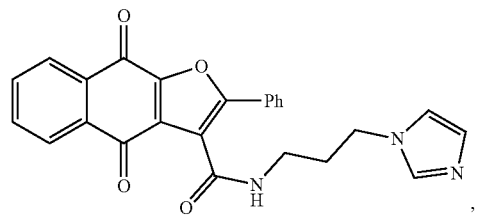

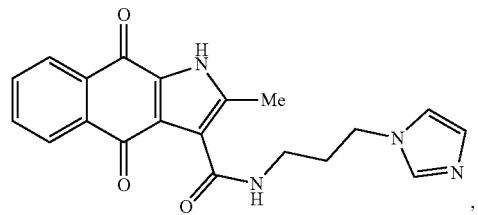

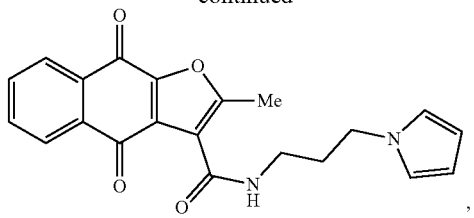

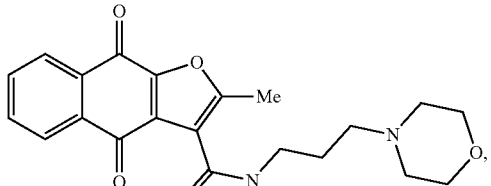

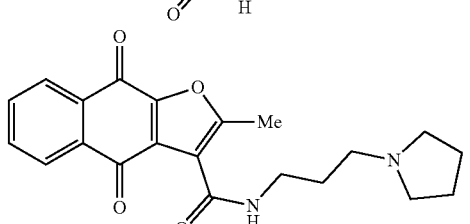

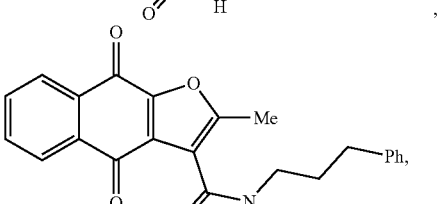

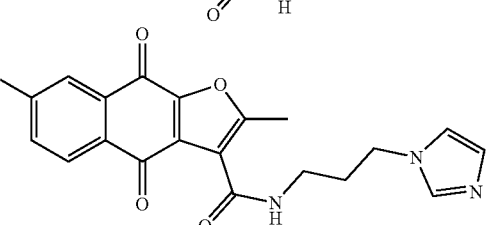

or pharmaceutically acceptable salts.

Exemplary compounds of Formula (II) include, but are not limited to:

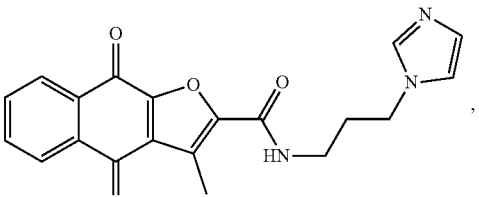

or pharmaceutically acceptable salts.

In another aspect, the present disclosure provides pharmaceutical compositions including one or more of the compounds described herein, and a pharmaceutically acceptable excipient. In certain embodiments, the pharmaceutical compositions described herein include an effective amount of a compound described herein for inhibiting one or more MCM protein helicases, such as one or more of MCM2-MCM7. An effective amount described herein may be a therapeutically effective amount or prophylactically effective amount.

In yet another aspect, the present disclosure provides methods for treating a proliferative disease (e.g., cancer) or infectious disease (e.g., bacterial infection), the method comprising administering to a subject in need of the treatment an effective amount of any of the pharmaceutical compositions described herein.

In certain embodiments, a target proliferative disease can be cancer, including, but not limited to lung cancer (e.g., bronchogenic carcinoma, small cell lung cancer (SCLC), non-small cell lung cancer (NSCLC), adenocarcinoma of the lung), acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenström's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM), a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

In preferred embodiments, the cancer is lung cancer (e.g., bronchogenic carcinoma, small cell lung cancer (SCLC), non-small cell lung cancer (NSCLC), adenocarcinoma of the lung), breast cancer (e.g., adenocarcinoma of the breast, papillary carcinoma of the breast, mammary cancer, medullary carcinoma of the breast), colorectal cancer (e.g., colon cancer, rectal cancer, colorectal adenocarcinoma), pancreatic cancer pancreatic cancer (e.g., pancreatic andenocarcinoma, intraductal papillary mucinous neoplasm (IPMN), islet cell tumors), gastric cancer (e.g., stomach adenocarcinoma), or cervical cancer (e.g., cervical adenocarcinoma).

In certain embodiments, a target infectious disease can be bacterial infection such as *Staphylococcus* infection, *Streptococcus* infection, *Enterococcus* infection, and gram negative bacterial infection.

In certain embodiments, the subject being treated is a mammal (e.g., human or non-human mammal).

Another aspect of the present disclosure relates to kits comprising a container with a compound, or pharmaceutical composition thereof, as described herein. The kits described herein may include a single dose or multiple doses of the compound or pharmaceutical composition. The kits may be useful in a method of the disclosure. In certain embodiments, the kit further includes instructions for using the compound or pharmaceutical composition. The kit may also optionally include a device for administration of the compound or composition (e.g., a syringe such as a pre-filled syringe for parenteral administration).

In yet another aspect, the present disclosure provides compounds and pharmaceutical compositions described herein for use in treating a disease such as cancer or bacterial infection as described herein and/or for manufacturing a medicament for use in treating the target disease.

The details of one or more embodiments of the disclosure are set forth herein. Other features, objects, and advantages of the disclosure will be apparent from the Detailed Description, the Examples, and the Claims.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$). In certain embodiments, the alkyl group is a substituted $C_{1-10}$ alkyl (such as substituted $C_{1-6}$ alkyl, e.g., —$CF_3$).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=CHCH$_3$ or

)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thioca-nyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups). Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups, are further referred to using the suffix -ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O) R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$) OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$) R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$) R$^{ee}$, —OC(=NR$^{ff}$)OR$^{ee}$, —C(=NR$^{ff}$)N(R$^{ff}$)$_2$, —OC (=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, P(=O) (OR$^{ee}$)$_2$, —P(=O)(R$^{ee}$)$_2$, —OP(=O)(R$^{ee}$)$_2$, —OP(=O) (OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH (OH), —SH, —SC$_{1-6}$ alkyl, —SS(C$_{1-6}$ alkyl), —C(=O) (C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N (C$_{1-6}$ alkyl)$_2$, —OC(=O)NH(C$_{1-6}$ alkyl), —NHC(=O) (C$_{1-6}$ alkyl), —N(C$_{1-6}$ alkyl)C(=O)(C$_{1-6}$ alkyl), —NHCO$_2$ (C$_{1-6}$ alkyl), —NHC(=O)N(C$_{1-6}$ alkyl)$_2$, —NHC(=O)NH (C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC (NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N (C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S (C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O) (C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH (OH), —SH, —SC$_{1-6}$ alkyl, —SS(C$_{1-6}$ alkyl), —C(=O) (C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N (C$_{1-6}$ alkyl)$_2$, —OC(=O)NH(C$_{1-6}$ alkyl), —NHC(=O) (C$_{1-6}$ alkyl), —N(C$_{1-6}$ alkyl)C(=O)(C$_{1-6}$ alkyl), —NHCO$_2$ (C$_{1-6}$ alkyl), —NHC(=O)N(C$_{1-6}$ alkyl)$_2$, —NHC(=O)NH (C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH) NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C (=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S) SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, F$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5-(CF$_3$)$_2$C$_6$H$_3$]$_4^-$, BPh$_4^-$, Al(OC(CF$_3$)$_3$)$_4^-$, and a carborane anion (e.g., CB$_{11}$H$_{12}^-$ or (HCB$_{11}$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethylcarbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). Exemplary oxygen atom substituents include, but are not limited to, —R$^{aa}$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$ and R$^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

Exemplary sulfur atom substituents include, but are not limited to, $-R^{aa}$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3{}^+X^-$, $-P(OR^{cc})_2$, $-P(OR^{cc})_3{}^+X^-$, $-P(=O)(R^{aa})_2$, $-P(=O)(OR^{cc})_2$, and $-P(=O)(N(R^{bb})_2)_2$, wherein $R^{aa}$, $R^{bb}$, and $R^{cc}$ are as defined herein.

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms" or "carbon units") and does not include hydrogen atoms or heteroatoms. However, a non-chain substituent of a hydrocarbon chain may include any atoms, including hydrogen atoms, carbon atoms, and heteroatoms. For example, hydrocarbon chain $-C^AH(C^BH_2C^CH_3)-$ includes one chain atom $C^A$, one hydrogen atom on $C^A$, and non-chain substituent $-(C^BH_2C^CH_3)$. The term "$C_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, $-CH(C_2H_5)-$ is a $C_1$ hydrocarbon chain, and

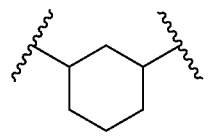 [SMILES: *C1CCCC(*)C1]

is a $C_3$ hydrocarbon chain. When a range of values is used, the meaning of the range is as described herein. For example, a $C_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., $-(CH_2)_4-$). A hydrocarbon chain may also be unsaturated and include one or more C=C and/or C≡C bonds anywhere in the hydrocarbon chain. For instance, $-CH=CH-(CH_2)_2-$, $-CH_2-C≡C-CH_2-$, and $-C≡C-CH=CH-$ are all examples of a unsubstituted and unsaturated hydrocarbon chain. In certain embodiments, the hydrocarbon chain is unsubstituted (e.g., $-C≡C-$ or $-(CH_2)_4-$). In certain embodiments, the hydrocarbon chain is substituted (e.g., $-CH(C_2H_5)-$ and $-CF_2-$). Any two substituents on the hydrocarbon chain may be joined to form an optionally substituted carbocyclyl, optionally substituted heterocyclyl, optionally substituted aryl, or optionally substituted heteroaryl ring. For instance,

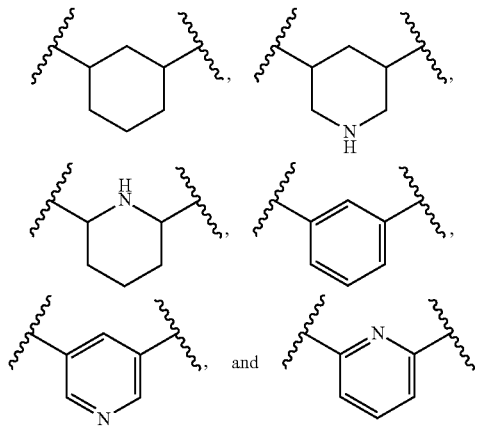

are all examples of a hydrocarbon chain. In contrast, in certain embodiments,

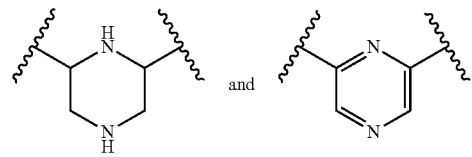 [SMILES: *C1CNCC(*)N1 ; "and" ; *c1cncc(*)n1]

are not within the scope of the hydrocarbon chains described herein. When a chain atom of a $C_x$ hydrocarbon chain is replaced with a heteroatom, the resulting group is referred to as a $C_x$ hydrocarbon chain wherein a chain atom is replaced with a heteroatom, as opposed to a $C_{x-1}$ hydrocarbon chain. For example,

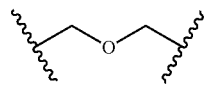

is a $C_3$ hydrocarbon chain wherein one chain atom is replaced with an oxygen atom. The term "leaving group" is given its ordinary meaning in the art of synthetic organic chemistry and refers to an atom or a group capable of being displaced by a nucleophile. See, for example, Smith, *March Advanced Organic Chemistry* 6th ed. (501-502). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is an activated substituted hydroxyl group (e.g., $-OC(=O)SR^{aa}$, $-OC(=O)R^{aa}$, $-OCO_2R^{aa}$, $-OC(=O)N(R^{bb})_2$, $-OC(=NR^{bb})R^{aa}$, $-OC(=NR^{bb})OR^{aa}$, $-OC(=NR^{bb})N(R^{bb})_2$, $-OS(=O)R^{aa}$, $-OSO_2R^{aa}$, $-OP(R^{cc})_2$, $-OP(R^{cc})_3$, $-OP(=O)_2R^{aa}$, $-OP(=O)(R^{aa})_2$, $-OP(=O)(OR^{cc})_2$, $-OP(=O)_2N(R^{bb})_2$, and $-OP(=O)(NR^{bb})_2$, wherein $R^{aa}$, $R^{bb}$, and $R^{cc}$ are as defined herein). In some cases, the leaving group is a sulfonic acid ester, such as toluenesulfonate (tosylate, —OTs), methanesulfonate (mesylate, —OMs), p-bromobenzenesulfonyloxy (brosylate, —OBs), —OS(=O)$_2$(CF$_2$)$_3$CF$_3$ (nonaflate, —ONf), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference for the subject matter and purpose referenced herein. Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$ alkyl)$_4$$^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.x H$_2$O, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5H$_2$O)), and polyhydrates (x is a number greater than 1, e.g., dihydrates (R.2H$_2$O) and hexahydrates (R.6H$_2$O)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy) alkyl esters or ((alkoxycarbonyl) oxy) alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The term "inhibition", "inhibiting", "inhibit," or "inhibitor" refer to the ability of a compound to reduce, slow, halt or prevent activity of a particular biological process in a cell relative to vehicle.

When a compound, pharmaceutical composition, method, use, or kit is referred to as "selectively," "specifically," or "competitively" binding a first protein, the compound binds the first protein with a higher binding affinity (e.g., not less than about 2-fold, not less than about 5-fold, not less than about 10-fold, not less than about 30-fold, not less than about 100-fold, not less than about 1,000-fold, or not less than about 10,000-fold) than binding a second protein or that is different from the first protein. When a compound is referred to as "selectively," "specifically," or "competitively" modulating (e.g., increasing or inhibiting) the activity of a protein, the compound modulates the activity of the protein to a greater extent (e.g., not less than about 2-fold, not less than about 5-fold, not less than about 10-fold, not less than about 30-fold, not less than about 100-fold, not less than about 1,000-fold, or not less than about 10,000-fold) than the activity of at least one protein that is different from the first protein.

The term "aberrant activity" refers to activity deviating from normal activity. The term "increased activity" refers to activity higher than normal activity.

The terms "composition" and "formulation" are used interchangeably.

A "subject" as used herein refers to a human (i.e., a male or a female of any age group, e.g., a pediatric subject (e.g., an infant, child, or an adolescent) or an adult subject (e.g., a young adult, a middle-aged adult, or a senior adult)). The subject may also include any non-human animals including, but not limited to a cynomolgus monkey or a rhesus monkey, a cattle, a pig, a horse, a sheep, a goat, a cat, a dog, a mouse, a rat, a rabbit, or a bird (e.g., a commercially relevant bird, such as a chicken, a duck, a goose, or a turkey). In certain embodiments, the non-human animal is a fish, a reptile, or an amphibian. In certain embodiments, the non-human animal is a mammal, a primate, a rodent, an avian, an equine, an ovine, a bovine, a caprine, a feline, or a canine. The non-human animal may be a male or a female at any stage of development. The non-human animal may be a transgenic animal or a genetically engineered animal. A "patient" refers to a human subject in need of treatment of a disease. The subject may also be a plant.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The terms "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen) to delay or prevent disease occurrence. Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response, i.e., treating the condition (therapeutically or prophylactically). As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay, minimize, or abolish one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

An "infection" or "infectious disease" refers to an infection with a microorganism, such as a protozoa, fungus, bacteria or virus. In certain embodiments, the infection is an infection with a bacteria, i.e., a bacterial infection. Various infections include, but are not limited to, skin infections, GI infections, urinary tract infections, genito-urinary infections, sepsis, blood infections, and systemic infections.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

DETAILED DESCRIPTION

Figure 1:
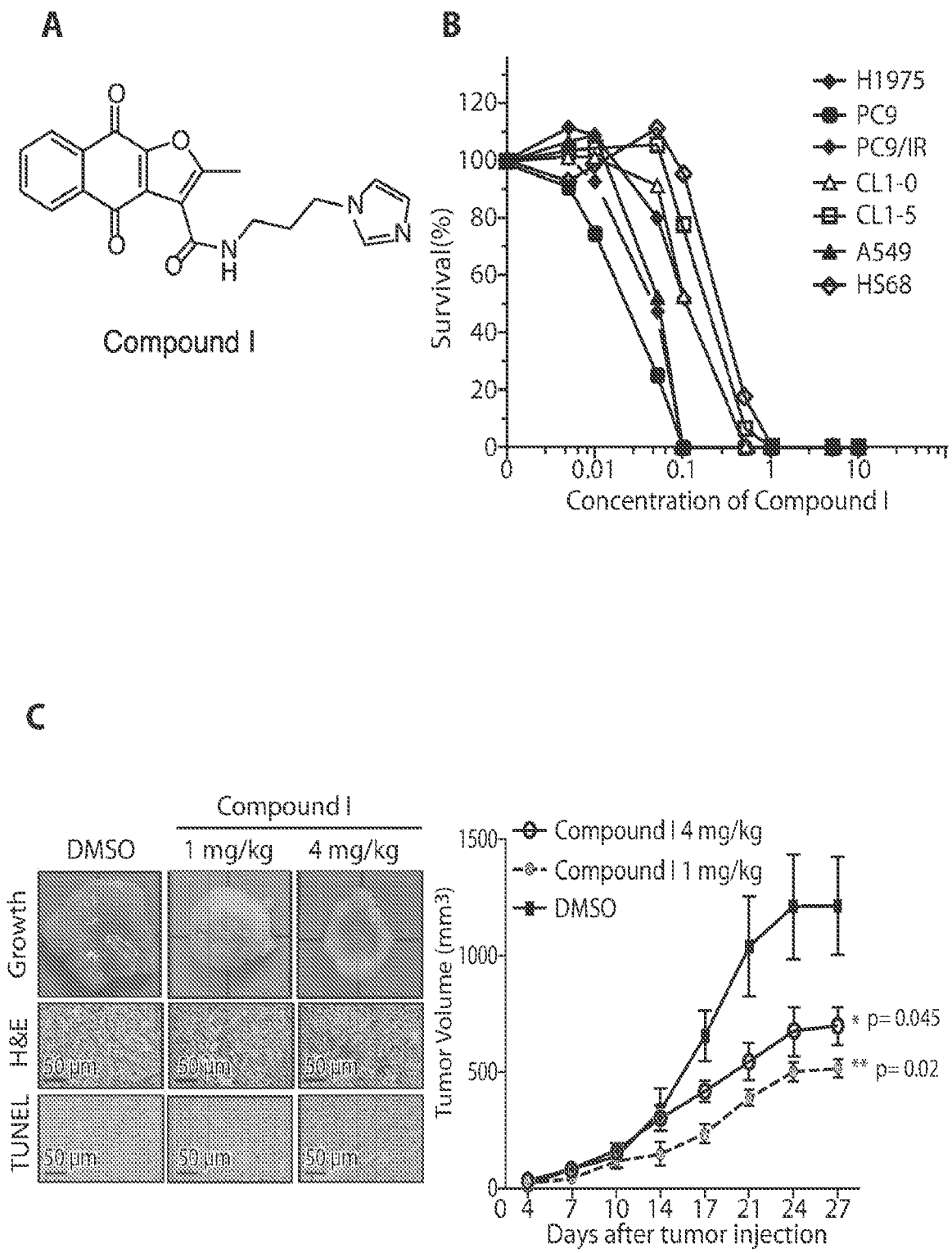
FIG. 1 shows exemplary results for the effects of compound 1 on cell cycle progression and inhibition of tumor growth in vivo. Panel (A): The structure of compound 1. Panel (B): A chart showing exemplary results for the cytotoxicity assay of Compound 1-treated cancer cells for 72 hours. The cells were treated with 0-10 µM of compound for 72 h in complete medium and subjected to an SRB assay. Panel (C): Photos showing the different tumor sizes and TUNEL assay results between DMSO control and Compound 1-treated mice. H1975 ($3\times10^6$) cells were subcutaneously injected into male nu/nu mice, and daily treated intraperitoneally with Compound I at indicated dose or DMSO for 4 weeks. During the treatment, tumor size and body weights were measured every 3 to 4 days; and the histology was confirmed by H&E staining (left lower panel of panel (C).

The present disclosure provides inhibitors of minichromosome maintenance eukaryote replicative helicase subunit 2 (MCM2), for example, the compounds of Formulas (I) and (II), which bind MCM2 and inhibit its activity. The compounds described herein are useful in inhibiting MCM2 activity, thereby benefiting the treatment of diseases associated with MCM2, for example, proliferative diseases such as cancer or infectious diseases such as bacterial infection. Also provided in the present disclosure are pharmaceutical compositions, kits, methods of using the MCM2 inhibitors described herein for treating any of the target diseases described herein.

Minichromosome Maintenance Eukaryote Replicative Helicase (MCM) Inhibiting Compounds One aspect of the present disclosure relates to the MCM inhibitors (e.g., inhibitors for any of MCM2-MCM7) as described herein, as well as their pharmaceutically acceptable salts, solvates, hydrates, polymorphs, co-crystals, tautomers, stereoisomers, isotopically labeled derivatives, or prodrugs. These compounds are useful in treating and/or preventing proliferative and/or infectious diseases in a subject.

In certain embodiments, a compound described herein is of Formula (I):

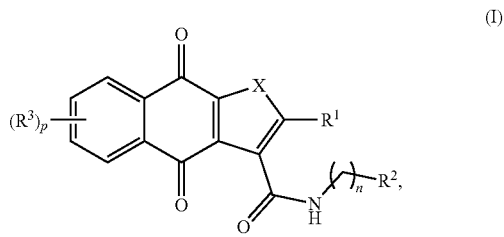

in which $R^1$-$R^3$, X, n, and p are as described herein, or pharmaceutically acceptable salt, solvate, hydrate, polymorph, co-crystal, tautomer, stereoisomer, isotopically labeled derivative, or prodrug thereof.

In certain embodiments, a compound described herein is of Formula (II):

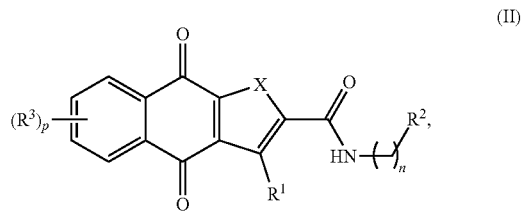

in which $R^1$-$R^3$, X, n, and p are as described herein, or pharmaceutically acceptable salt, solvate, hydrate, polymorph, co-crystal, tautomer, stereoisomer, isotopically labeled derivative, or prodrug thereof.

In Formulas (I) and (II), X is in an aromatic ring. In some embodiments, X can be —O—. In some embodiments, X can be —S—. In some embodiments, X can be —$NR^X$—, in which $R^X$ is as defined herein. In some embodiments, $R^X$ can be hydrogen. In some embodiments, $R^X$ can be optionally substituted $C_{1-6}$ alkyl (e.g., methyl, ethyl, or propyl). In some embodiments, $R^X$ can be optionally substituted $C_2$-$C_6$ alkenyl. In some embodiments, $R^X$ can be optionally substituted $C_2$-$C_{10}$ alkynyl (e.g., optionally substituted, propynyl or butynyl). In certain embodiments, $R^X$ can be optionally substituted carbocyclyl (e.g., substituted or unsubstituted, 3- to 7-membered, monocyclic carbocyclyl comprising zero, one, or two double bonds in the carbocyclic ring system). In some embodiments, $R^X$ can be optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In some embodiments, $R^X$ can be optionally substituted aryl (e.g., phenyl, or benzyl). In some embodiments, $R^X$ can be optionally substituted 5- to 7-membered monocyclic heteroaryl, wherein one, two, three, or four atoms in the heteroaryl ring system are independently nitrogen, oxygen, or sulfur. In some embodiments, $R^X$ can be optionally substituted 8- to 10-membered bicyclic heteroaryl, wherein one, two, three, or four atoms in the heteroaryl ring system are independently nitrogen, oxygen, or sulfur. In some embodiments, $R^X$ can be a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In one example, X can be —NH—. In another example, X can be —NMe-.

In some embodiments, R¹ in Formulas (I) and/or (II) can be hydrogen. In some embodiments, R¹ can be halogen (e.g., F, Cl, Br, or I). In some embodiments, R¹ can be substituted or unsubstituted $C_{1-6}$ alkyl (e.g., substituted or unsubstituted, methyl, ethyl, propyl or butyl). In some embodiments, R¹ can be methyl. In some embodiments, R¹ can be ethyl. In some embodiments, R¹ can be propyl. In some embodiments, R¹ can be isopropyl. In some embodiments, R¹ can be optionally substituted $C_2$-$C_6$ alkenyl. In some embodiments, R¹ can be optionally substituted $C_2$-$C_{10}$ alkynyl (e.g., optionally substituted, propynyl or butynyl). In certain embodiments, R¹ can be optionally substituted carbocyclyl (e.g., substituted or unsubstituted, 3- to 7-membered, monocyclic carbocyclyl comprising zero, one, or two double bonds in the carbocyclic ring system). In some embodiments, R¹ can be optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In some embodiments, R¹ can be optionally substituted aryl (e.g., phenyl, or benzyl). In some embodiments, R¹ can be phenyl. In some embodiments, R¹ can be benzyl. In some embodiments, R¹ can be optionally substituted 5- to 7-membered monocyclic heteroaryl, wherein one, two, three, or four atoms in the heteroaryl ring system are independently nitrogen, oxygen, or sulfur. In some embodiments, R¹ can be optionally substituted 8- to 10-membered bicyclic heteroaryl, wherein one, two, three, or four atoms in the heteroaryl ring system are independently nitrogen, oxygen, or sulfur. In some embodiments, R¹ can be —CN. In some embodiments, R¹ can be —NO₂. In some embodiments, R¹ can be —N₃.

In Formulas (I) and/or (II), in some embodiments, n is 1. In some embodiments, n is 2. In some embodiments, n is 3. In some embodiments, n is 4. In some embodiments, n is 5.

In Formulas (I) and/or (II), in some embodiments, R² can be hydrogen. In some embodiments, R² can be halogen (e.g., F, Cl, Br, or I). In some embodiments, R² can be substituted or unsubstituted $C_{1-6}$ alkyl (e.g., substituted or unsubstituted, methyl, ethyl, propyl or butyl). In some embodiments, R² can be optionally substituted $C_2$-$C_6$ alkenyl. In some embodiments, R² can be optionally substituted $C_2$-$C_{10}$ alkynyl (e.g., optionally substituted, propynyl or butynyl). In certain embodiments, R² can be optionally substituted carbocyclyl (e.g., substituted or unsubstituted, 3- to 7-membered, monocyclic carbocyclyl comprising zero, one, or two double bonds in the carbocyclic ring system). In some embodiments, R² can be optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In some embodiments, R² can be

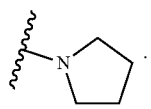 [SMILES: *N1CCCC1 ; "."]

In some embodiments, R² can be

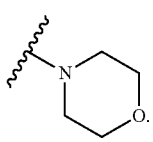 [SMILES: *N1CCOCC1]

In some embodiments, R² can be optionally substituted aryl (e.g., phenyl, or benzyl). In some embodiments, R² can be phenyl. In some embodiments, R² can be benzyl. In some embodiments, R² can be optionally substituted 5- to 7-membered monocyclic heteroaryl, wherein one, two, three, or four atoms in the heteroaryl ring system are independently nitrogen, oxygen, or sulfur. In some embodiments, R² can be

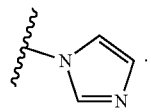

In some embodiments, R² can be

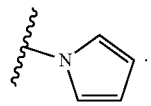

In some embodiments, R² can be optionally substituted 8- to 10-membered bicyclic heteroaryl, wherein one, two, three, or four atoms in the heteroaryl ring system are independently nitrogen, oxygen, or sulfur.

Formulas (I) and/or (II) include one or more instances of R³. In some embodiments, at least one instance of R³ can be hydrogen. In some embodiments, at least one instance of R³ can be halogen (e.g., F, Cl, Br, or I). In some embodiments, at least one instance of R³ can be substituted or unsubstituted $C_{1-6}$ alkyl (e.g., substituted or unsubstituted, methyl, ethyl, propyl or butyl). In some embodiments, at least one instance of R³ can be optionally substituted $C_2$-$C_6$ alkenyl. In some embodiments, at least one instance of R³ can be optionally substituted $C_2$-$C_{10}$ alkynyl (e.g., optionally substituted, propynyl or butynyl). In certain embodiments, at least one instance of R³ can be optionally substituted carbocyclyl (e.g., substituted or unsubstituted, 3- to 7-membered, monocyclic carbocyclyl comprising zero, one, or two double bonds in the carbocyclic ring system). In some embodiments, at least one instance of R³ can be optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In some embodiments, at least one instance of R³ can be optionally substituted 5- to 7-membered monocyclic heteroaryl, wherein one, two, three, or four atoms in the heteroaryl ring system are independently nitrogen, oxygen, or sulfur. In some embodiments, at least one instance of R³ can be optionally substituted 8- to 10-membered bicyclic heteroaryl, wherein one, two, three, or four atoms in the heteroaryl ring system are independently nitrogen, oxygen, or sulfur. In some embodiments, at least one instance of R³ can be —CN. In some embodiments, at least one instance of R³ can be —NO₂. In some embodiments, at least one instance of R³ can be —N₃. In some embodiments, at least one instance of R³ can be —OR$^A$, in which R$^A$ is as defined herein, (e.g., —OH, —O(substituted or unsubstituted $C_{1-6}$ alkyl) (e.g., —OMe, —OCF₃, —OEt, —OPr, or —OBu). In certain embodiments, at least one instance of R³ can be —N(R$^B$)₂, in which R$^B$ is as defined herein, (e.g., —NMe₂). In certain embodiments, at least one instance of R³ can be —C(=O)R$^A$, in which R$^A$ is as defined herein, (e.g., acetyl). In certain embodiments, at least one instance of $R^3$ is —$SO_2R^A$, in which $R^A$ is as defined herein.

In some embodiments, $R^A$ and/or $R^B$ can be hydrogen. In some embodiments, $R^A$ and/or $R^B$ can be halogen (e.g., F, Cl, Br, or I). In some embodiments, $R^A$ and/or $R^B$ can be substituted or unsubstituted $C_{1-6}$ alkyl (e.g., substituted or unsubstituted, methyl, ethyl, propyl or butyl). In some embodiments, $R^A$ and/or $R^B$ can be methyl. In some embodiments, $R^A$ and/or $R^B$ can be ethyl. In some embodiments, $R^A$ and/or $R^B$ can be propyl. In some embodiments, $R^A$ and/or $R^B$ can be isopropyl. In some embodiments, $R^A$ and/or $R^B$ can be optionally substituted $C_2$-$C_6$ alkenyl. In some embodiments, $R^A$ and/or $R^B$ can be optionally substituted $C_2$-$C_{10}$ alkynyl (e.g., optionally substituted, propynyl or butynyl). In certain embodiments, $R^A$ and/or $R^B$ can be optionally substituted carbocyclyl (e.g., substituted or unsubstituted, 3- to 7-membered, monocyclic carbocyclyl comprising zero, one, or two double bonds in the carbocyclic ring system). In some embodiments, $R^A$ and/or $R^B$ can be optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In some embodiments, $R^A$ and/or $R^B$ can be optionally substituted aryl (e.g., phenyl, or benzyl). In some embodiments, $R^A$ and/or $R^B$ can be phenyl. In some embodiments, $R^A$ and/or $R^B$ can be benzyl. In some embodiments, $R^A$ and/or $R^B$ can be optionally substituted 5- to 7-membered monocyclic heteroaryl, wherein one, two, three, or four atoms in the heteroaryl ring system are independently nitrogen, oxygen, or sulfur. In some embodiments, $R^A$ and/or $R^B$ can be optionally substituted 8- to 10-membered bicyclic heteroaryl, wherein one, two, three, or four atoms in the heteroaryl ring system are independently nitrogen, oxygen, or sulfur. In some embodiments, $R^A$ can be an oxygen protecting group if attached to an oxygen atom (e.g., t-butyloxycarbonyl (BOC or Boc), methoxylmethyl (MOM) or methylthiomethyl (MTM)). In some embodiments, $R^B$ can be a nitrogen protecting group if attached to an nitrogen atom (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, two instances of $R^B$ can be taken together with the intervening atoms to form substituted or unsubstituted heterocyclyl or substituted or unsubstituted heteroaryl.

In some embodiments, the compound of Formula (I) can be of one of the following formulae: Formula (I-A), Formula (I-B), Formula (I-C), or a pharmaceutically acceptable salt, solvate, hydrate, polymorph, co-crystal, tautomer, stereoisomer, isotopically labeled derivative, or prodrug thereof.

In some embodiments, the compound of Formula (II) can be of one of the following formulae: Formula (II-A), Formula (II-B), Formula (II-C), or a pharmaceutically acceptable salt, solvate, hydrate, polymorph, co-crystal, tautomer, stereoisomer, isotopically labeled derivative, or prodrug thereof.

In some embodiments, the compound of Formulas (I) or (II) can be of the formula of compounds described herein, or a pharmaceutically acceptable salt, solvate, hydrate, polymorph, co-crystal, tautomer, stereoisomer, isotopically labeled derivative, or prodrug thereof.

Exemplary compounds of Formula (I) are provided herein. Below is an additional example:

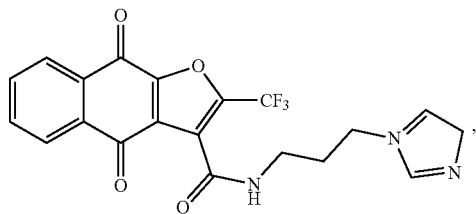

or a pharmaceutically acceptable salt thereof.

The compounds described herein can be prepared from readily available starting materials using methods known in the art. It will be appreciated that where typical or preferred process conditions (i.e., reaction temperatures, times, mole ratios of reactants, solvents, and pressures, etc.) are given, other process conditions can also be used unless otherwise stated. Optimum reaction conditions may vary with the particular reactants or solvents used, but such conditions can be determined by those skilled in the art by routine optimization procedures. The chemicals used in the above-described synthetic routes may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the compounds. In addition, various synthetic steps may be performed in an alternate sequence or order to give the desired compounds. Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The compounds of Formulas (I) and (II) provided herein can be prepared from readily available starting materials using the following general methods and procedures. An exemplary schematic illustration for synthesizing the MCM2 inhibiting compounds described herein is provided in the Examples section below. Where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Pharmaceutical Compositions and Kits

The present disclosure provides pharmaceutical compositions comprising a compound described herein, or a pharmaceutically acceptable salt thereof, and optionally a pharmaceutically acceptable excipient. In certain embodiments, a pharmaceutical composition described herein comprises a compound described herein, or a pharmaceutically acceptable salt thereof, and a pharmaceutically acceptable excipient. The pharmaceutical compositions described herein are useful in treating and/or preventing proliferative diseases (e.g., cancer) and/or infectious diseases (e.g., bacterial infections).

In certain embodiments, a subject being treated herein is an animal. The animal may be of either sex and may be at any stage of development. In certain embodiments, the subject is a human. In certain embodiments, the subject is a mammal (e.g., non-human mammal). In certain embodiments, the subject is a domesticated animal, such as a dog, cat, cow, pig, horse, sheep, or goat. In certain embodiments, a subject being treated herein is a companion animal such as a dog or cat. In certain embodiments, a subject being treated herein is a livestock animal such as a cow, pig, horse, sheep, or goat. In certain embodiments, a subject being treated herein is a zoo animal. In another embodiment, a subject being treated herein is a research animal such as a rodent (e.g., mouse, rat), dog, pig, or non-human primate. In certain embodiments, the animal is a genetically engineered animal. In certain embodiments, the animal is a transgenic or genetically engineered animal (e.g., transgenic mice and transgenic pigs).

In certain embodiments, the cell contacted with an effective amount of a compound or pharmaceutical composition described herein is in vitro. In certain embodiments, the contacted cell is ex vivo. In certain embodiments, the cell described herein is in vivo. In certain embodiments, the cell described herein is a malignant cell (e.g., malignant blood cell).

In certain embodiments, the compound described herein is provided in an effective amount in the pharmaceutical composition. In certain embodiments, the effective amount is a therapeutically effective amount (e.g., amount effective for inhibiting MCM2 and/or treating a proliferative disease or an infectious disease in a subject in need thereof). In certain embodiments, the proliferative disease is cancer, e.g., breast cancer, colorectal cancer, pancreatic cancer, gastric cancer, or cervical cancer. In certain embodiments, the disease is bacterial infection, such as *Staphylococcus* infection, *Streptococcus* infection, *Enterococcus* infection and gram negative bacterial infection. In certain embodiments, the effective amount is a prophylactically effective amount (e.g., amount effective for preventing a proliferative disease or an infectious disease in a subject in need thereof and/or for keeping a subject in need thereof in remission of a proliferative disease). In certain embodiments, the effective amount is a therapeutically effective amount (e.g., amount effective for treating an infectious disease or a proliferative disease in a subject in need thereof).

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof. In certain embodiments, the composition of the instant disclosure is encapsulated in a carrier vehicle, which may be rigid vesicles, elastic vesicles, monolayer vesicles, multi-layer vesicles, liposomes, niosomes, proniosomes, Transfersomes®, ethosomes, L-595-PEG-8-L vesicles, nanoemulsions, nanosomes, nanoparticles, or a combination thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

The compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

In certain embodiments, a kit described herein includes a first container comprising a compound or pharmaceutical composition described herein. In certain embodiments, a kit described herein is useful in treating a disease associated with MCM2, for example, a proliferative disease (e.g., breast cancer, colorectal cancer, pancreatic cancer, gastric cancer, or cervical cancer) and/or infectious disease including but not limited to bacterial and viral infections. In certain embodiments, the bacterial infection is *Staphylococcus* infection, *Streptococcus* infection, *Enterococcus* infection or gram negative bacterial infection in a subject in need thereof. In some embodiments, the MCM2 inhibitory compounds described herein are useful in treating diseases associated with bacterial infections.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a proliferative disease and/or infectious disease in a subject in need thereof, and/or preventing a proliferative disease and/or infectious disease in a subject in need thereof. A kit described herein may include one or more additional pharmaceutical agents described herein as a separate composition.

Methods of Treatment

As shown in the Examples below, exemplary MCM inhibitors described herein successfully induce protein degradation of MCM (e.g., MCM2-MCM7), may target MCM, and contribute to cell apoptosis in cells such as lung cancer cells.

Accordingly, the present disclosure provides methods of treating a proliferative disease, or an infectious disease in a subject in need thereof, the methods comprising administering to the subject an effective amount (e.g., therapeutically effective amount) of a compound, or pharmaceutical composition thereof, described herein.

Another aspect of the present disclosure relates to methods of preventing proliferative disease and/or infectious disease in a subject in need thereof, the methods comprising administering to the subject an effective amount (e.g., prophylactically effective amount) of a compound, or pharmaceutical composition thereof, described herein.

The compounds and pharmaceutical compositions described herein are useful in treating diseases associated with MCM, for example, proliferative diseases and/or infectious diseases. In certain embodiments, the proliferative disease is cancer. In certain embodiments, the proliferative disease is lung cancer. In certain embodiments, the proliferative disease is non-small cell lung cancer, breast cancer, colorectal cancer, pancreatic cancer, gastric cancer, or cervical cancer. In certain embodiments, the infectious disease is bacterial infection, such as *Staphylococcus* infection, *Streptococcus* infection, *Enterococcus* infection or gram negative bacterial infection.

In certain embodiments, the method described herein further includes administering to the subject an additional pharmaceutical agent. In certain embodiments, the method described herein further includes contacting the biological sample with an additional pharmaceutical agent. In certain embodiments, the method described herein further includes contacting the tissue with an additional pharmaceutical agent. In certain embodiments, the method described herein further includes contacting the cell with an additional pharmaceutical agent. In certain embodiments, the method described herein further includes radiotherapy, immunotherapy, and/or transplantation (e.g., bone marrow transplantation).

The compounds and compositions provided herein can be administered by any route, including enteral (e.g., oral), parenteral, intravenous, intramuscular, intra-arterial, intracranial, intramedullary, intrathecal, subcutaneous, intraventricular, transdermal, intradermal, interdermal, rectal, intravaginal, intraperitoneal, topical (as by powders, ointments, creams, and/or drops), by any means that facilitate in vivo or ex vivo transport of the compound or composition as described herein in, into, or through tissue/skin of a subject (such as iontophoresis), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), transfusion, perfusion, regional administration via blood and/or lymph supply, and/or direct administration to an affected site, such as intra-tumoral. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, biological sample, tissue, or cell. In certain embodiments, the duration between the first dose and last dose of the multiple doses is three months, six months, or one year. In certain embodiments, the duration between the first dose and last dose of the multiple doses is the lifetime of the subject, biological sample, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower, higher, or the same as that administered to an adult.

A compound or composition, as described herein, can be administered in combination with one or more additional pharmaceutical agents (e.g., therapeutically and/or prophylactically active agents) useful in treating and/or preventing a proliferative disease disease and/or infectious disease. The compounds or compositions can be administered in combination with additional pharmaceutical agents that improve their activity (e.g., activity (e.g., potency and/or efficacy) in treating a proliferative disease and/or infectious disease in a subject in need thereof, and/or in preventing a proliferative disease and/or infectious disease in a subject in need thereof), improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, for different disorders, and/or it may achieve different effects. In certain embodiments, a pharmaceutical composition described herein including a compound described herein is administered to a patient in need thereof, to advantageously treat one or more diseases. In certain embodiments, said one or more disease is a proliferative disease, an infectious disease, or a combination thereof. In a preferred embodiment, said one or more disease is cancer, a bacterial infection, or a combination thereof. It is believed that an MCM2-inhibitory compound described herein would act synergistically with at least one additional therapeutic agent in inhibiting target cell growth (e.g., inhibiting the growth of cancer cells or bacterial cells, or cells infected with a pathogen such as a virus).

The compound or composition may be administered concurrently with, prior to, or subsequent to one or more additional pharmaceutical agents, which may be useful as, e.g., combination therapies in treating and/or preventing a proliferative disease and/or infectious disease. In certain embodiments, the compound or composition described herein can be administered to a patient in need thereof, wherein the proliferative disease or the infectious disease of the patient is resistant to at least one pharmaceutical agent. In certain embodiments, the proliferative disease is cancer and said cancer is resistant to one or more anti-cancer agents including but not limited to tyrosine kinase inhibitors (TKIs) such as Gefitinib or elrotinib. In certain embodiments, the infectious disease is bacterial infection and said bacterial strain is resistant to one or more antibiotics including but not limited to methicillin and ciprofloxacin. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful in treating a proliferative disease and/or infectious disease. In certain embodiments, the additional pharmaceutical agent is a pharmaceutical agent useful in preventing a proliferative disease and/or infectious disease. In certain embodiments, the additional pharmaceutical agent is Gefitinib (Iressa). In certain embodiments, the additional pharmaceutical agent is a pharmaceutical agent approved by a regulatory agency (e.g., the US FDA) for treating and/or preventing a proliferative disease and/or infectious disease. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

In certain embodiments, the additional pharmaceutical agent is an anti-proliferative agent (e.g., anti-cancer agent). In certain embodiments, the additional pharmaceutical agent is an anti-angiogenesis agent, anti-inflammatory agent, immunosuppressant, anti-bacterial agent, anti-viral agent, cardiovascular agent, cholesterol-lowering agent, anti-diabetic agent, anti-allergic agent, pain-relieving agent, or a combination thereof. In certain embodiments, the compounds described herein or pharmaceutical compositions can be administered in combination with an anti-cancer therapy including, but not limited to, transplantation (e.g., bone marrow transplantation, stem cell transplantation), surgery, radiation therapy, immunotherapy, and chemotherapy.

Methods of Synthesis

An exemplary synthetic scheme for making the compounds described herein is provided below:

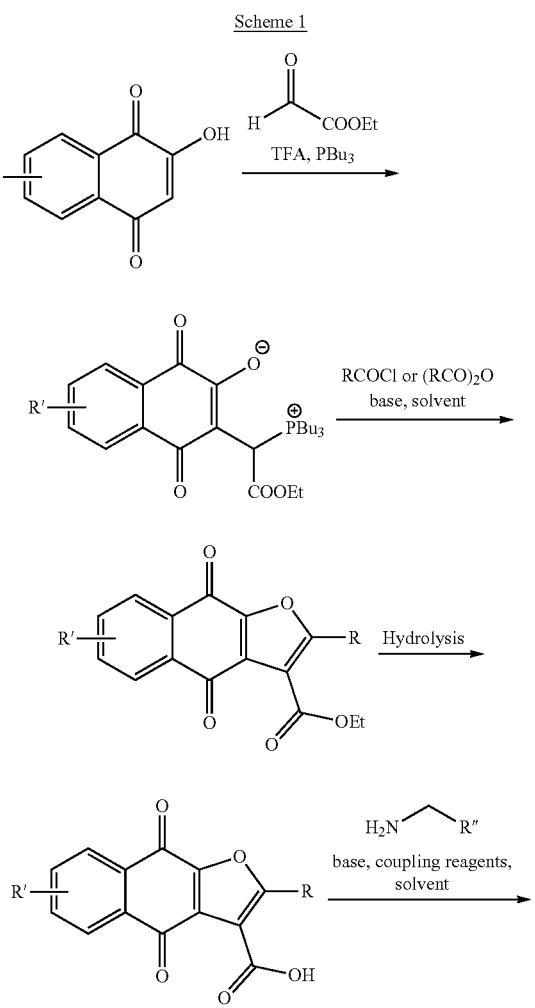

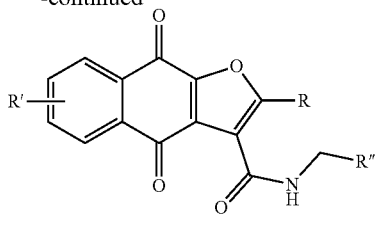

In one aspect, the present invention provides methods for preparing compounds of Formulas (I) and (II). In certain embodiments, the method for preparing a compound of Formula (I) comprises coupling a compound of Formula (I-D):

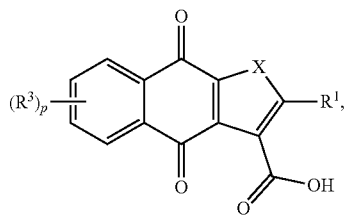

(I-D)

or a salt thereof, with a compound of the formula:

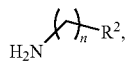

or a salt thereof, under conditions sufficient to form a compound of Formula (I):

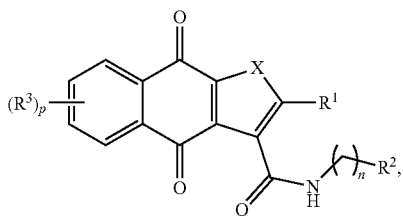

(I)

or a salt thereof, wherein n, p, X, $R^X$, $R^1$, $R^2$, and $R^3$ are as defined herein.

In certain embodiments, the method for preparing a compound of Formula (II) comprises coupling a compound of Formula (II-D):

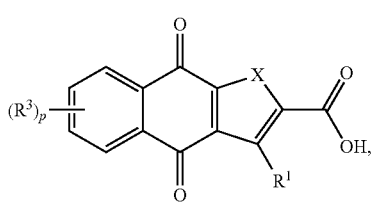

(II-D)

or a salt thereof, with a compound of the formula:

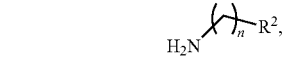

or a salt thereof, under conditions sufficient to form a compound of Formula (II):

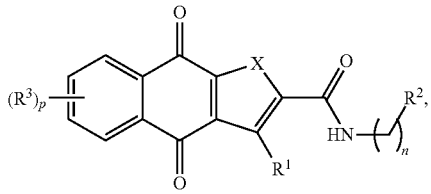

(II)

or a salt thereof, wherein n, p, X, $R^X$, $R^1$, $R^2$, and $R^3$ are as defined herein.

In certain embodiments, the step of coupling a compound of Formula (I-D) with a compound of the formula:

to form a compound of Formula (I) is carried out in the presence of a coupling reagent.

In certain embodiments, the step of coupling a compound of Formula (II-D) with a compound of the formula:

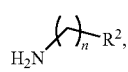

to form a compound of Formula (II) is carried out in the presence of a coupling reagent.

In certain embodiments, the step of coupling is carried out in the presence of a coupling reagent and a base. In certain embodiments, the coupling reagent is a reagent that promotes the formation of an amide bond (e.g., a peptide coupling reagent). Any coupling reagent (e.g., peptide coupling reagent) known in the art may be used. In certain embodiments, the coupling reagent is N,N,N',N'-Tetramethyl-O-(1H-benzotriazol-1-yl)uronium hexafluorophosphate (HBTU). In certain embodiments, the coupling reagent is 1,1'-Carbonyldiimidazole (CDI). In certain embodiments, the step of coupling is carried out in the presence of a base. In certain embodiments, the base is a pyridine. In certain embodiments, the base is an aminopyridine. In certain embodiments, the base is 4-dimethylaminopyridine (DMAP). In certain embodiments, the step of coupling is carried out in the presence of a coupling reagent and a base. In certain embodiments, the step of coupling is carried out in the presence of HBTU and DMAP. In certain embodiments, the step of coupling is carried out in a solvent. In certain embodiments, the solvent is N,N-dimethylformamide (DMF).

In certain embodiments, the method of preparing a compound of Formula (I) comprises hydrolyzing a compound of Formula (I-E):

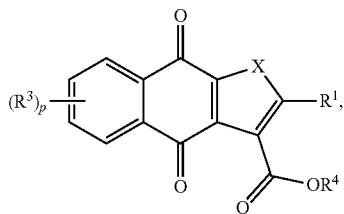

(I-E)

or a salt thereof, under conditions sufficient to form a compound of Formula (I-D):

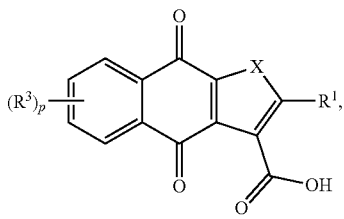

(I-D)

or a salt thereof, wherein X, $R^1$, $R^3$, and p are as defined herein; and $R^4$ is optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group.

In certain embodiments, the method of preparing a compound of Formula (II) comprises hydrolyzing a compound of Formula (II-E):

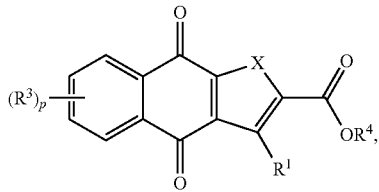

(II-E)

or a salt thereof, under conditions sufficient to form a compound of Formula (II-D):

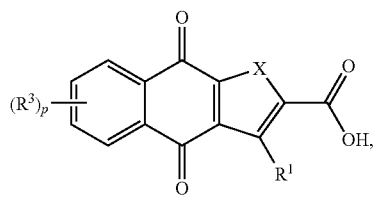

(II-D)

or a salt thereof, wherein X, $R^1$, $R^3$, and p are as defined herein; and $R^4$ is optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group.

In certain embodiments, the step of hydrolyzing a compound of Formula (I-E) to form a compound of Formula (I-D) is carried out in the presence of a base. In certain embodiments, the step of hydrolyzing a compound of Formula (II-E) to form a compound of Formula (II-D) is carried out in the presence of a base. In certain embodiments, the base is hydroxide or an alkoxide. In certain embodiments, the base is hydroxide. In certain embodiments, the base is selected from the group consisting of sodium hydroxide, potassium hydroxide, and lithium hydrozide. In certain embodiments, the base is lithium hydrozide (LiOH). In certain embodiments, the base is sodium hydroxide (NaOH). In certain embodiments, the step of hydrolyzing is carried out in the presence of water. In certain embodiments, the step of hydrolyzing is carried out in the presence of a base and water. In certain embodiments, the step of hydrolyzing is carried out in the presence of lithium hydrozide (LiOH) and water. In certain embodiments, the step of hydrolyzing is carried out in the presence of a solvent. In certain embodiments, the solvent is tetrahydrofuran (THF). In certain embodiments, the solvent is a mixture of THF and water.

As generally defined herein, $R^4$ is optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group. In certain embodiments, $R^4$ is optionally substituted alkyl. In certain embodiments, $R^4$ is optionally substituted alkenyl. In certain embodiments, $R^4$ is optionally substituted alkynyl. In certain embodiments, $R^4$ is optionally substituted carbocyclyl. In certain embodiments, $R^4$ is optionally substituted heterocyclyl. In certain embodiments, $R^4$ is optionally substituted aryl. In certain embodiments, $R^4$ is optionally substituted heteroaryl. In certain embodiments, $R^4$ is an oxygen protecting group. In certain embodiments, $R^4$ is optionally substituted $C_{1-6}$ alkyl. In certain embodiments, $R^4$ is unsubstituted $C_{1-6}$ alkyl. In certain embodiments, $R^4$ is selected from the group consisting of methyl, ethyl, n-propyl, iso-propyl, n-butyl, iso-butyl, sec-butyl, and tert-butyl. In certain embodiments, $R^4$ is ethyl. In certain embodiments, $R^4$ is methyl.

In certain embodiments, the method of preparing a compound of Formula (I) comprises contacting a compound of Formula (I-G):

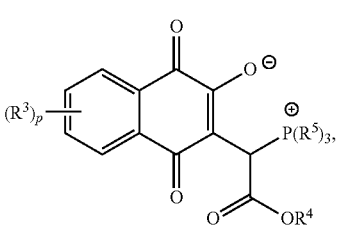

(I-G)

or a salt thereof, with a compound of formula:

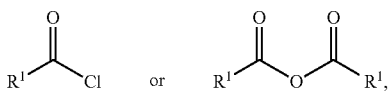

or a salt thereof, under conditions sufficient to form a compound of Formula (I-F):

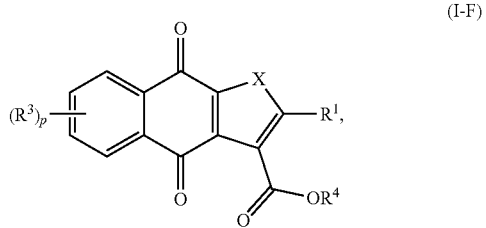

or a salt thereof, wherein $R^1$, $R^3$, $R^4$, and p are as defined herein; and each instance of $R^5$ is independently optionally substituted alkyl, optionally substituted alkenyl, optionally substituted alkynyl, optionally substituted carbocyclyl, optionally substituted heterocyclyl, optionally substituted aryl, or optionally substituted heteroaryl; or optionally two $R^5$ are joined together with the intervening atoms to form optionally substituted carbocyclyl or optionally substituted heterocyclyl.

In certain embodiments, the method of preparing a compound of Formula (II) comprises contacting a compound of Formula (II-G):

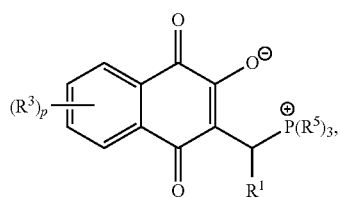

or a salt thereof, with a compound of formula:

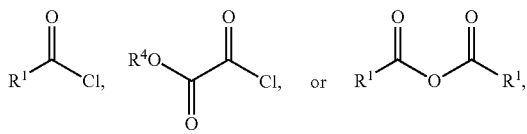

or a salt thereof, under conditions sufficient to form a compound of Formula (II-F):

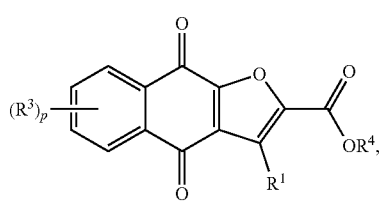

or a salt thereof,
wherein:
$R^4$ is optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group; and each instance of $R^5$ is independently optionally substituted alkyl, optionally substituted alkenyl, optionally substituted alkynyl, optionally substituted carbocyclyl, optionally substituted heterocyclyl, optionally substituted aryl, or optionally substituted heteroaryl; or optionally two $R^5$ are joined together with the intervening atoms to form optionally substituted carbocyclyl or optionally substituted heterocyclyl.

In certain embodiments, the step of contacting a compound of Formula (I-G) with a compound of formula:

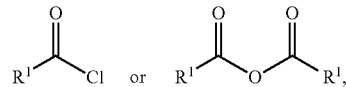

to form a compound of Formula (I-F) is carried out in the presence of a base. In certain embodiments, the step of contacting a compound of Formula (II-G) with a compound of formula:

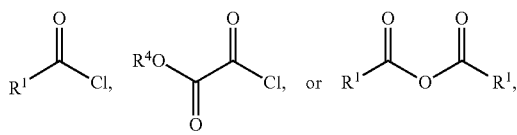

to form a compound of Formula (II-F) is carried out in the presence of a base. In certain embodiments, a compound of Formula (II-G) is contacted with a compound of formula:

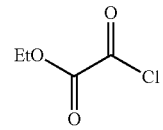

to form a compound of Formula (II-F). In certain embodiments, the base is an amine base. In certain embodiments, the base is a trialkylamine. In certain embodiments, the base is triethylamine. In certain embodiments, the base is N,N-Diisopropylethylamine (DIPEA). In certain embodiments, the step of contacting is carried out in the presence of a solvent. In certain embodiments, the solvent is tetrahydrofuran (THF).

As generally defined herein, each instance of $R^5$ is independently optionally substituted alkyl, optionally substituted alkenyl, optionally substituted alkynyl, optionally substituted carbocyclyl, optionally substituted heterocyclyl, optionally substituted aryl, or optionally substituted heteroaryl; or optionally two $R^5$ are joined together with the intervening atoms to form optionally substituted carbocyclyl or optionally substituted heterocyclyl. In certain embodiments, at least one instance of $R^5$ is optionally substituted alkyl. In certain embodiments, at least one instance of $R^5$ is optionally substituted alkenyl. In certain embodiments, at least one instance of $R^5$ is optionally substituted alkynyl. In certain embodiments, at least one instance of $R^5$ is optionally substituted carbocyclyl. In certain embodiments, at least one instance of $R^5$ is optionally substituted heterocyclyl. In certain embodiments, at least one instance of $R^5$ is optionally substituted aryl. In certain embodiments, at least one instance of $R^5$ is optionally substituted heteroaryl. In certain embodiments, at least one instance of $R^5$ is optionally substituted $C_{1-6}$ alkyl. In certain embodiments, at least one instance of $R^5$ is unsubstituted $C_{1-6}$ alkyl. In certain embodiments, at least one instance of $R^5$ is selected from the group consisting of methyl, ethyl, n-propyl, iso-propyl, n-butyl, iso-butyl, sec-butyl, and tert-butyl. In certain embodiments, at least one instance of $R^5$ is n-butyl. In certain embodiments, each instance of $R^5$ is n-butyl. In certain embodiments, at least one instance of $R^5$ is phenyl. In certain embodiments, each instance of $R^5$ is phenyl.

In certain embodiments, the method of preparing a compound of Formula (I) comprises contacting a compound of the formula:

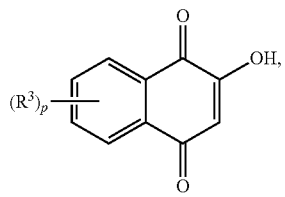

or a salt thereof, with a compound of the formula:

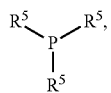

or a salt thereof, and a compound of the formula:

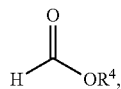

or a salt thereof, under conditions sufficient to form a compound of Formula (I-G):

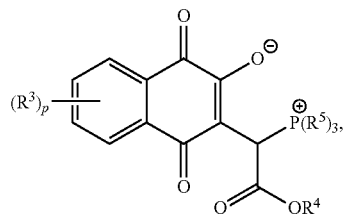

or a salt thereof, wherein $R^3$, $R^4$, $R^5$, and p are as defined herein.

In certain embodiments, the method of preparing a compound of Formula (II) comprises contacting a compound of the formula:

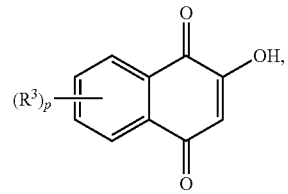

or a salt thereof, with a compound of the formula:

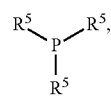

or a salt thereof, and a compound of the formula:

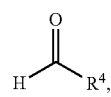

or a salt thereof, under conditions sufficient to form a compound of Formula (II-G):

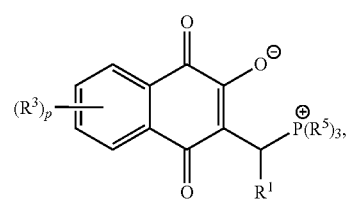

or a salt thereof, wherein $R^3$, $R^4$, $R^5$, and p are as defined herein.

In certain embodiments, the step of contacting a compound of the formula:

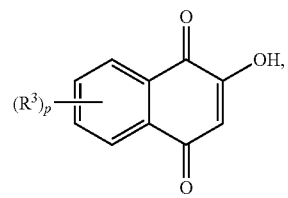

with a compound of the formula:

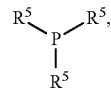

and a compound of the formula:

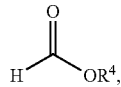

to form a compound of Formula (I-G) is carried out in the presence of an acid. In certain embodiments, the step of contacting a compound of the formula:

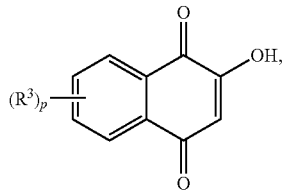

with a compound of the formula:

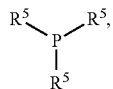

and a compound of the formula:

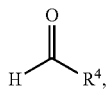

to form a compound of Formula (I-G) is carried out in the presence of an acid. In certain embodiments, the acid is a carboxylic acid. In certain embodiments, the acid is trifluoroacetic acid (TFA). In certain embodiments, the step of contacting is carried out in the presence of a solvent.

In certain embodiments, the method of preparing a compound of Formula (I) comprises contacting a compound of the formula:

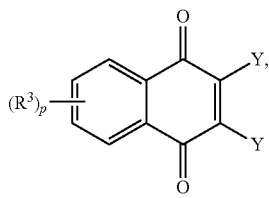

or a salt thereof, with a compound of formula:

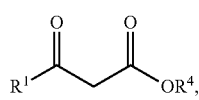

or salt thereof, under conditions sufficient to form a compound of Formula (I-F):

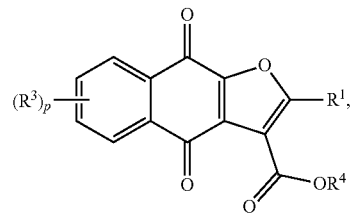

or a salt thereof, wherein $R^1$, $R^3$, $R^4$, and p are as defined herein; and each instance of Y is independently a halogen or a leaving group.

In certain embodiments, the step of contacting a compound of the formula:

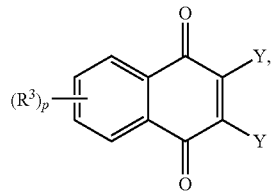

with a compound of formula:

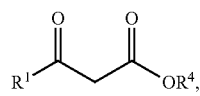

to form a compound of Formula (I-F) is carried out in the presence of a base. In certain embodiments, the base is carbonate. In certain embodiments, the base is sodium carbonate, lithium carbonate, potassium carbonate, or calcium carbonate. In certain embodiments, the base is potassium carbonate ($K_2CO_3$). In certain embodiments, the step of coupling is carried out in the presence of a solvent. In certain embodiments, the solvent is acetonitrile.

As generally defined herein, each instance of Y is independently halogen or a leaving group. In certain embodiments, at least one instance of Y is halogen. In certain embodiments, at least one instance of Y is a leaving group. In certain embodiments, at least one instance of Y is —Cl. In certain embodiments, at least one instance of Y is —Br. In certain embodiments, at least one instance of Y is —F. In certain embodiments, at least one instance of Y is —I. In certain embodiments, each instance of Y is —Cl.

The synthetic schemes and synthetic steps provided are not limiting, and the disclosure contemplates methods wherein additional steps are added, existing steps are omitted or substituted, starting materials or reagents are modified or substituted, or the order of steps is altered. For example, for certain functional groups, additional protection or deprotection steps may be necessary or desired to maintain compatibility with certain reactions or reagents.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Example 1: Preparation of Exemplary MCM Inhibitory Compounds

The compounds provided herein can be prepared from readily available starting materials using methods known in the art, such as the methods described in Mauger et al., *Eur. Pat. Appl.*, 1746097, 24 Jan. 2007, and the methods described in Nitsche et al., *Journal of Medicinal Chemistry*, 56(21), 8389-8403; 2013. Where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

The reactions were generally performed in flame-dried glassware under a positive pressure of nitrogen. Commercial grade reagents and solvents were used without further purification. $CH_2Cl_2$, $CH_3CN$ and THF were purified by PS-MD-5 solvent purification system (Innovative Technology, Inc). Magnetic bead was purchased from TAN Beads, Taiwan. The progress of all the reactions were monitored by TLC, using TLC glass plates precoated with silica gel 60 $F_{254}$ (Merck). Flash column chromatography was performed with silica gel Geduran® Si 60 (Merck). IR spectra were recorded with Thermo Nicolet iS-5 FT-IR spectrophotometer, $V_{max}$ in $cm^{-1}$. $^1H$ and $^{13}C$ NMR spectra were recorded with Bruker AV-III 400 MHz or Bruker AV-400 MHz spectrometers and chemical shifts were measured in δ (ppm) with residual solvent peaks as internal standards ($CDCl_3$, δ 7.24 ppm in $^1H$ NMR, δ 77.0 ppm in $^{13}C$ NMR; $CD_3OD$, δ 3.31 ppm in $^1H$ NMR, δ 49.0 ppm in $^{13}C$ NMR). Coupling constants J, measured in Hz. HR FAB (LR FAB) and HR EI (LR EI)-mass spectra were recorded on a JMS-700 double focusing mass spectrometer (JEOL, Tokyo, Japan) with a resolution of 8000(3000) (5% valley definition) and HR (LR) ESI (Electrospray)-mass spectra were recorded using dual ionization ESCi® (ESI/APCi) source options, Waters LCT premier XE (Waters Corp., Manchester, UK). Melting points were recorded on Büchi M-565 apparatus.

Scheme 2.

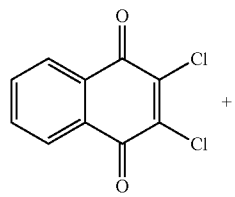

+

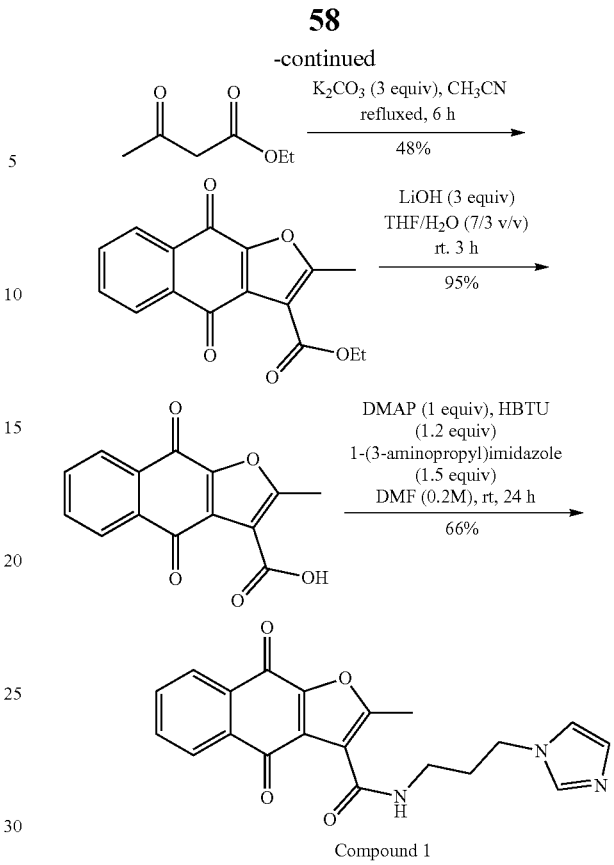

Compound 1

(1) Ethyl 2-Methyl-4, 9-dioxo-4, 9-dihydronaphtho [2, 3-b] furan-3-carboxylate

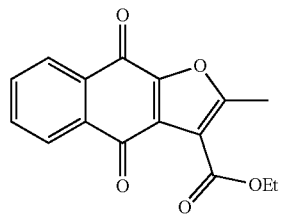 [SMILES: CCOC(=O)c1c(C)oc2c1C(=O)c1ccccc1C2=O]

A mixture of 2, 3-dichloro-1, 4-naphthoquinone (500 mg, 2.20 mmol), $K_2CO_3$ (760 mg, 5.51 mmol) and ethyl acetoacetate (0.31 mL, 2.42 mmol) in MeCN (30 mL) was stirred at reflux temperature for 6 hr. After completion, the reaction mixture was diluted with EtOAc and filtered through Celite®, filtrate was evaporated in vacuo to yield the crude product. The residue was purified by flash column chromatography (EtOAc/hexanes, 1/4 to 2/3) to give 1 as a yellow solid (305 mg, 48% yield). $R_f$ (30% EtOAc/hexanes) 0.52; Mp 149.3-159.9° C.; $^1H$ NMR (400 MHz, $CDCl_3$) δ 8.42-7.99 (m, 2H), 7.98-7.53 (m, 2H), 4.43 (q, J=7.2 Hz, 2H), 2.70 (s, 3H), 1.43 (t, J=7.1 Hz, 3H); $^{13}C$ NMR (100 MHz, $CDCl_3$) δ 178.7, 173.5, 164.4, 162.0, 151.3, 134.1, 133.7, 133.6, 131.5, 128.2, 127.4, 126.5, 113.8, 61.5, 14.2, 14.2.

Exemplary syntheses of compounds of Formula (I), as depicted in Schemes 1 and 2 above, are also described in Hu et al, Synthesis (10):1605-1610 (2005).

(2) 2-Methyl-4, 9-dioxo-4, 9-dihydronaphtho [2, 3-b] furan-3-carboxylic acid

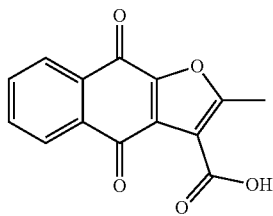 [SMILES: Cc1oc2c(c1C(=O)O)C(=O)c1ccccc1C2=O]

To a stirred solution of ethyl 2-Methyl-4, 9-dioxo-4, 9-dihydronaphtho [2, 3-b]furan-3-carboxylate (378 mg, 1.33 mmol) in THF/H$_2$O (0.2 M, 7/3 v/v) was added LiOH (167 mg, 3.99 mmol) at room temperature. After stirred at room temperature for 3 hr, the reaction mixture was quenched with 1N HCl (adjust to pH ~1, aqueous layer will shows transparent), extracted with EtOAc (15 mL×3), dried over Na$_2$SO$_4$, and concentrated in vacuo. The residue was purified by flash column chromatography (MeOH/CH$_2$Cl$_2$, 0/100 to 1/9) to give 2 as a yellow solid (324 mg, 95% yield). R$_f$ (5% MeOH/CH$_2$Cl$_2$) 0.35; IR (neat) 3425, 3022, 2975, 2920, 2712, 1744, 1673, 1581, 1413, 1217, 1192, 995, 721 cm$^{-1}$; $^1$H NMR (400 MHz, CDCl$_3$) δ 8.25 (td, J=7.4, 1.2 Hz, 2H), 7.84 (dtd, J=18.8, 7.5, 1.3 Hz, 2H), 2.88 (s, 3H); $^{13}$C NMR (100 MHz, CDCl$_3$) δ 184.9, 172.4, 169.0, 160.9, 150.9, 135.8, 134.5, 131.8, 131.7, 128.0, 127.5, 126.0, 112.8, 14.5.

Exemplary syntheses of compounds of Formula (I), as depicted in Schemes 1 and 2 above, is also described in Reynolds et al, *J. Org. Chem.*, 30(11):3819-3824 (1965).

(3) N-(2-Azidoethyl)-2-methyl-4, 9-dioxo-4, 9-dihydronaphtho [2, 3-b] furan-3-carboxamide

3

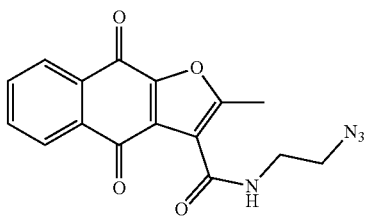

To a stirred solution of 2-Methyl-4, 9-dihydronaphtho [2, 3-b] furan-3-carboxylic acid (25.6 mg, 0.1 mmol), HBTU (45.5 mg, 0.12 mmol) and DMAP (12.2 mg, 0.1 mmol) in DMF (0.5 mL) was added 2-azidoethanamine (25 μL, 0.3 mmol) at room temperature. The solvent was removed by vacuo after the reaction mixture was stirred at room temperature for 4 days. Then the crude was washed by H$_2$O, extracted with CH$_2$Cl$_2$ (10 mL×3), dried over Na$_2$SO$_4$, and concentrated in vacuo. The residue was purified by flash column chromatography (MeOH/CH$_2$Cl$_2$, 0/100 to 1/49) to give 3 as a yellow solid (18.3 mg, 57% yield). R$_f$ (CH$_2$Cl$_2$) 0.49; Mp 152.7-162.5° C.; IR (neat) 3245, 2914, 2845, 2090, 1644, 1574, 1210, 991, 713 cm$^{-1}$; $^1$H NMR (400 MHz, CDCl$_3$) δ 9.95 (s, 1H), 8.19 (ddd, J=8.8, 6.3, 3.6 Hz, 2H), 7.98-7.55 (m, 2H), 3.93-3.22 (m, 4H), 2.86 (s, 3H); $^{13}$C NMR (100 MHz, CDCl$_3$) δ 183.0, 173.0, 166.7, 161.6, 151.1, 134.7, 134.2, 132.8, 131.5, 127.8, 126.8, 126.0, 115.0, 50.7, 38.9, 15.0; HRMS (ESI$^+$, TOF) calculated for C$_{16}$H$_{12}$N$_4$NaO$_4$ [M+Na]$^+$ 347.0756, found 347.0757.

(4) N-(3-(1H-Imidazol-1-yl) propyl)-2-methyl-4, 9-dioxo-4, 9-dihydronaphtho [2, 3-b]furan-3-carboxamide (Compound 1 or GRC4583)

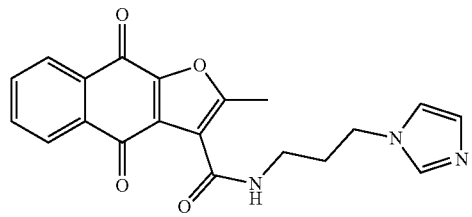 [SMILES: Cc1oc2c(c1C(=O)NCCCn1ccnc1)C(=O)c1ccccc1C2=O]

An exemplary synthesis scheme of Compound 1 is provided below:

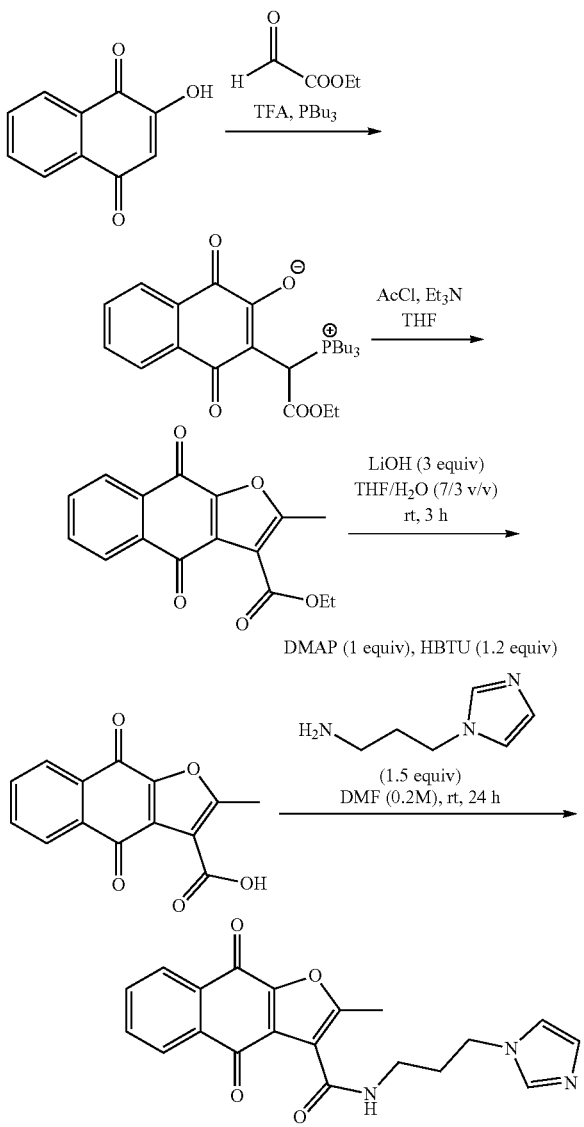

To a stirred solution of 2-Methyl-4, 9-dioxo-4, 9-dihydronaphtho [2, 3-b] furan-3-carboxylic acid (256.2 mg, 1.0 mmol), DMAP (12.2 mg, 0.1 mmol) and HBTU (455 mg, 1.2 mmol) in DMF (5 mL) was added 1-(3-Aminopropyl) imidazole (180 μL, 1.5 mmol) at room temperature. The solvent was removed by vacuo after the reaction mixture was stirred at room temperature for 1 day. Then the crude was washed by $H_2O$, extracted with $CH_2Cl_2$ (10 mL×3), dried over $Na_2SO_4$, and concentrated in vacuo. The residue was purified by flash column chromatography (MeOH/$CH_2Cl_2$, 0/100 to 1/49) to give Compound 1 as a yellow solid (240 mg, 66% yield). $R_f$ (5% MeOH/$CH_2Cl_2$) 0.28; IR (neat) 3285, 3095, 2923, 2848, 1650, 1582, 1213, 991, 844, 715 cm[1]; $^1$H NMR (400 MHz, $CDCl_3$) δ 9.79 (s, 1H), 8.21 (qd, J=4.0, 1.7 Hz, 2H), 7.83-7.76 (m, 2H), 7.59 (s, 1H), 7.07 (s, 1H), 7.00 (s, 1H), 4.11 (t, J=7.0 Hz, 2H), 3.46 (dd, J=12.5, 6.2 Hz, 2H), 2.87 (s, 3H), 2.16 (quint, J=6.8 Hz, 2H); $^{13}$C NMR (100 MHz, $CDCl_3$) δ 183.3, 172.9, 166.5, 161.5, 151.1, 137.2, 134.8, 134.2, 132.7, 131.4, 129.3, 127.8, 126.9, 125.9, 118.9, 115.1, 44.5, 36.2, 30.9, 14.9; HRMS (ESI$^+$, TOF) calculated for $C_{20}H_{18}N_3O_4[M+H]^+$ 364.1297, found 364.1289.

(5) N-(2-(1H-imidazol-1-yl) ethyl)-2-methyl-4, 9-dioxo-4, 9-dihydronaphtho [2, 3-b]furan-3-carboxamide (Compound 5)

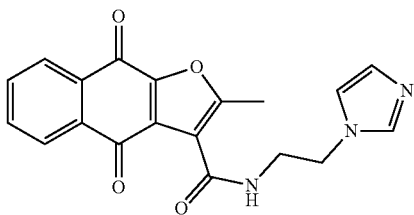 [SMILES: Cc1oc2c(c1C(=O)NCCn1ccnc1)C(=O)c1ccccc1C2=O]

To a stirred solution of 2-Methyl-4, 9-dioxo-4, 9-dihydronaphtho [2, 3-b] furan-3-carboxylic acid (44 mg, 0.17 mmol), DMAP (21 mg, 0.17 mmol) and HBTU (97 mg, 0.26 mmol) in DMF (0.85 mL) was added 2-Imidazol-1yl-ethylamine (47 mg, 0.43 mmol) at room temperature. The solvent was removed by vacuo after the reaction mixture was stirred at room temperature for 1 day. Then the crude was washed by $H_2O$, extracted with $CH_2Cl_2$ (10 mL×3), dried over $Na_2SO_4$, and concentrated in vacuo. The residue was purified by flash column chromatography (MeOH/$CH_2Cl_2$, 0/100 to 1/49) to give compound 5 as a yellow solid (42 mg, 70% yield). $R_f$ (5% MeOH/$CH_2Cl_2$) 0.28; $^1$H NMR (400 MHz, $CD_3OD$) δ 8.27-8.14 (m, 3H), 7.92-7.81 (m, 2H), 7.43 (s, 1H), 7.22 (s, 1H), 4.41 (t, J=6.0 Hz, 1H), 3.86 (t, J=6.0 Hz, 1H), 2.77 (s, 3H); $^{13}$C NMR (100 MHz, $CD_3OD$) δ 184.0, 174.2, 167.1, 163.7, 152.6, 138.8, 135.9, 135.4, 134.2, 132.9, 129.3, 128.6, 127.5, 127.2, 120.8, 115.8, 47.2, 41.3 14.7; HRMS (ESI$^+$, TOF) calculated for $C_{19}H_{16}N_3O_4$ $[M+H]^+$ 350.1141, found 350.1135.

(6) N-(4-(1H-imidazol-1-yl)butyl)-2-methyl-4,9-dioxo-4,9-dihydronaphtho[2,3-b]furan-3-carboxamide (Compound 13)

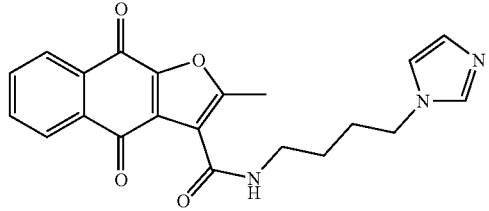 [SMILES: Cc1oc2c(c1C(=O)NCCCCn1ccnc1)C(=O)c1ccccc1C2=O]

To a stirred solution of 2-Methyl-4, 9-dioxo-4, 9-dihydronaphtho [2, 3-b] furan-3-carboxylic acid (95 mg, 0.37 mmol), DMAP (45 mg, 0.37 mmol) and HBTU (154 mg, 0.41 mmol) in DMF (1.9 mL) was added 4-(1H-imidazol-1-yl)butan-1-amine (77 mg, 0.56 mmol) at room temperature. The solvent was removed by vacuo after the reaction mixture was stirred at room temperature for 18 hr. Then the crude was washed by $H_2O$, extracted with $CH_2Cl_2$ (10 mL×3), dried over $Na_2SO_4$, and concentrated in vacuo. The residue was purified by flash column chromatography (MeOH/$CH_2Cl_2$, 0/100 to 1/49) to give compound 13 as a yellow solid (97 mg, 70% yield). $R_f$ (5% MeOH/$CH_2Cl_2$) 0.25; Mp 158.6-164.1° C.; $^1$H NMR (400 MHz, $CDCl_3$) δ 9.70 (s, 1H), 8.18 (d, J=7.5 Hz, 2H), 7.83-7.75 (m, 2H), 7.49 (s, 1H), 7.03 (s, 1H), 6.93 (s, 1H), 4.01 (t, J=7.1 Hz, 2H), 3.47 (dd, J=12.6, 6.4 Hz, 2H), 2.86 (s, 3H), 1.94 (dt, J=15.1, 7.4 Hz, 2H), 1.69 (dt, J=14.2, 6.9 Hz, 2H); $^{13}$C NMR (100 MHz, $CDCl_3$) δ 183.1, 172.8, 166.4, 161.3, 151.0, 137.0, 134.7, 134.1, 132.7, 131.4, 129.3, 127.6, 126.7, 125.9, 118.7, 115.2, 46.6, 38.5, 28.5, 26.4, 14.9; HRMS (ESI$^+$, TOF) calculated for $C_{21}H_{20}N_3O_4$ $[M+H]^+$ 378.1454, found 378.1448.

(7) N-(3-(1H-imidazol-1-yl)propyl)-2-ethyl-4,9-dioxo-4,9-dihydronaphtho[2,3-b]furan-3-carboxamide (Compound 11)

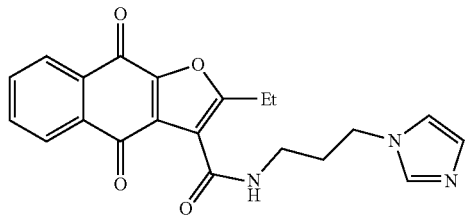 [SMILES: CCc1oc2c(c1C(=O)NCCCn1ccnc1)C(=O)c1ccccc1C2=O]

To a stirred solution of 2-Ethyl-4,9-dioxo-4,9-dihydronaphtho[2,3-b]furan-3-carboxylic acid (92 mg, 0.34 mmol), DMAP (42 mg, 0.34 mmol) and HBTU (142 mg, 0.37 mmol) in DMF (1.7 mL) was added 1-(3-Aminopropyl) imidazole (49 μL, 0.41 mmol) at room temperature. The solvent was removed by vacuo after the reaction mixture was stirred at room temperature for 1 day. Then the crude was washed by $H_2O$, extracted with $CH_2Cl_2$ (10 mL×3), dried over $Na_2SO_4$, and concentrated in vacuo. The residue was purified by flash column chromatography (MeOH/$CH_2Cl_2$, 0/100 to 1/19) to give compound 11 as a yellow solid (116 mg, 90% yield). $R_f$ (5% MeOH/$CH_2Cl_2$) 0.31; $^1$H NMR (400 MHz, $CDCl_3$) δ 9.82 (s, 1H), 8.26-8.18 (m, 2H), 7.84-7.74 (m, 2H), 7.66 (s, 1H), 7.08 (s, 1H), 7.02 (s, 1H), 4.12 (t, J=7.0 Hz, 2H), 3.46 (dd, J=12.5, 6.2 Hz, 2H), 3.35 (q, J=7.5 Hz, 2H), 2.24-2.10 (m, 2H), 1.36 (t, J=7.5 Hz, 3H); $^{13}$C NMR (100 MHz, CDCl$_3$) δ 183.5, 173.0, 171.2, 161.5, 151.3, 137.3, 134.8, 134.2, 132.8, 131.6, 129.5, 127.8, 126.9, 118.9, 114.4, 44.6, 36.3, 31.0, 22.1, 12.0; HRMS (MALDI$^+$, TOF) calculated for C$_{21}$H$_{20}$N$_3$O$_4$ [M+H]$^+$ 378.1448, found 378.1457.

(8) N-(3-(1H-imidazol-1-yl)propyl)-2-isopropyl-4,9-dioxo-4,9-dihydronaphtho[2,3-b]furan-3-carboxamide (Compound 10)

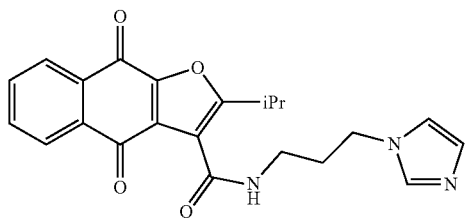 [SMILES: CC(C)c1oc2c(c1C(=O)NCCCn1ccnc1)C(=O)c1ccccc1C2=O]

To a stirred solution of 2-Isopropyl-4,9-dioxo-4,9-dihydronaphtho[2,3-b]furan-3-carboxylic acid (41.8 mg, 0.15 mmol), DMAP (18 mg, 0.15 mmol) and HBTU (61 mg, 0.16 mmol) in DMF (0.74 mL) was added 1-(3-Aminopropyl)imidazole (21 μL, 0.18 mmol) at room temperature. The solvent was removed by vacuo after the reaction mixture was stirred at room temperature for 1 day. Then the crude was washed by H$_2$O, extracted with CH$_2$Cl$_2$ (10 mL×3), dried over Na$_2$SO$_4$, and concentrated in vacuo. The residue was purified by flash column chromatography (MeOH/CH$_2$Cl$_2$, 1/199 to 1/19) to give compound 10 as a yellow solid (52 mg, 90% yield). R$_f$ (5% MeOH/CH$_2$Cl$_2$) 0.32; $^1$H NMR (400 MHz, CDCl$_3$) δ 9.83 (s, 1H), 8.20 (td, J=5.3, 1.8 Hz, 2H), 7.83-7.73 (m, 2H), 7.72 (s, 1H), 7.08 (s, 1H), 7.05 (s, 1H), 4.34-4.27 (m, 1H), 4.14 (t, J=7.0 Hz, 2H), 3.46 (dd, J=12.4, 6.2 Hz, 2H), 2.17 (quint, J=6.8 Hz, 2H), 1.37 (s, 3H), 1.36 (s, 3H); $^{13}$C NMR (100 MHz, CDCl$_3$) δ 183.6, 174.1, 172.9, 161.6, 151.3, 134.8, 134.2, 132.8, 131.6, 128.7, 127.7, 126.8, 125.9, 113.5, 44.8, 36.2, 30.9, 27.7, 20.4; HRMS (ESI$^+$, TOF) calculated for C$_{22}$H$_{22}$N$_3$O$_4$ [M+H]$^+$ 392.1610, found 392.1605.

(9) N-(3-(1H-imidazol-1-yl)propyl)-4,9-dioxo-2-phenyl-4,9-dihydronaphtho[2,3-b]furan-3-carboxamide (Compound 9)

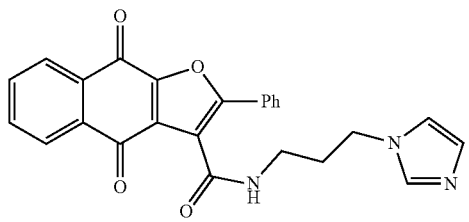

To a stirred solution of 4,9-Dioxo-2-phenyl-4,9-dihydronaphtho[2,3-b]furan-3-carboxylic acid (50.9 mg, 0.16 mmol), DMAP (19.5 mg, 0.16 mmol) and HBTU (73 mg, 0.19 mmol) in DMF (0.8 mL) was added 1-(3-Aminopropyl)imidazole (29 μL, 0.24 mmol) at room temperature. The solvent was removed by vacuo after the reaction mixture was stirred at room temperature for 1 day. Then the crude was washed by H$_2$O, extracted with CH$_2$Cl$_2$ (10 mL×3), dried over Na$_2$SO$_4$, and concentrated in vacuo. The residue was purified by flash column chromatography (MeOH/CH$_2$Cl$_2$, 0/100 to 1/19) to give compound 9 as a yellow solid (38 mg, 56% yield). R$_f$ (5% MeOH/CH$_2$Cl$_2$) 0.32; $^1$H NMR (400 MHz, CDCl$_3$) δ 9.22 (s, 1H), 8.26-8.22 (m, 1H), 8.12-8.10 (m, 1H), 7.92-7.89 (m, 2H), 7.84-7.80 (m, 2H), 7.62 (s, 1H), 7.50-7.44 (m, 3H), 7.06 (s, 1H), 7.01 (s, 1H), 4.14 (t, J=7.0 Hz, 2H), 3.48 (dd, J=12.5, 6.3 Hz, 2H), 2.18 (quint, J=6.8 Hz, 2H); HRMS (ESI$^+$, TOF) calculated for C$_{25}$H$_{20}$N$_3$O$_4$ [M+H]$^+$ 426.1454, found 426.1451.

(10) N-(3-(1H-imidazol-1-yl)propyl)-2-methyl-4,9-dioxo-4,9-dihydro-1H-benzo[f]indole-3-carboxamide (Compound 45)

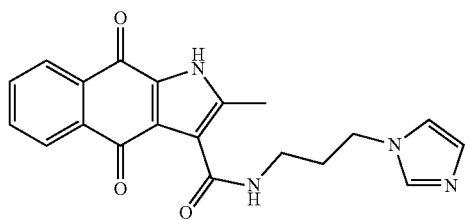 [SMILES: Cc1[nH]c2c(c1C(=O)NCCCn1ccnc1)C(=O)c1ccccc1C2=O]

To a stirred solution of 2-methyl-4,9-dioxo-4,9-dihydro-1H-benzo[f]indole-3-carboxylic acid (23 mg, 0.09 mmol), DMAP (17 mg, 0.14 mmol) and HBTU (51 mg, 0.14 mmol) in DMF (0.45 mL) was added 1-(3-Aminopropyl)imidazole (13 μL, 0.11 mmol) at 0° C. The solvent was removed by vacuo after the reaction mixture was stirred at room temperature for 2 days. The residue was purified by flash column chromatography to give compound 45 as a yellow solid (9.1 mg, 28% yield). R$_f$ (5% MeOH/CH$_2$Cl$_2$) 0.20; $^1$H NMR (400 MHz, CDCl$_3$) δ 10.33 (t, J=5.4 Hz, 1H), 8.24-8.10 (m, 1H), 8.10-7.98 (m, 1H), 7.75-7.63 (m, 2H), 7.60 (s, 1H), 7.00 (s, 1H), 6.99 (s, 1H), 4.10 (t, J=7.1 Hz, 2H), 3.47 (q, J=6.1 Hz, 2H), 2.67 (s, 3H), 2.17-2.05 (m, 2H); HRMS (ESI$^+$, TOF) calculated for C$_{20}$H$_{19}$N$_4$O$_3$ [M+H]$^+$ 363.1457, found 363.1454.

(11) N-(3-(1H-pyrrol-1-yl)propyl)-2-methyl-4,9-dioxo-4,9-dihydronaphtho[2,3-b]furan-3-carboxamide (Compound 12)

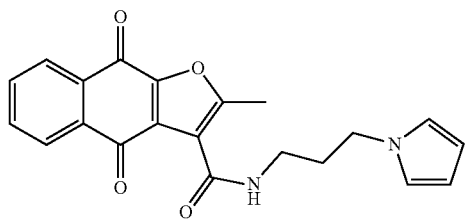 [SMILES: Cc1oc2c(c1C(=O)NCCCn1cccc1)C(=O)c1ccccc1C2=O]

To a stirred solution of 2-Methyl-4, 9-Dioxo-4, 9-dihydronaphtho [2, 3-b] furan-3-carboxylic acid (100 mg, 0.39 mmol), DMAP (47 mg, 0.39 mmol) and HBTU (163 mg, 0.43 mmol) in DMF (1.95 mL) was added 3-(1H-pyrrol-1-yl)propan-1-amine (58 mg, 0.47 mmol) at room temperature. The solvent was removed by vacuo after the reaction mixture was stirred at room temperature for 1 day. Then the crude was washed by H₂O, extracted with CH₂Cl₂ (10 mL×3), dried over Na₂SO₄, and concentrated in vacuo. The residue was purified by flash column chromatography (MeOH/CH₂Cl₂, 0/100 to 1/49) to give compound 12 as a yellow solid (67 mg, 47% yield). $R_f$ (CH₂Cl₂) 0.07; Mp 143.5-150.7° C.; ¹H NMR (400 MHz, CDCl₃) δ 9.73 (s, 1H), 8.26-8.13 (m, 2H), 7.84-7.71 (m, 2H), 6.74 (t, J=2.1 Hz, 2H), 6.14 (t, J=2.1 Hz, 2H), 4.05 (t, J=6.9 Hz, 2H), 3.42 (dd, J=12.3, 6.6 Hz, 2H), 2.86 (s, 3H), 2.14 (quint, J=6.8 Hz, 2H); ¹³C NMR (100 MHz, CDCl₃) δ 183.1, 172.9, 166.5, 161.3, 151.0, 134.7, 134.1, 132.8, 131.5, 127.7, 126.8, 126.0, 120.6, 115.3, 108.2, 47.0, 36.6, 31.2, 14.9; HRMS (MALDI⁺, TOF) calculated for $C_{21}H_{19}N_2O_4$ [M+H]⁺ 363.1339, found 363.1325.

(12) 2-Methyl-N-(3-morpholinopropyl)-4,9-dioxo-4, 9-dihydronaphtho[2,3-b]furan-3-carboxamide (Compound 20)

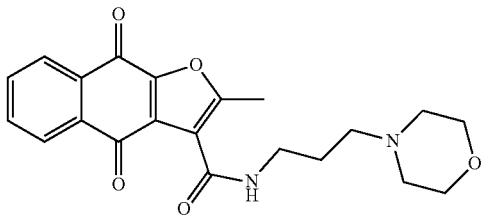 [SMILES: Cc1oc2c(c1C(=O)NCCCN1CCOCC1)C(=O)c1ccccc1C2=O]

To a stirred solution of 2-Methyl-4, 9-dioxo-4, 9-dihydronaphtho [2, 3-b] furan-3-carboxylic acid (23.8 mg, 0.093 mmol), DMAP (17 mg, 0.14 mmol) and HBTU (54 mg, 0.14 mmol) in DMF (0.47 mL) was added 3-morpholinopropylamine (20.4 μL, 0.14 mmol) at 0° C. The solvent was removed by vacuo after the reaction mixture was stirred at room temperature for 2 days. The residue was purified by flash column chromatography (MeOH/CH₂Cl₂, 0/100 to 1/9) to give compound 20 as a yellow solid. ¹H NMR (400 MHz, CDCl₃) δ 9.69 (s, 1H), 8.26-8.14 (m, 2H), 7.83-7.71 (m, 2H), 3.81-3.66 (m, 4H), 3.51 (dd, J=12.5, 6.8 Hz, 2H), 2.87 (s, 3H), 2.60-2.43 (m, 6H), 1.88 (quint, J=7.2 Hz, 2H); HRMS (ESI⁺, TOF) calculated for $C_{21}H_{23}N_2O_5$ [M+H]⁺ 383.1607, found 383.1604.

(13) 2-Methyl-4,9-dioxo-N-(3-(pyrrolidin-1-yl)propyl)-4,9-dihydronaphtho[2,3-b]furan-3-carboxamide (Compound 18)

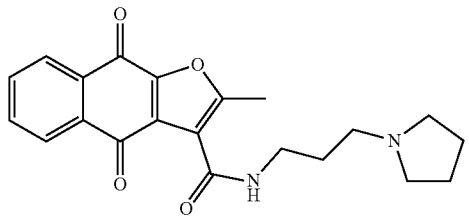 [SMILES: Cc1oc2c(c1C(=O)NCCCN1CCCC1)C(=O)c1ccccc1C2=O]

To a stirred solution of 2-Methyl-4, 9-dioxo-4, 9-dihydronaphtho [2, 3-b] furan-3-carboxylic acid (80 mg, 0.31 mmol), DMAP (57 mg, 0.47 mmol) and HBTU (177 mg, 0.47 mmol) in DMF (1.6 mL) was added 1-(3-Aminopropyl) pyrrolidine (59 μL, 0.60 mmol) at 0° C. The solvent was removed by vacuo after the reaction mixture was stirred at room temperature for 36 hr. The residue was purified by flash column chromatography (MeOH/EtOAc/CH₂Cl₂, 0/1/1 to 1/4/5) to give compound 18 as a yellow solid (47 mg, 41% yield). ¹H NMR (400 MHz, CDCl₃) δ 9.72 (s, 1H), 8.20-8.18 (m, 2H), 7.84-7.68 (m, 2H), 3.51 (dd, J=12.5, 6.7 Hz, 2H), 2.86 (s, 3H), 2.66 (t, J=7.6 Hz, 2H), 2.62 (brs, 4H), 1.96-1.86 (m, 2H); 1.81 (brs, 4H); HRMS (ESI⁺, TOF) calculated for $C_{21}H_{23}N_2O_4$ [M+H]⁺ 367.1658, found 367.1657.

(14) 2-Methyl-4,9-dioxo-N-(4-phenylbutyl)-4,9-dihydronaphtho[2,3-b]furan-3-carboxamide (Compound 17)

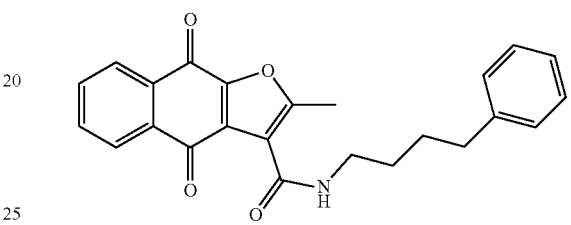

To a stirred solution of 2-Methyl-4, 9-dioxo-4, 9-dihydronaphtho [2, 3-b] furan-3-carboxylic acid (90 mg, 0.35 mmol), DMAP (43 mg, 0.35 mmol) and HBTU (146 mg, 0.39 mmol) in DMF (1.8 mL) was added 4-Phenylbutylamine (72 μL, 0.46 mmol) at 0° C. The solvent was removed by vacuo after the reaction mixture was stirred at room temperature for 20 hr. The residue was purified by flash column chromatography (EtOAc/hexanes, 1/49 to 1/9) to give compound 17 as a yellow solid (78 mg, 58% yield). $R_f$ (20% EtOAc/hexanes) 0.35; Mp 151.4-152.7° C.; ¹H NMR (400 MHz, CDCl₃) δ 9.66 (s, 1H), 8.26-8.11 (m, 2H), 7.87-7.68 (m, 2H), 7.34-7.09 (m, 5H), 3.47 (dd, J=12.2, 6.6 Hz, 2H), 2.87 (s, 3H), 2.69 (t, J=7.3 Hz, 2H), 1.88-1.66 (m, 4H); ¹³C NMR (100 MHz, CDCl₃) δ 182.9, 172.9, 166.3, 161.1, 150.9, 142.2, 134.5, 134.0, 132.8, 131.5, 128.4, 128.2, 127.6, 126.7, 126.0, 125.7, 115.5, 39.2, 35.5, 28.9, 28.8, 14.9; HRMS (ESI⁺, TOF) calculated for $C_{24}H_{21}NO_4Na$ [M+Na]⁺ 410.1368, found 410.1374.

(15) N-(3-(1H-imidazol-1-yl)propyl)-2-methylbenzofuran-3-carboxamide (Compound 44)

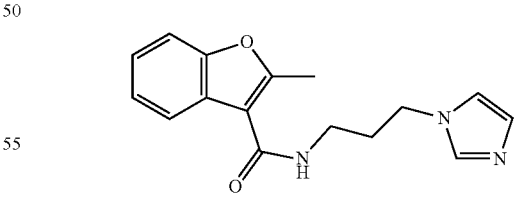

To a stirred solution of 2-methylbenzofuran-3-carboxylic acid (25 mg, 0.14 mmol), DMAP (25.7 mg, 0.21 mmol) and HBTU (80 mg, 0.21 mmol) in DMF (0.7 mL) was added 1-(3-Aminopropyl)imidazole (19 μL, 0.16 mmol) at 0° C. The solvent was removed by vacuo after the reaction mixture was stirred at room temperature for 1 day. The residue was purified by flash column chromatography (MeOH/CH₂Cl₂, 0/100 to 1/9) to give compound 44 as a colorless oil (37 mg, 95% yield). $R_f$ (5% MeOH/CH₂Cl₂) 0.29; ¹H NMR (400 MHz, CDCl$_3$) δ 7.58-7.48 (m, 2H), 7.48-7.41 (m, 1H), 7.32-7.25 (m, 2H), 7.05 (s, 1H), 6.97 (s, 1H), 5.97 (s, 1H), 4.07 (t, J=7.0 Hz, 2H), 3.51 (dd, J=13.1, 6.7 Hz, 2H), 2.71 (s, 3H), 2.15 (quint, J=6.9 Hz, 2H); HRMS (ESI$^+$, TOF) calculated for C$_{16}$H$_{18}$N$_3$O$_2$ [M+H]$^+$ 284.1399, found 284.1392.

(16) N-(3-(1H-imidazol-1-yl)propyl)-4,9-dioxo-2-(trifluoromethyl)-4,9-dihydronaphtho[2,3-b]furan-3-carboxamide (RJ-LC-01-47)

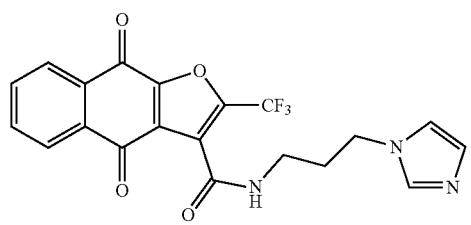 [SMILES: O=C1c2ccccc2C(=O)c2c1oc(C(F)(F)F)c2C(=O)NCCCn1ccnc1]

An exemplary synthetic scheme of Compound RJ-LC-01-47 is provided below:

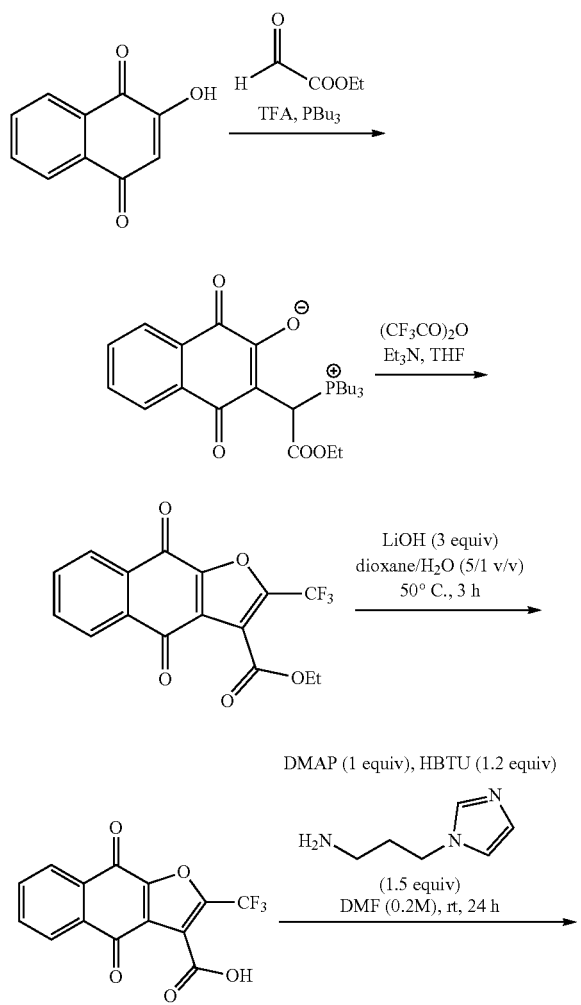

(17) N-(3-(1H-imidazol-1-yl)propyl)-7-fluoro-2-methyl-4,9-dioxo-4,9-dihydronaphtho[2,3-b]furan-3-carboxamide (RJ-LC-07-48)

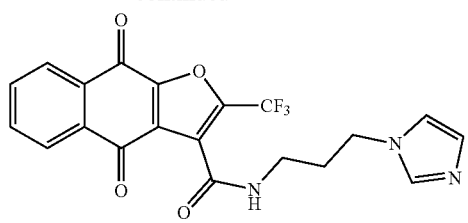

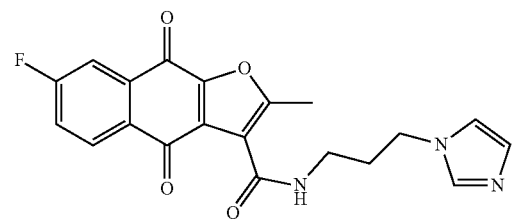 [SMILES: Cc1oc2c(c1C(=O)NCCCn1ccnc1)C(=O)c1ccc(F)cc1C2=O]

An exemplary synthetic scheme of Compound RJ-LC-07-48 is provided below:

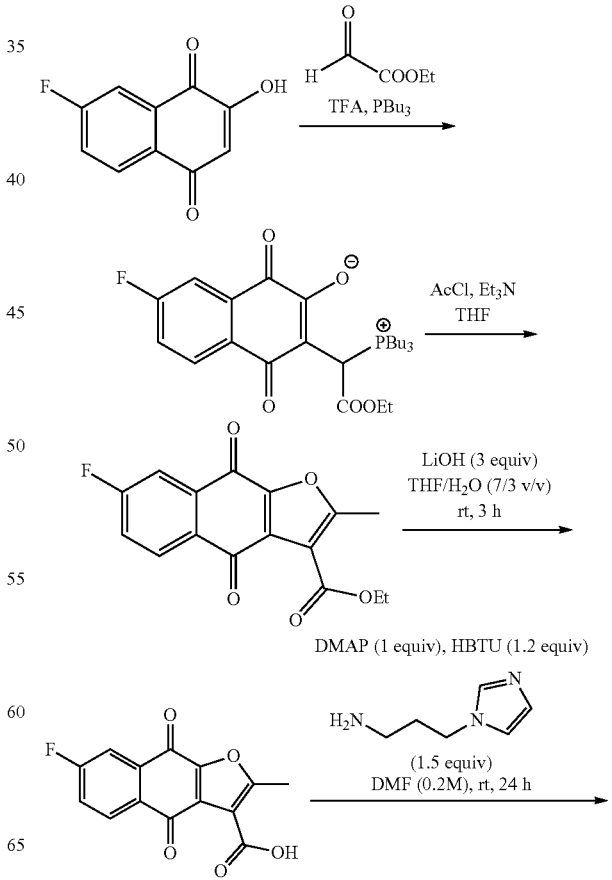

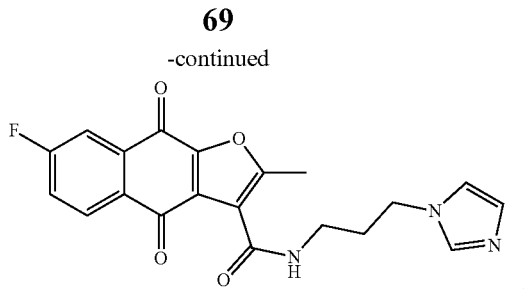

An exemplary synthetic scheme of Compound RJ-LC-07-48 (compound 48) is provided below:

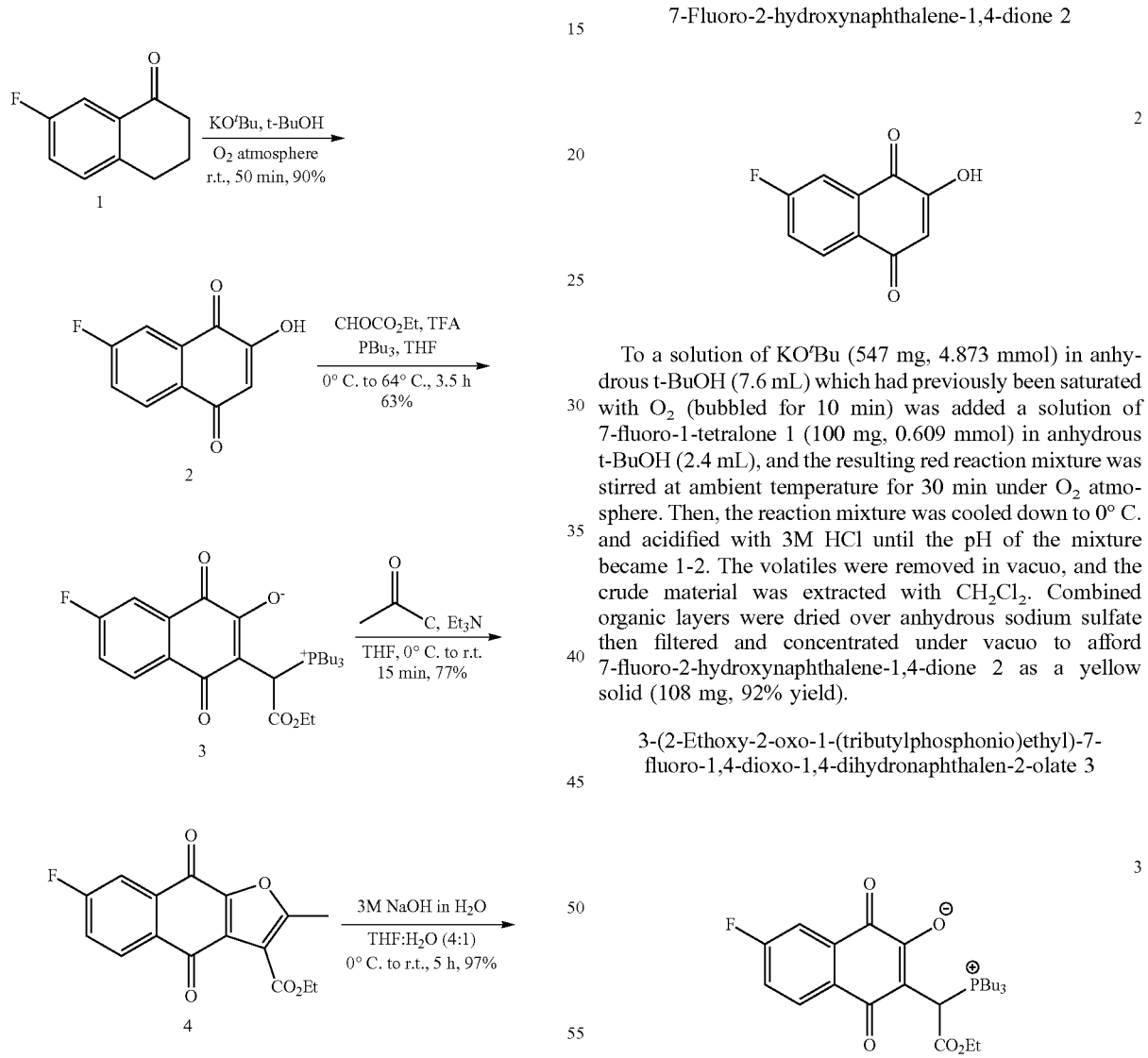

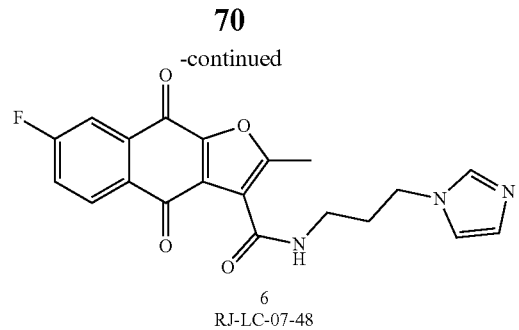

7-Fluoro-2-hydroxynaphthalene-1,4-dione 2

To a solution of KO$^t$Bu (547 mg, 4.873 mmol) in anhydrous t-BuOH (7.6 mL) which had previously been saturated with $O_2$ (bubbled for 10 min) was added a solution of 7-fluoro-1-tetralone 1 (100 mg, 0.609 mmol) in anhydrous t-BuOH (2.4 mL), and the resulting red reaction mixture was stirred at ambient temperature for 30 min under $O_2$ atmosphere. Then, the reaction mixture was cooled down to 0° C. and acidified with 3M HCl until the pH of the mixture became 1-2. The volatiles were removed in vacuo, and the crude material was extracted with $CH_2Cl_2$. Combined organic layers were dried over anhydrous sodium sulfate then filtered and concentrated under vacuo to afford 7-fluoro-2-hydroxynaphthalene-1,4-dione 2 as a yellow solid (108 mg, 92% yield).

3-(2-Ethoxy-2-oxo-1-(tributylphosphonio)ethyl)-7-fluoro-1,4-dioxo-1,4-dihydronaphthalen-2-olate 3

To compound 2 (138 mg, 0.718 mmol) with THF (1.0 ml) in a dry and nitrogen-flushed sealed tube at 0° C. was sequentially added ethyl glyoxalate (50% solution in toluene) (263 µL, 1.8 equiv), trifluoroacetic acid (96 µL, 1.8 equiv) and $Bu_3P$ (210 µL, 1.2 equiv), then the reaction mixture was stirred for 3.5 h at 60-64° C. Solvent was removed under vacuo to obtain the crude, which then purified by flash chromatography in neutral $Al_2O_3$(EtOAc/n-Hexane, 1/1) to provide compound 3 as red gummy liquid (190.0 mg, 63% yield).

Ethyl 7-fluoro-2-methyl-4,9-dioxo-4,9-dihydronaphtho[2,3-b]furan-3-carboxylate 4

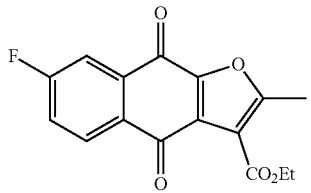

To compound 3 (393 mg, 0.821 mmol) with THF (4.1 ml) in a dry and nitrogen-flushed round bottom flask at 0° C. was slowly added acetyl chloride (76 μL, 1.3 equiv) and Et₃N (171 μL, 1.5 equiv), then stirred for 15 min. Solvent was removed under vacuo to obtain the crude, which then purified by flash chromatography (EtOAc/n-Hexane, 1/9) to provide compound 4 as pale yellow solid (199.0 mg, 61% yield).

7-Fluoro-2-methyl-4,9-dioxo-4,9-dihydronaphtho[2,3-b]furan-3-carboxylic Acid 5

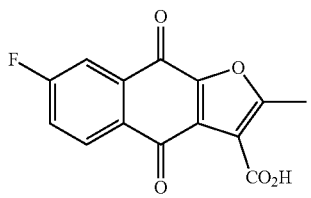

To compound 4 (355 mg, 1.175 mmol) with THF (9.4 mL) and H₂O (2.35 mL) in a round bottom flask at 0° C. was added 3M NaOH$_{(aq)}$ (1.17 ml, 4.5 eq), then allowed to room temperature for a period of 5 hr. Solvent was removed under vacuo then dilute with H₂O and washed with CH₂Cl₂. The aqueous layer was added 3M HCl$_{(aq)}$ until pH=1~2, then extracted with EA and Brine. Combined organic layers were dried over anhydrous sodium sulfate then filtered and concentrated under vacuo to afford the crude carboxylic acid 5 (313 mg, 97% yield).

N-(3-(1H-imidazol-1-yl)propyl)-7-fluoro-2-methyl-4,9-dioxo-4,9-dihydronaphtho[2,3-b]furan-3-carboxamide 6 (RJ-LC-07-48)

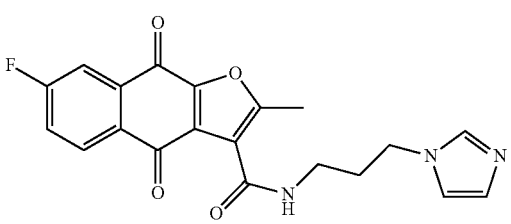

To a solution of carboxylic acid 5 (282 mg, 1.028 mmol) with DMF (10.3 mL) in a round bottom flask at room temperature was added DMAP (126 mg, 1.028 mmol), HBTU (468 mg, 1.234 mmol), 3-(1H-imidazol-1-yl)propan-1-amine (184 μL, 1.542 mmol), then stirred for 6 h. Solvent was removed under vacuo to obtain the crude material, which then purified by flash chromatography (MeOH/CH₂Cl₂, 1/9) to provide product 6 (251 mg, 64% yield).

An exemplary synthetic scheme of Compound RJ-LC-07-49 (compound 49) is provided below:

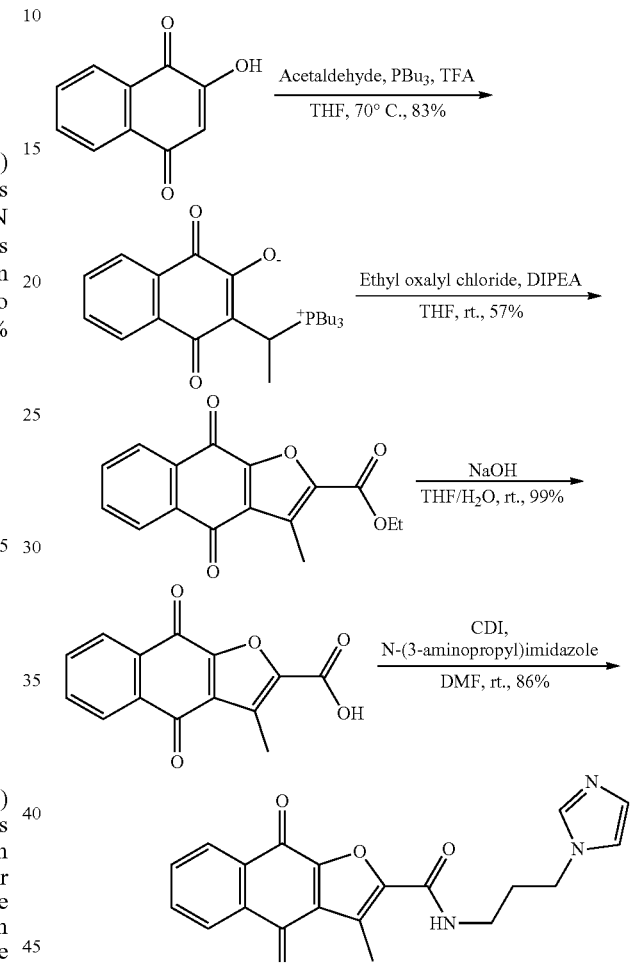

RJ-LC-07-49

1,4-dioxo-3-(1-(tributylphosphonio)ethyl)-1,4-dihydronaphthalen-2-olate

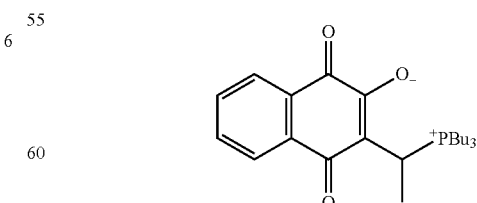

To a dry and N₂-flushed sealed tube equipped with a stir bar was sequentially added 2-hydroxy-naphthoquinone (100 mg, 1 eq.) in dry THF (0.38 M, 1.5 mL), acetaldehyde (240 μL, 7.2 eq.), TFA (160 μL, 1.8 eq.) and tributylphosphine (170 μL, 1.2 eq.). The resulting solution was stirred at 70° C. for 20 h. After completion of the reaction, the crude mixture was concentrated in vacuo and purified by column chromatography (50% EA/hex followed by 1-2% MeOH/DCM) to give a red oil (192 mg, 83%). R$_f$ (100% EA) 0.34. $^1$H NMR (400 MHz, CDCl3) δ 7.92-8.01 (m, 2H), 7.57 (t, J=7.5 Hz, 1H), 7.45 (t, J=7.4 Hz, 1H), 4.16-4.27 (m, 1H), 2.01-2.28 (m, 6H), 1.32-1.55 (m, 15H), 0.85 (t, 9H). $^{13}$C NMR (100 MHz, CDCl3) δ 184.5, 180.5, 170.4, 134.8, 133.6, 131.6, 130.9, 126.1, 125.7, 113.2, 24.3, 24.2, 24.1, 24.0, 20.0, 19.5, 13.3. $^{31}$P NMR (162 MHz, CDCl3) δ 36.4.

Ethyl 3-methyl-4,9-dioxo-4,9-dihydronaphtho[2,3-b]furan-2-carboxylate

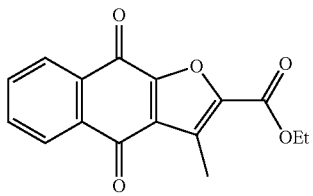 [SMILES: CCOC(=O)c1oc2c(c1C)C(=O)c1ccccc1C2=O]

To a dry and N$_2$-flushed 10 mL Schlenk tube equipped with a stir bar and septum was sequentially added SM (100 mg, 1 eq.) in dry THF (0.14 M, 1.8 mL), dry DIPEA (262 μL, 6 eq.) and ethyl oxalyl chloride (44.7 μL, 1.6 eq.). The resulting solution was stirred at 70° C. for 3 h and after completion of the reaction, the crude mixture was concentrated in vacuo and purified by column chromatography (0-40% DCM/hex) to give a pale yellow solid (40 mg, 57%). R$_f$ (20% EA/hex) 0.55. $^1$H NMR (400 MHz, CDCl3) δ 8.14-8.24 (m, 2H), 7.74-7.79 (m, 2H), 4.44 (q, J=7.2 Hz, 2H), 2.70 (s, 3H), 1.43 (t, J=7.3 Hz, 3H); $^{13}$C NMR (100 MHz, CDCl3) δ 181.1, 173.7, 158.6, 152.1, 144.6, 134.2, 134.0, 133.4, 132.4, 129.8, 128.9, 128.6, 126.9, 61.7, 14.2, 10.0

3-methyl-4,9-dioxo-4,9-dihydronaphtho[2,3-b]furan-2-carboxylic Acid

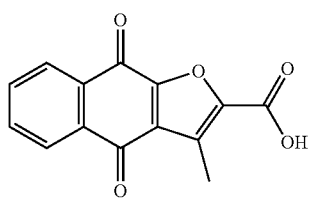 [SMILES: Cc1c(C(=O)O)oc2c1C(=O)c1ccccc1C2=O]

To a test tube equipped with a stir bar and septum was added SM (300 mg, 1 eq.), 7:3 THF/H$_2$O (0.2 M, 0.63 mL) and NaOH (63 mg, 1.5 eq.). The resulting mixture was stirred at R.T for 12 h. After removal of THF in vacuo, the crude mixture extracted with DCM, then discard the organic layers. The aqueous layers was acidified to pH=2 by 1N HCl and extracted with EA, and the combined organic layers were dried over MgSO4, filtered, and concentrated to yield a dark yellow solid (269 mg, 99%). R$_f$ (5% MeOH/DCM, silica) 0.13. $^1$H NMR (400 MHz, d-MeOH/CDCl3) δ 8.11-8.17 (m, 2H), 7.72-7.78 (m, 2H), 2.66 (s, 3H)

N-(3-(1H-imidazol-1-yl)propyl)-3-methyl-4,9-dioxo-4,9-dihydronaphtho[2,3-b]furan-2-carboxamide (RJ-LC-07-49)

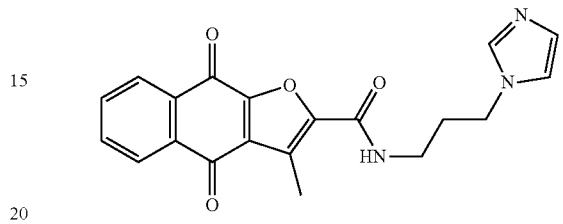

To a dry and N$_2$-flushed 10 mL Schlenk flask equipped with stir bar and septum was added SM (11 mg, 1 eq.) and CDI (11.3 mg, 1.05 eq.) in dry DMF (0.05 M, 0.8 mL) and stirred at room temperature for 30 min. After added N-(3-aminopropyl)imidazole (7.7 μL, 1.5 eq), the reaction mixture was stirred at room temperature for 12 h. After completion of the reaction, the DMF was removed in vacuo and the crude solid was washed with H$_2$O and Et$_2$O separately to remove impurities yield a yellow solid (14 mg, 86%). R$_f$(20% MeOH/CHCl$_3$) 0.52. $^1$H NMR (600 MHz, CDCl3) δ 8.16-8.21 (m, 2H), 7.74-7.80 (m, 2H), 7.56 (s, 1H), 7.04-7.10 (m, 2H), 6.98 (s, 1H), 4.07 (t, J=6.9 Hz, 2H), 3.47-3.51 (q, 6.4 Hz, 2H), 2.75 (s, 3H), 2.13-2.19 (quintet, J=6.8 Hz, 2H); $^{13}$C NMR (150 MHz, CDCl3) δ 181.1, 174.0, 158.7, 150.8, 146.2, 137.3, 134.4, 134.0, 133.5, 132.2, 129.8, 129.7, 127.5, 127.1, 126.8, 118.7, 118.7, 44.6, 36.5, 31.2, 9.75.

Example 2: Characterization of the Exemplary MCM Inhibitory Compounds

Select compounds described herein were evaluated for structure-activity analyses in vitro. The inhibitory activity of the compounds against the H1975 cell line was evaluated by Sulforhodamine B colorimetric (SRB) assay. 2×10$^3$ cells were cultured in 96-well culture plates for 24 hours before use in the experiment. The culture medium was replaced with fresh medium containing the appropriate concentration of compound ranging from 0.005 μM to 10 μM for 72 hours. After an incubation period, the cells were fixed with 10% trichloroacetic acid and stained for 30 min, after which the excess dye was removed by washing repeatedly with 1% acetic acid. The protein-bound dye was dissolved in 10 mM Tris base solution for OD determination at 510 nm using a microplate reader.

TABLE 1

IC$_{50}$ values and toxicity data of exemplary compounds described herein.

| Compound | Structure | IC$_{50}$ (nM) |
|---|---|---|
| 1 | 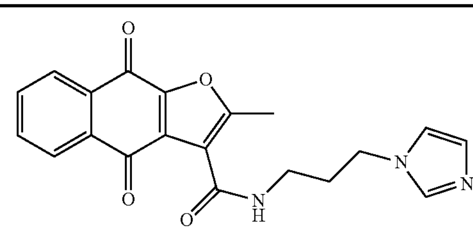 | 77-247 |

TABLE 1-continued

IC$_{50}$ values and toxicity data of exemplary compounds described herein.

| Compound | Structure | IC$_{50}$ (nM) |
|---|---|---|
| 5 | 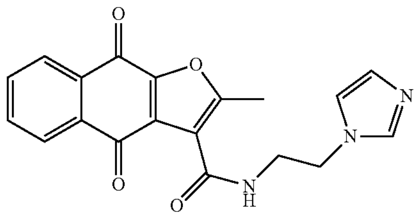 [SMILES: Cc1oc2c(c1C(=O)NCCn1ccnc1)C(=O)c1ccccc1C2=O] | 280 |
| 9 | 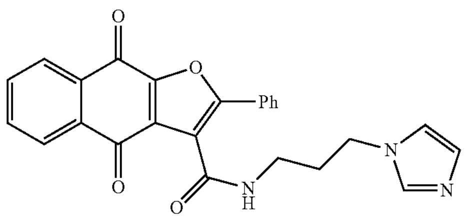 | 826 |
| 10 | 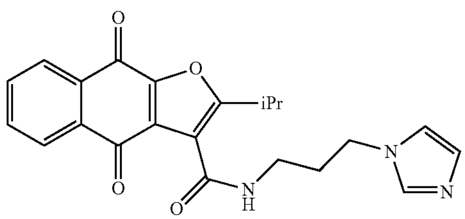 [SMILES: CC(C)c1oc2c(c1C(=O)NCCCn1ccnc1)C(=O)c1ccccc1C2=O] | 260 |
| 11 | 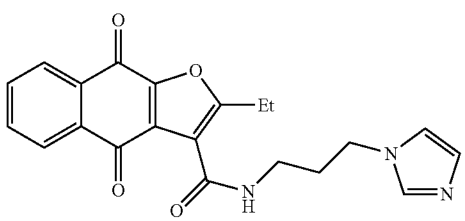 [SMILES: CCc1oc2c(c1C(=O)NCCCn1ccnc1)C(=O)c1ccccc1C2=O] | 288 |
| 12 | 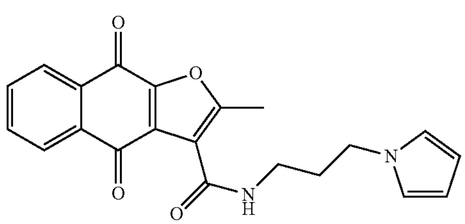 [SMILES: Cc1oc2c(c1C(=O)NCCCn1cccc1)C(=O)c1ccccc1C2=O] | 918 |
| 13 | 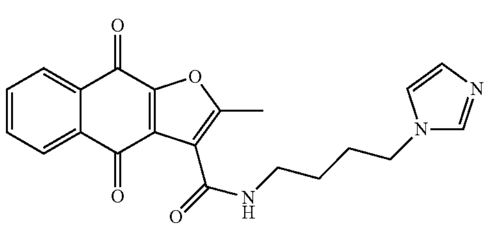 [SMILES: Cc1oc2c(c1C(=O)NCCCCn1ccnc1)C(=O)c1ccccc1C2=O] | 250 |

TABLE 1-continued

IC$_{50}$ values and toxicity data of exemplary compounds described herein.

| Compound | Structure | IC$_{50}$ (nM) |
|---|---|---|
| 17 | naphtho-furan-dione with CONH-(CH$_2$)$_3$-phenyl | >10,000 |
| 18 | naphtho-furan-dione with CONH-(CH$_2$)$_3$-pyrrolidinyl | 24 |
| 20 | naphtho-furan-dione with CONH-(CH$_2$)$_3$-morpholinyl | 80 |
| 45 | naphtho-indole-dione with CONH-(CH$_2$)$_3$-imidazolyl | 8727 |

(I) Assay of Effect on Cell Cycle Progression, by Exemplary Compounds Described Herein The effect of compound 1 on cell cycle progression in several lung cancer cell lines was determined. Panel (A) of FIG. 1 shows the structure of compound 1. Exemplary results of a cytotoxicity assay and cell cycle analysis are shown in Panel (B) of FIG. 1 and Tables 2-3, respectively. Compound 1 demonstrated inhibition of growth of both gefitinib-sensitive and gefitinib-resistant lung cancer cells, with an IC$_{50}$ of less than 300 nM and at least a 3-fold higher potency for cancer cells than normal cells. (Panel (B) of FIG. 1 and Table 2). For IC$_{50}$ determination, 2×10$^3$ cells were seeded in 96-well culture plates for 24 h before use in the experiment. The cells were then treated with the appropriate concentrations of compound ranging from 0.005 µM to 10 µM for 72 h. After an incubation period, the cells were fixed with 10% trichloroacetic acid and stained for 30 min, after which the excess dye was removed by washing repeatedly with 1% acetic acid. The protein-bound dye was dissolved in 10 mM Tris base solution for OD determination at 510 nm using a microplate reader. The cell growth curve was plotted using GraphPad software. For cell cycle analysis, H1975 cells were seeded at a density of 5×10$^4$ in 60-mm culture dishes for 24 h before use in the experiment. The cells were treated with 0-140 nM of compound for 72 h in complete medium. The cells were harvested by 0.1% trypsin solution containing 0.05% EDTA in phosphate-buffered saline (PBS, 0.01 M sodium phosphate, 0.14 M NaCl, pH 7.4) (Sigma), centrifuged, washed in PBS, and resuspended in cold 70% ethanol. The cells were then stained with propidium iodide (Sigma) for 30 min and subjected to flow cytometric analysis on a FACStar Plus (Becton Dickinson, San Francisco, Calif.). When H1975 cells were treated with 140 nM compound 1 for 72 h, a significant number of cells were arrested in the S (18% of compound treated vs. 2% of the control group) and G2-M (38% of compound treated vs. 17% of the control group) phases of the cell cycle. (Table 3).

TABLE 2

IC$_{50}$ of compound 1 in different lung cancer and normal cell lines.

| Cell line | IC$_{50}$ (µM) |
|---|---|
| PC9 (human lung adenocarcinoma cells, EGFR del 19 mutation and sensitive to gefitinib) | 0.037 |
| PC9/IR (human lung adenocarcinoma cells, EGFR del 19 mutation but resistant to gefitinib) | 0.048 |

TABLE 2-continued

IC$_{50}$ of compound 1 in different lung cancer and normal cell lines.

| Cell line | IC$_{50}$ (μM) |
| --- | --- |
| CL1-0 (human lung adenocarcinoma cells, EGFR wild type and resistant to gefitinib) | 0.123 |
| CL1-5 (human lung adenocarcinoma cells, EGFR wild type and resistant to gefitinib) | 0.280 |
| A549 (adenocarcinomic human alveolar basal epithelial cells, EGFR wild type and resistant to gefitinib) | 0.053 |
| H1975 (non-small cell lung cancer cells, EGFR L858R and T790M mutation and resistant to gefitinib) | 0.077 |
| HS68 (human foreskin fibroblast cells, used as normal cells) | >1 |

TABLE 3

Cell cycle analysis and quantification of H1975 cells treated with Compound 1 for 72 h at different dosages.

| Conc. (nM) | Phase (%) | | | |
| --- | --- | --- | --- | --- |
| | subG1 | G1 | S | G2/M |
| 0 | 5 | 79 | 2 | 17 |
| 35 | 1 | 70 | 4 | 23 |
| 70 | 1 | 58 | 7 | 31 |
| 140 | 4 | 39 | 18 | 38 |

(II) In Vivo and In Vitro Effect of Exemplary Compounds Described Herein

To evaluate the anti-lung cancer potency of compound 1 in vivo (Ahn, et al. (2010), Molecular Cancer Therapeutics, 9(11):2859-2868), athymic nude mice that bear established subcutaneous H1975 tumors were daily treated intraperitoneal with compound at 1 mg/kg or 4 mg/kg in 50% PEG400 versus DMSO control for 4 weeks. Exemplary results are shown in Panel (C) of FIG. 1. Treatment with compound 1 at a dose of 1 mg/kg and 4 mg/kg shows inhibition of H1975 xenograft tumor growth to a greater degree, compared to the effects of the treatment with the DMSO control (average tumor size, 1,217±516.6 mm$^3$ for DMSO, 701.2±196.5 mm$^3$ for 1 mg/kg and 518.0±93.0 mm$^3$ for 4 mg/kg on day 27, p<0.05). (Panel (C) of FIG. 1). In addition, the body weight of the mice was calculated when the tumor size was measured. Serum was also collected, and biological analysis in vitro was performed. Few differences between the control group and compound treatment group were observed. Inhibition of tumor growth of Compound 1 with low cytotoxicity in vivo was observed. The results showed that tumor size of compound 1-treated mice was reduced compared to that of the control mice (right panel of panel (C) in FIG. 1, 6 mice per group; original magnification, ×400).

(III) Effects on DNA Replication by Exemplary Compounds Described Herein

Figure 2:
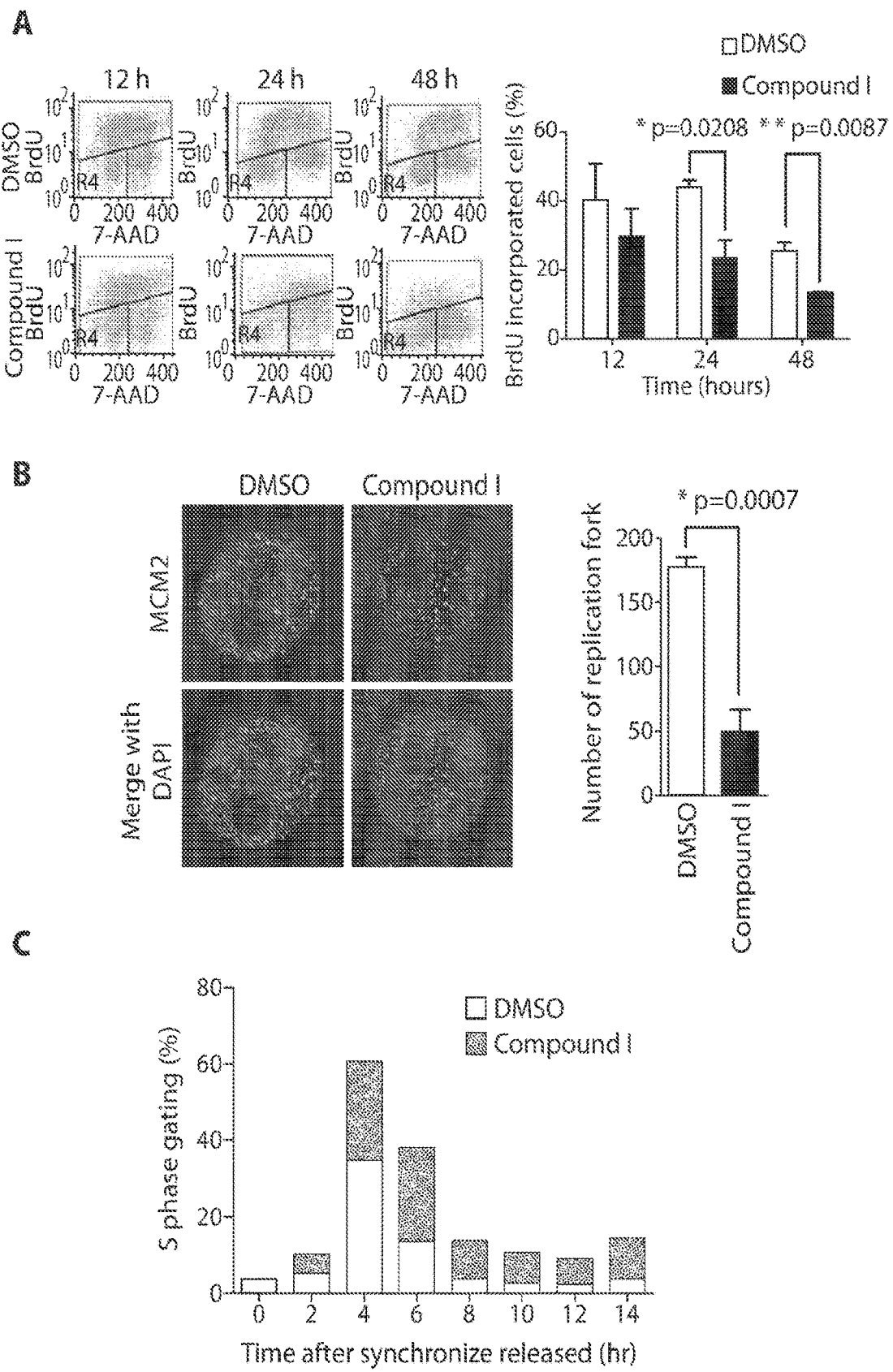
FIG. 2 shows exemplary results for the interruption of DNA replication by compound 1. Panel (A): A chart showing DNA replication in Compound 1-treated H1975 cells was inhibited. DNA histograms (BrdU incorporation vs. DNA content) of DMSO or compound 1-treated H1975 cells are shown at 12 to 48 hours. The H1975 cells were BrdU-pulsed (BD Pharmingen™ BrdU Flow Kit Staining) and analyzed by flow cytometry. Panel (B): A chart showing compound 1 decreased the replication fork number. The replication forks were analyzed by immunofluorescence staining with anti-MCM2 antibodies (see row labeled "MCM2" and "Merge with DAPI") and DAPI (see row labeled "Merge with DAPI"). The quantification was made by counting signals obtained with the anti-MCM2 antibody using Image J software. (n=5 cells per group; original magnification, ×1000). Panel (C): A chart showing compound 1-treated H1975 cells have a prolonged S phase. A double thymidine block was performed, and the data were collected at the indicated time points.

To evaluate the effects on DNA replication of Compound 1, the levels of BrdU (5'-bromo'-2'-deoxyuridine) incorporation were examined. Exemplary results are shown in Panel (A) of FIG. 2. For BrdU (5'-Bromo-2'-deoxyuridine) labeling, the cells were pre-cultured for 24 hours, treated for 12, 24, or 48 h and pulse labeled for 30 minutes with 10 μM BrdU (BioVision, Inc., Milpitas, Calif.). Cells were fixed and permeabilized with Cytofix/Cytoperm Buffer (BD Pharmingen™ BrdU Flow Kit Staining, BD Bioscience, San Jose, Calif.) and treated with DNase to expose incorporated BrdU. The content of BrdU was assessed using fluorescent antibodies. DNA was stained with 7-AAD. The samples were analyzed in a FACS caliber flow cytometer (Becton Dickinson, Sweden) for dot plot histogram analysis (BrdU incorporation vs. DNA content). The percentages of BrdU-positive cells in the treated group were lower than those in the DMSO control group (Panel (A) of FIG. 2).

In addition, to evaluate the effects of compound 1 on the progression of DNA replication, the number of replication forks was determined by MCM2 immunofluorescence staining in H1975 cells released from the G1 phase with DMSO and with compound 1 treatment. Exemplary results are shown in Panel (B) of FIG. 2. To evaluate the effects on DNA replication of compound 1, H1975 cells were arrested in G1 by contact inhibition. After 3 days, the cells were re-plated at a low density on cover slips and allowed to progress through the cell cycle. The cells were pulsed with 140 nM compound for 48 h and were fixed for 10 minutes at room temperature in 3.7% cold paraformaldehyde in PBS (pH 7.2), washed 3 times with PBS, and permeabilized for 10 minutes at room temperature in PBS containing 0.1% Triton X-100. The cells were blocked with PBS containing 3% bovine serum albumin and stained overnight at 4° C. with primary antibodies against MCM2, followed by incubation for 1 hour at 37° C. with Alexa Fluor 488 Goat Anti-Mouse IgG (Life Technologies Corporation), respectively. The cells were mounted onto microscope slides with ProLong Gold Antifade Reagent with DAPI (4',6-Diamidino-2-phenylindole dihydrochloride) (Life Technologies Corporation) and then examined and photographed using Zeiss LSM 700 Confocal (Zeiss, Urbana, Ill.). Fewer replication forks existed in the compound 1-treated group (number of the replication fork, 176.8±8.721 of compound treated vs. 48.80±18.66 of the control group, p=0.0007). (Panel (B) of FIG. 2)

To evaluate the effects of compound 1 on a single round of DNA replication in a cell cycle, H1975 cells were synchronized using a double thymidine block followed by release with DMSO or compound 1-containing medium for 2 to 14 hours. Exemplary results are shown in Panel (C) of FIG. 2. H1975 cells were grown to 60-70% confluence. Then, 2 mM thymidine (Sigma) was added to the cells and incubated for 17 hours. The cells were then washed, and fresh serum-containing medium was added. After 10 hours, thymidine was added again, and the cells were incubated for 17 hours; the cells were then washed with PBS, replaced with fresh serum-containing medium, and the data were collected at the indicated time points. Through flow cytometry analysis, the control cells were observed as synchronized in the G0-G1 phase from 0 hours, increased in the S phase from 4 to 6 hours, and finally progressed to the G2 phase after 8 hours. However, many of the compound 1-treated cells remained in the S phase at all time points. (Panel (C) of FIG. 2). A double thymidine block was performed and the data were collected at the indicated time points. Compared to DMSO, compound 1-treated H1975 cells required more time for the S phase (approximately 4 hours).

(IV) Effects on MCM2-7 Ubiquitination and Degradation in Lung Cancer Cells by Exemplary Compounds Described Herein To evaluate the effects of Compound 1 on modulating the expression of different MCM protein components, immunoblotting of DMSO or compound 1-treated (at 140 nM)

Figure 3:
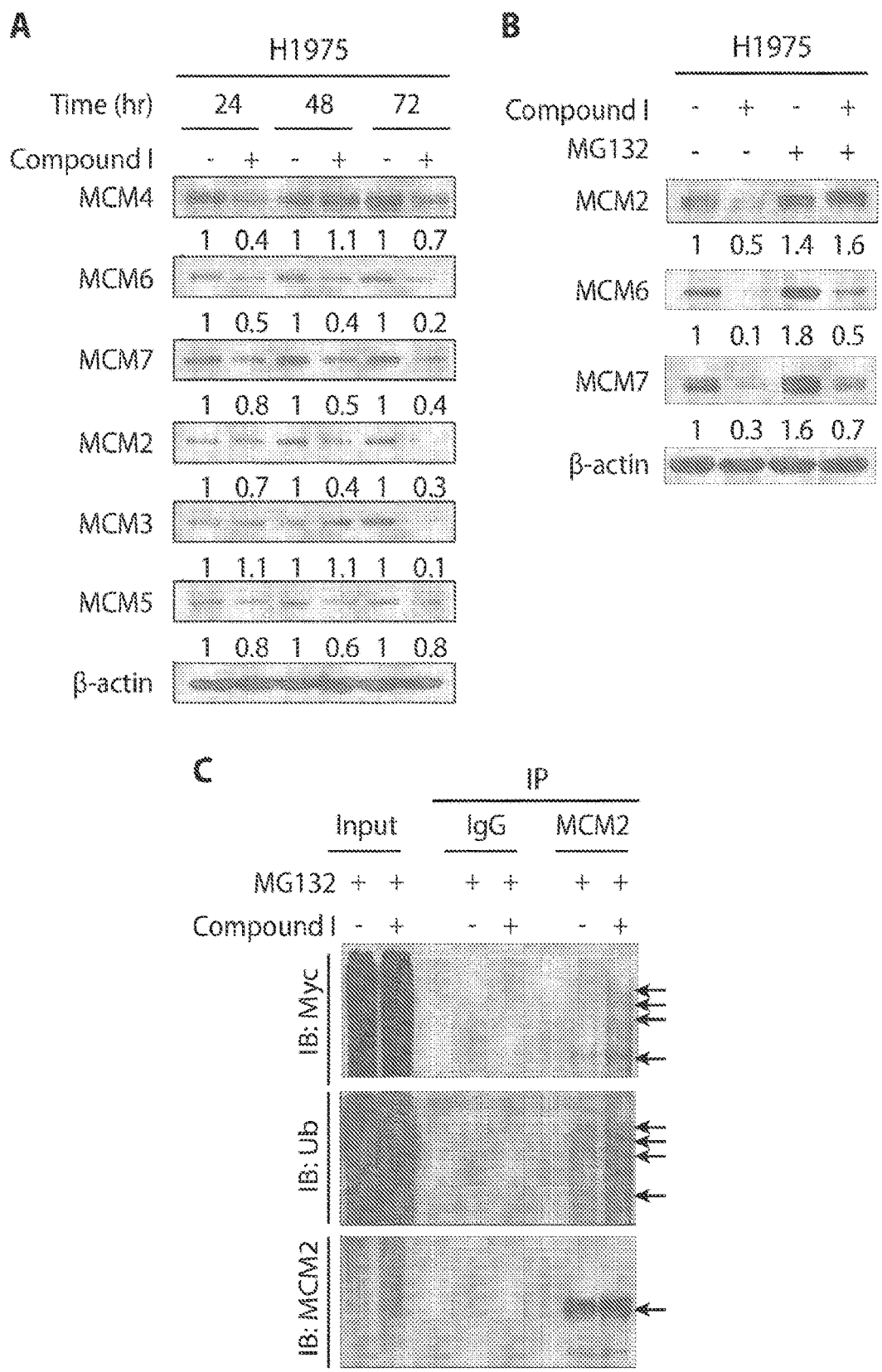
FIG. 3 shows exemplary results for compound 1-induced proteasome degradation through ubiquitination of MCM2. Panel (A): Immunoblot showing that MCM2/6/7 underwent major protein degradation upon treatment, and each of MCM2, MCM3, MCM4, MCM5, MCM6 and MCM7, showed protein degration by 72 hours. Panel (B): Immunoblot showing that the MG132 proteasome inhibitor may reverse the compound 1 effects on the MCM2/6/7 protein expression levels. Panel (C): Immunoblot showing exemplary results for compound 1-induced ubiquitinated-MCM2 formation. Panel (D): Immunoblot showing the chromatin-bound form of MCM2 was decreased by compound 1 treatment. A double thymidine block was performed and the data were collected at the indicated time points. Compared to DMSO, compound 1-treated H1975 cells decreased more MCM2 bound to DNA. Panel (E): A chart (top) and Immunoblot (bottom) showing cell survival was decreased after MCM2 knockdown.
Figure 3:
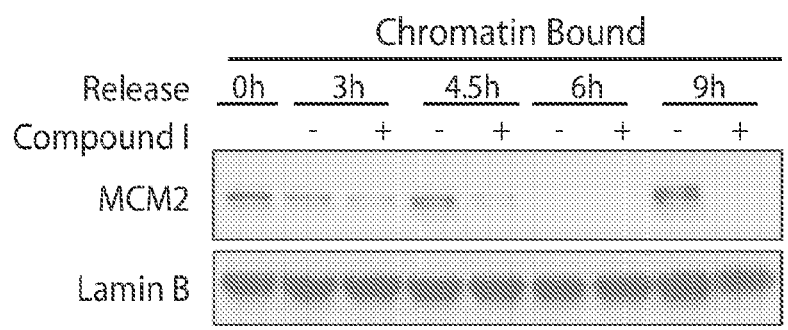
Figure 3:
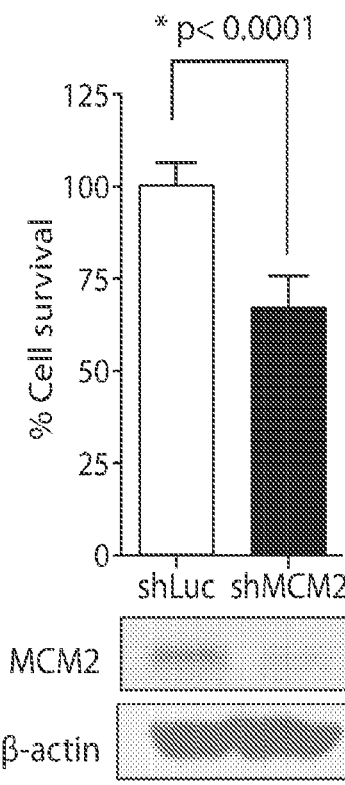

H1975 cell lysates was performed. Exemplary results are shown in Panels (A)-(C) of FIG. 3. H1975 cell were treated with DMSO and compound 1 (140 nM). Compound 1-treated H1975 cells were harvested at 24 hours, 48 hours, and 72 hours, and the protein expression levels of MCM complex were analyzed by immunoblotting. The expression levels of MCM2, MCM6, and MCM7 significantly decreased in both the 24 hour and 72 hour treated groups, but the expression of MCM3, MCM4, or MCM5 was lower only at 72 hours of compound 1 treatment. (Panel (A) of FIG. 3.).

To evaluate the effects of Compound 1 on triggering MCM2, MCM6, and MCM7 degradation through transcriptional or post-translational regulation, compound 1-treated H1975 cells were harvested at 48 hours with or without 10 µM MG132 treatment for 12 hours; and the protein expression levels of MCM2/6/7 were examined by immunoblotting. After treating H1975 cells with DMSO or compound 1 for 24 hours, it was observed that compound 1 induced a substantial decrease in MCM protein levels without a change in their messenger RNA levels, and this phenomenon was markedly reversed in the presence of the proteasome inhibitor MG132, especially in MCM2 expression (Panel (B) of FIG. 3). It was observed that MG132 proteasome inhibitor may reverse the compound 1 effects on MCM2/6/7 protein expression levels.

To determine whether Compound 1 triggers MCM2 degradation through promoting MCM2 ubiquitination, Myc-tagged ubiquitin (Myc-Ub) was transfected into H1975 cells treated with or without compound 1 and followed by MCM2 immunoprecipitation. The cells were transiently transfected with pcDNA3-Myc-Ub and treated with or without 140 nM of compound 1 combined with MG132. After 12 hours, the cells were harvested and MCM2 proteins were precipitated with specific anti-MCM2 antibodies. The ubiqiuitination pattern were detected by immunoblotting. IgG served as the antibody control in the immunoprecipitation experiment. Ubiquitylated MCM2 was detected in treated cells co-expressing Myc-Ub, and the ubiquitination extent was increased in the presence of MG132 (Panel (C) of FIG. 3). The results indicate that compound 1 may induce MCM degradation through the proteasome.

(V) Effects on DNA Binding Ability of MCM2 by Exemplary Compounds Described Herein To explore whether Compound 1-induced protein degradation also interfered with the DNA binding ability of MCM2, H1975 cells were synchronized using a double thymidine block followed by release with DMSO or compound 1 treatment for 3 to 9 hours. Exemplary results are shown in Panel (D) of FIG. 3. Then, the cells were harvested to obtain the chromatin-bound fraction, and MCM2 was detected by immunoblotting. The results showed that the chromatin-bound form of MCM2 was significantly reduced by compound 1 treatment compared to the DMSO control at 4.5 hour, 6 hour and 9 hour treatment groups (Panel (D) of FIG. 3), suggesting that compound 1 may target the MCM2 and interfere with its DNA binding activity in cells.

To determine whether manipulation of MCM2 expression can induce cell apoptosis, lentivirus-based short hairpin RNAs (shRNAs) were used to silence the expression levels of MCM2 in H1975 cell lines, and the effects on cell growth were examined. Exemplary results are shown in Panel (E) of FIG. 3. The cells were infected with the indicated lentivirus in media containing polybrene (8 mg/ml). 24 h post-infection, the cells were treated with fresh medium for 48 hours, and analyzed by western blotting and SRB for an additional 72 hours. The utilized lentiviruses were generated by co-transfection of HEK293T cells with the lentiviral vector pLKO. 1-shMCM2 from the National RNAi Core Facility (Academia Sinica, Taiwan) and two helper plasmids (pCMVΔR8.91, pMD.G) using Lipofectamine 2000 (Invitrogen). The virus-containing medium was collected at 24, 48, or 72 hours post-transfection, centrifuged, and filtered through 0.45 mm-pore-size filters. The cells were infected with the indicated lentivirus in media containing polybrene (8 mg/ml). Twenty-four hours after infection, the cells were treated with fresh medium for 48 hours and used for other experiments. Knocking down the expression of MCM2 was associated with a 33% inhibition of cell growth (p<0.0001, Panel (E) of FIG. 3); and the inhibition effects also showed a dose dependent manner of MCM2 depletion (p<0.0001). Collectively, these findings suggest that Compound 1 may target MCM2, induce its protein degradation and contribute to cell apoptosis in lung cancer cells.

(VI) Target Identification Experiments of Exemplary Compounds Described Herein

Figure 4:
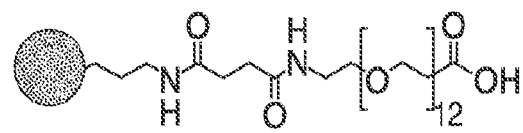
FIG. 4 shows preliminary target identification experiments involving affinity-based pull downs for the binding of compound 1 to MCM2. Panel A: Structures of Mag-beads-control compound and Mag-beads-Compound 1. The Mag-beads-Compound 1 complex was formed by a method shown in Scheme 3 below. Panel B: A photo showing immunoprecipitation of MCM2 in the presence of the Congrol and Compound 1. Panel C: A schematic illustration of functional domains of MCM2. Panel D: diagrams showing the structure of the complex formed by MCM2 and Compound 1. Panel E: A diagram showing the complex formed by Compound 1 and a MCM hexamer. Panel F: A diagram showing the binding pocket of Compound 1 in MCM2 ad predicted by computational analysis. Panel G: A diagram showing that Compound 1 has a higher binding activit to wild-type MCM2 as compared with MCM2 Q341A mutant, as determined by an immunoprecipitation assay.
Figure 4:
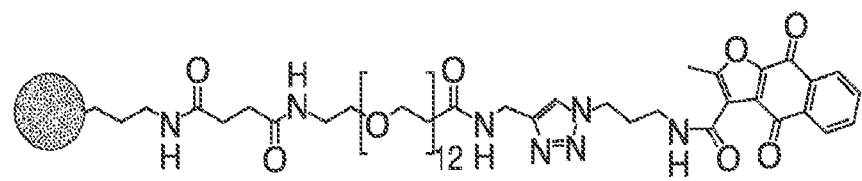
Figure 4:
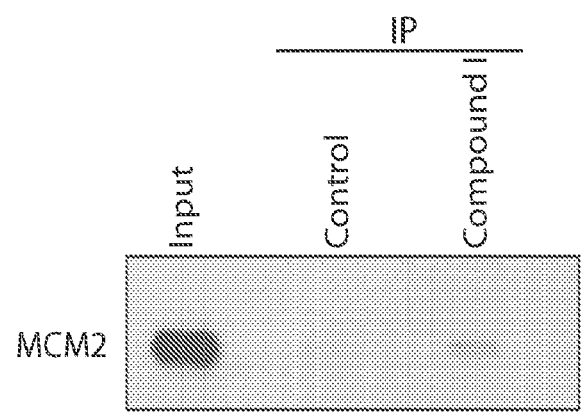
Figure 4:
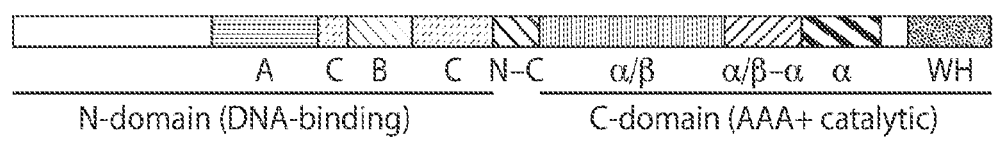
Figure 4:
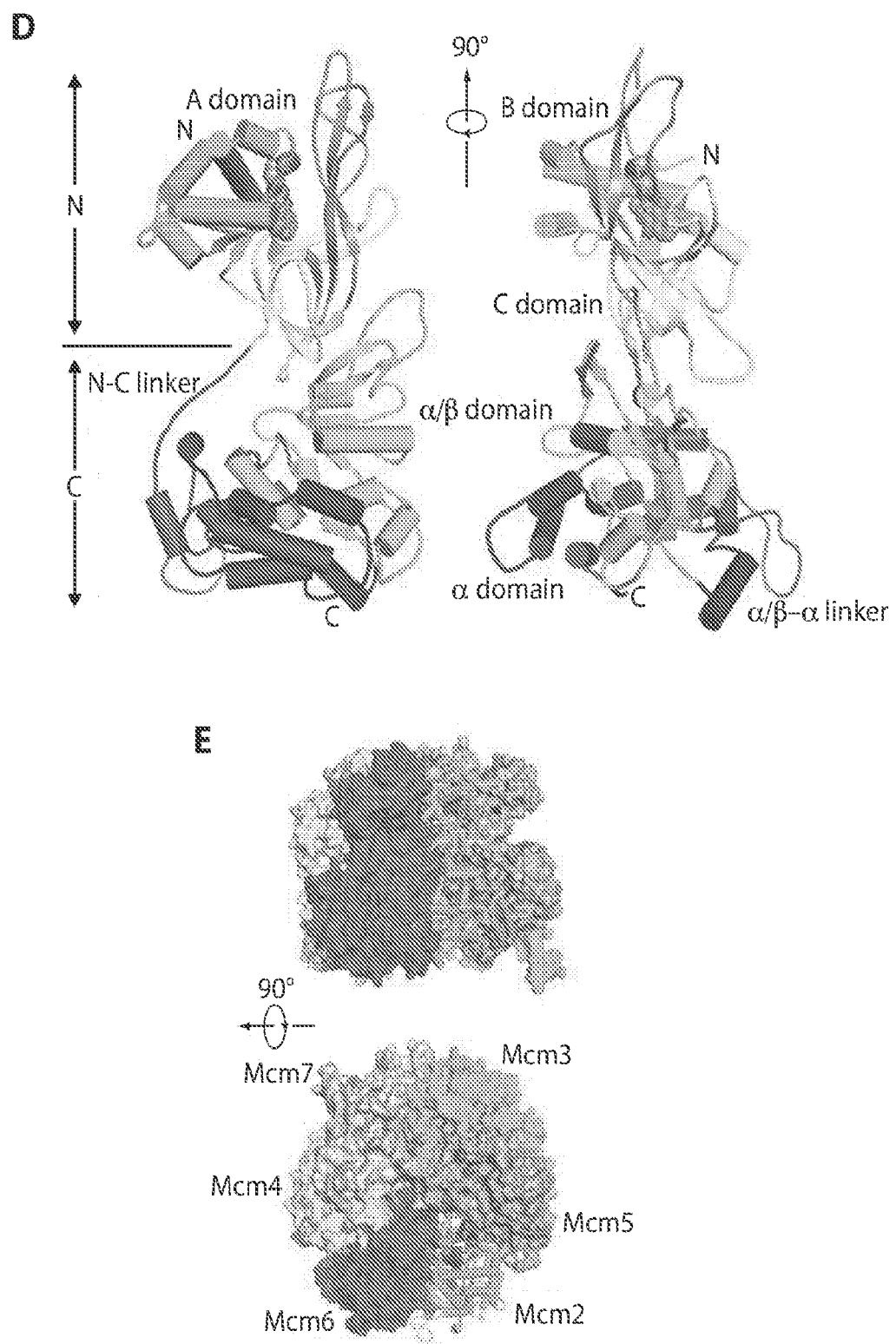
Figure 4:
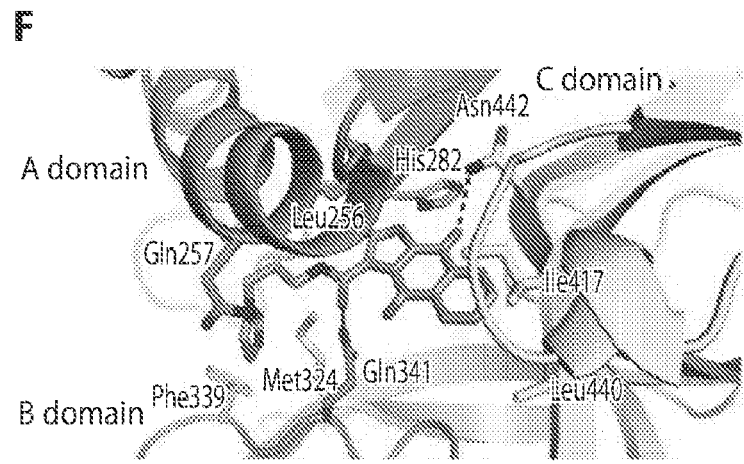
Figure 4:
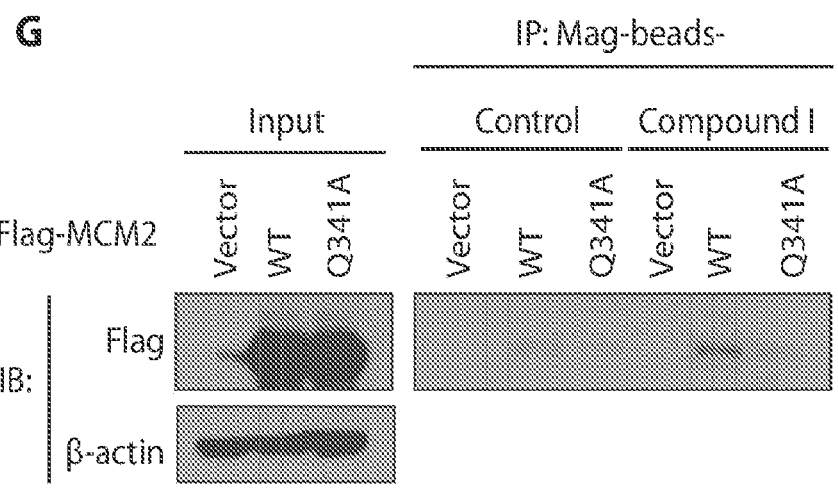

To explore the mechanism of action of Compound 1, preliminary target identification experiments involving affinity-based pull downs were carried out. Panel (A) of FIG. 4 shows the structure of Mag-beads-Control and Mag-beads-compound 1. The MCM2 proteins were pulled down by incubating the H1975 lysate with compound 1-conjugated magnetic beads (Panel (A) of FIG. 4) for 24 hours at 4° C.; and the precipitated MCM2 proteins were detected by immunoblotting. To synthesize the Mag-beads-compound 1 complex, Scheme 3 was followed.

Scheme 3. Conjugation of Compound 1 onto magnetic beads.

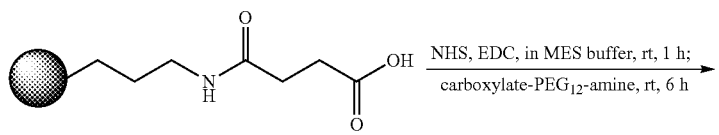

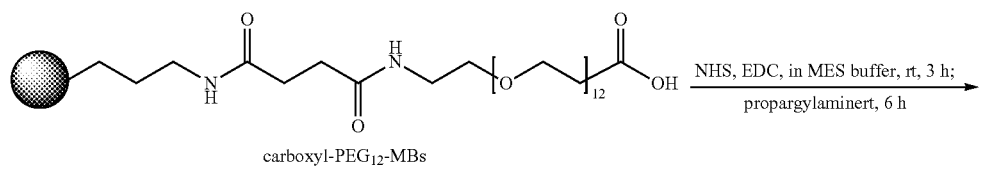

carboxyl-PEG$_{12}$-MBs

-continued

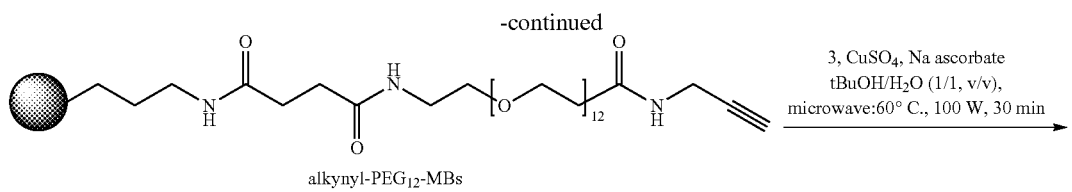

alkynyl-PEG$_{12}$-MBs

3, CuSO$_4$, Na ascorbate
tBuOH/H$_2$O (1/1, v/v),
microwave: 60° C., 100 W, 30 min

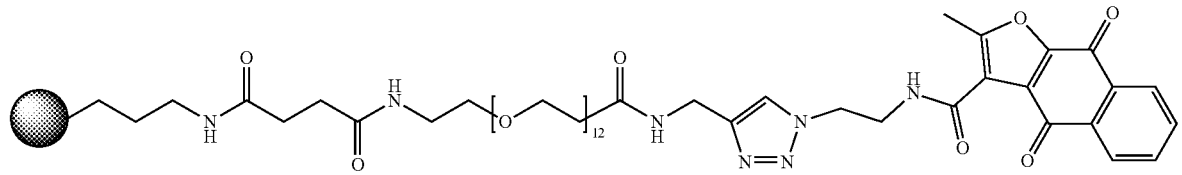

In Scheme 3, a polyethylene glycol (PEG) reagent (carboxylate-PEG12-amine) was attached to beads to reduce nonspecific binding on the bead surface. Next, the carboxylic acid end of the tentacle was coupled with propargylamine to give alkynyl-PEG12-MBs, which was then conjugated with N-(2-Azidoethyl)-2-methyl-4, 9-dioxo-4, 9-dihydronaphtho [2, 3-b]furan-3-carboxamide by Cu catalyzed Click reaction.

Carboxyl-PEG$_{12}$-MBs57

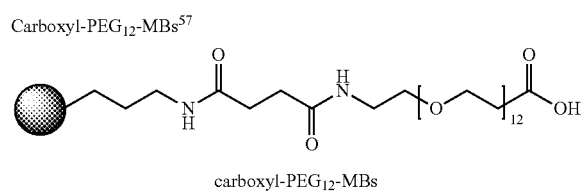

carboxyl-PEG$_{12}$-MBs

Carboxylate magnetic beads (10 mg) were dispersed into MES (50 mM, pH 6.0, 300 µL). N-hydroxysuccinimide (NHS, 3.5 mg, 0.03 mmol) and 1-ethyl-3-(3-dimethylaminopropyl)carbodiimide hydrochloride (EDC.HCl, 5.7 mg, 0.03 mmol) were added to the solution and stirred for 1 hr at room temperature. The resulting beads were washed with PBS (50 mM, pH 7.0, 300 µL×2) to remove excess NHS and EDC.HCl. 200 µL of 1 mM carboxylated-PEG$_{12}$-amine (pH 7.8 in 50 mM HEPES) was added to the beads and then stirred for 6 hr at room temperature. After separation with a magnet, the beads were washed with MES (50 mM, pH 6.0) to give carboxyl-PEG$_{12}$-MBs.

Exemplary syntheses of carboxylate magnetic beads, as depicted in Scheme 3 above, are also described in Hung et al, *J. Am. Chem. Soc.*, 135(16): 5934-5937.

Alkynyl-PEG$_{12}$-MBs

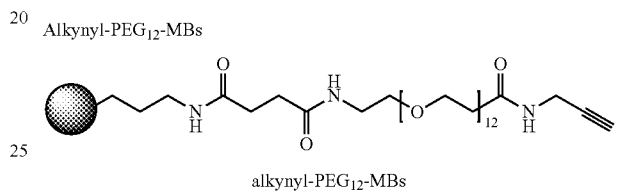

alkynyl-PEG$_{12}$-MBs

Carboxyl-PEG$_{12}$-MBs (10 mg) were dispersed into MES (50 mM, pH 6.0, 300 µL). N-hydroxysuccinimide (NHS, 3.5 mg, 0.03 mmol) and 1-ethyl-3-(3-dimethylaminopropyl)carbodiimide hydrochloride (EDC.HCl, 5.7 mg, 0.03 mmol) were added to the solution and stirred for 3 hr at room temperature. The resulting beads were washed with PBS (50 mM, pH 7.0, 300 µL×2) to remove excess NHS and EDC.HCl. 200 µL of 1 mM propargylamine (pH 7.0 in 50 mM PBS) was added to the beads and then stirred for 6 hr at room temperature. After separation with a magnet, the beads were washed with MES (50 mM, pH 6.0) to give alkynyl-PEG$_{12}$-MBs.

Mag-beads-compound 1

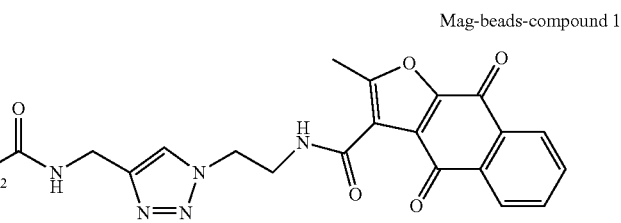

To a solution of alkynyl-PEG$_{12}$-MBs (10 mg), azide 3 (1.3 mg, 4.0 µmol), CuSO$_4$ in 0.1 M H$_2$O (5 µL, 0.5 µmol) and sodium ascorbate in 0.1 M H$_2$O (2 µL, 0.2 µmol) was in t-Butanol/H$_2$O (0.2 mL, 1/1, v/v) and in Microwave condition: 100 W, 60° C. for 30 min. After separation with a magnet, the beads were washed with MES (50 mM, pH 6.0) to give the Mag-beads-compound 1 complex.

Returning to FIG. 4, the results showed that the expression of precipitated MCM2 could only be found in the mag-beads-compound 1 pulled down group but not in the mag-beads-control group (Panel (B) of FIG. 4). Panel (B) of FIG. 4 shows the ability of compound 1 to bind to MCM2. H1975 cell lysates were incubated with magnetic beads- Control or compound 1 overnight; and the existence of precipitated MCM2 proteins were detected by immunoblotting.

In FIG. 4, panels (C) and (D) show the protein-ligand docking program iGEMDOCK prediction that the binding pocket of compound 1 is located at the N-terminal domain of MCM2. This is a cavity surrounded by domains A, B and C. (Panels (C) and (D) of FIG. 4). Panel (C) of FIG. 4 shows the Domain organization of MCM2 (N—C, N to C linker; α/β, α/β domain of AAA$^+$ ATPase core structure; α/β-α, linker between subdomains in the ATPase core; a, a domain; WH, winged-helix domain). The domain annotation is based on the structure of ssoMCM. Laskowski, et al, *J. Appl. Cryst.*, 26(2):283-291. Panel (D) of FIG. 4 shows MCM2 complexed with compound 1. Domains and linkers are colored as in C and D. Helices are depicted as cylinders and β-strands as arrows. Compound 1 is shown as spheres (pink, carbon; blue, nitrogen; red, oxygen). FIG. 4E shows compound 1 in a MCM hexamer. In Panel (E) of FIG. 4, the mouth of the binding pocket of compound 1 is close to the interface between MCM2 and MCM6 in a MCM hexamer. The B domain of MCM6 may rotate and insert into this pocket to increase the interaction with MCM2. Protomers (MCM2-7) are as labeled. Compound 1 is shown as red spheres in the MCM hexamer.

Panel (F) of FIG. 4 shows the compound 1 binding pocket. AutoDock Vina (Trott, et al, *J. Comput. Chem.*, 31(2):455-461) predicted a binding mode of compound 1 with a binding energy of −8.8 kcal/mol. (Panel (F) of FIG. 4). Hsu, et al, *BMC Bioinformatics*, 12 Suppl 1: S33. In this binding mode, it was observed that residues from the three domains including His282 and Gln257 in domain A, Gln341 in domain B and Asn442 in domain C are involved in interaction with compound 1. In particular, Gln341 in domain B contributes much more to the intermolecular hydrogen bond formation. The domains are colored as in D. The residues involved in compound 1 binding are shown as stick models. The black dashed lines represent the polar contacts between amino acid residues and compound 1. Panel (G) of FIG. 4 shows Mag-beads-compound 1 pulled down less MCM2 Q341A than MCM2 wild type. Immunoprecipitation was performed by the incubation of overexpressed FLAG, FLAG-MCM2 wild type or Q341A mutant lysate with magnetic bead control or mag-beads-compound 1.

The results of the biological experiments suggest that compound 1, may target to the N-terminus of MCM2 and may contribute to the induction of ubiquitinated-MCM2 through proteasome degradation. The MCM2 degradation may further interfere the formation of MCM complex, cause inhibition of DNA replication and prolong the duration of S phase in cancer cell proliferation; may promote cell apoptosis in vitro; and may inhibit tumor growth in vivo.

Example 3: Anti-Bacterial Activity of Compound I Against MRSA

Figure 5:
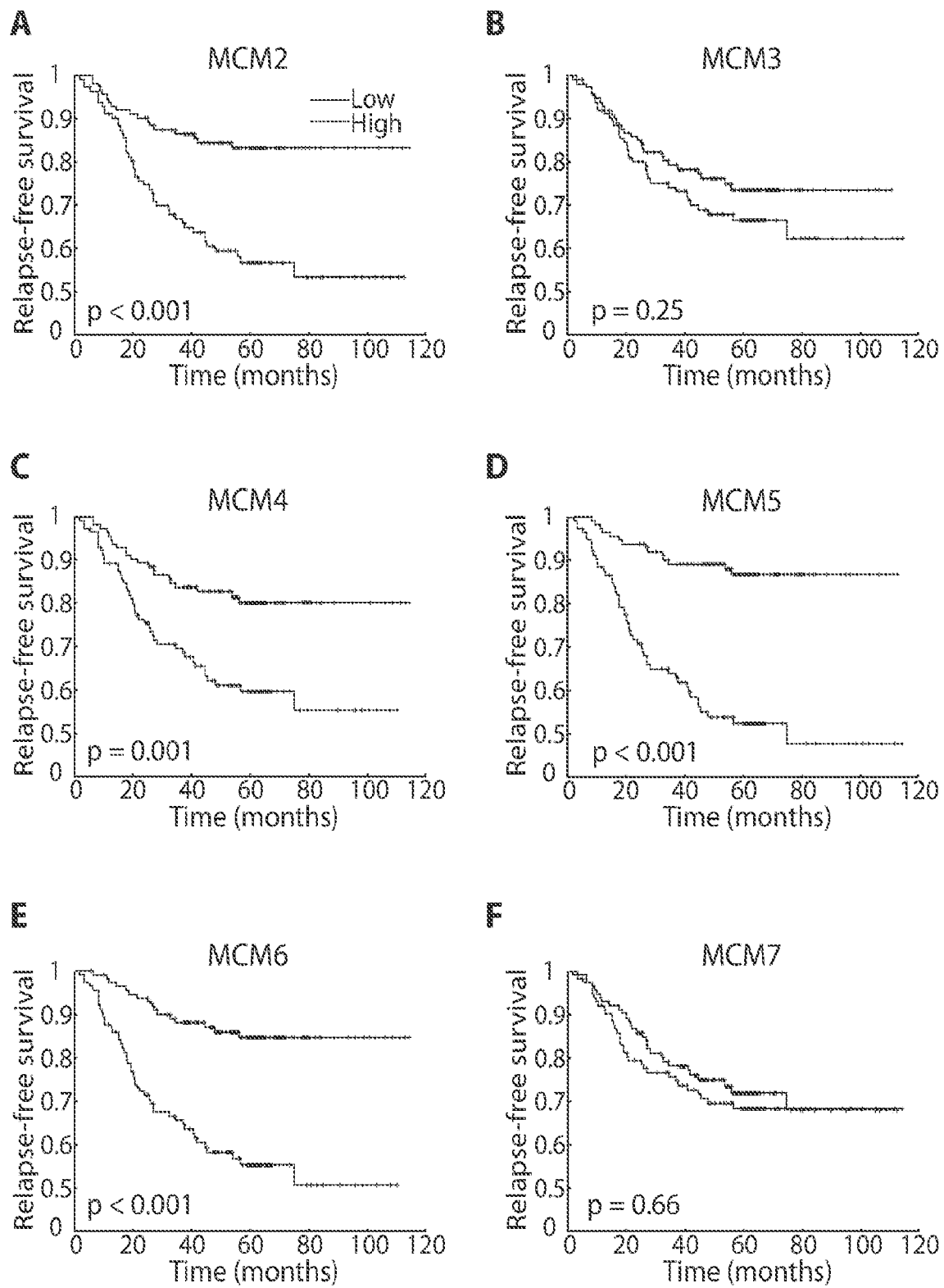
FIG. 5 includes charts showing Kaplan-Meier analysis of overall survival for 226 pathological stage I-II lung adenocarcinomas published as GSE31210. Panels (A)-(F): charts showing the clinical significance and prognostic value of MCM in non small cell lung cancer. Panel (G): graphic showing action pathways for Compound 1-induced apoptosis.
Figure 5:
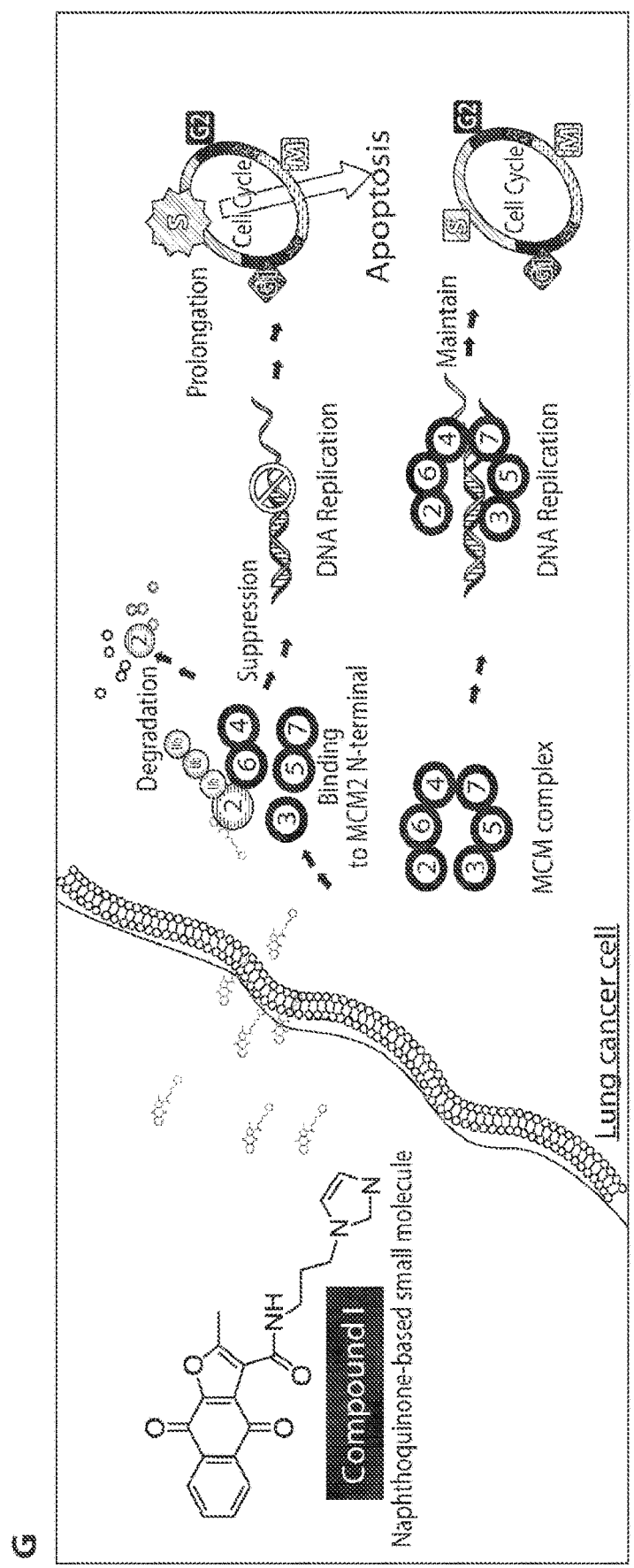
Figure 6:
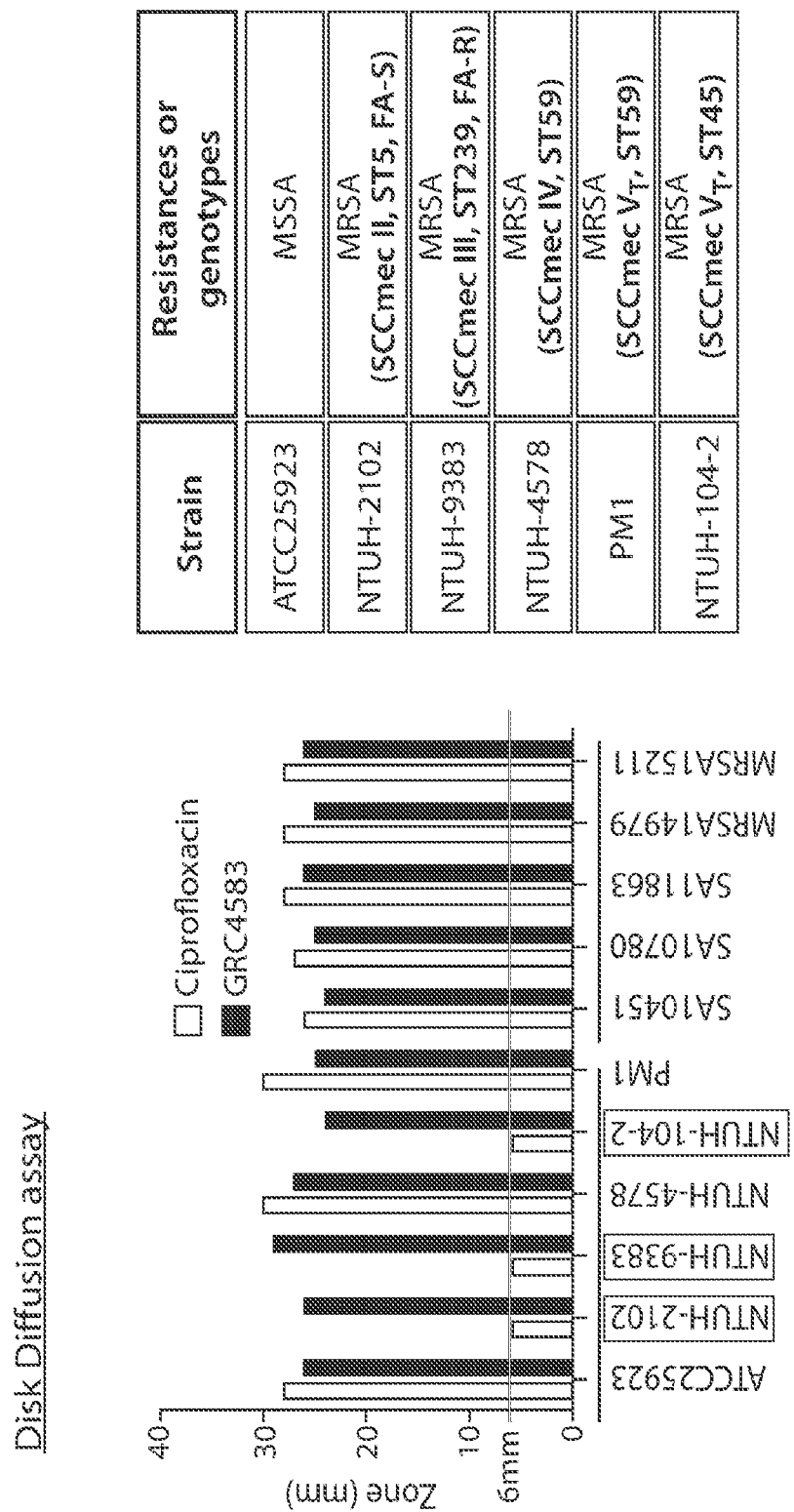
FIG. 6 shows the antibacterial activity of Compound 1 determined by disc diffusion assay.
Figure 7:
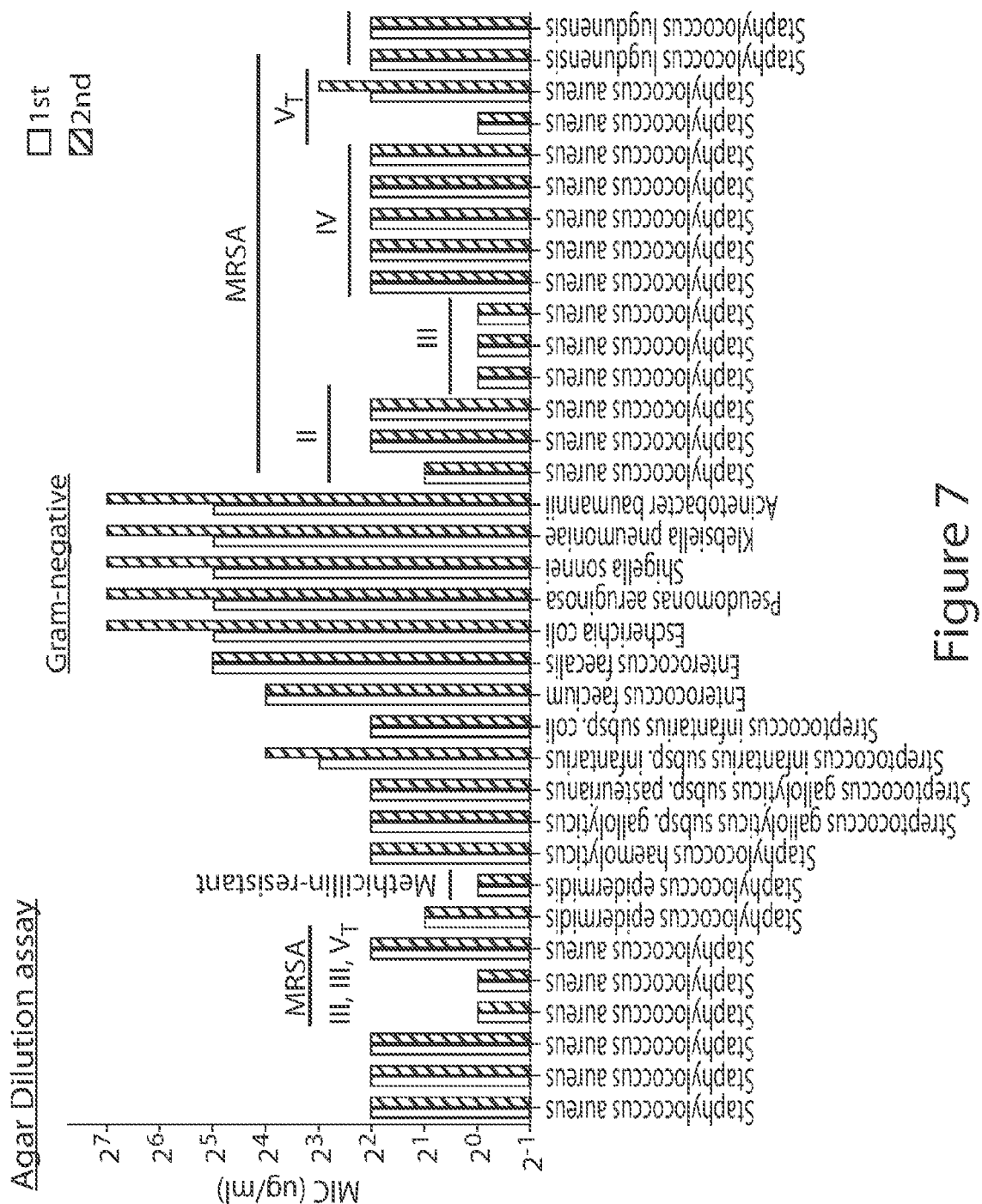
FIG. 7 is a chart showing the MIC of Compound 1 as determined by the broth micro dilution method described herein.

To investigate the antibacterial activity of Compound 1 against methicillin resistant *Staphylococcus aureus* (MRSA), a panel of clinical bacterial strains including 15 *Staphylococcus*, 4 *Streptococcus*, 2 *Enterococcus*, 5 gram negative and 15 clinical isolate strains were used to evaluate the antimicrobial efficacy by the disc diffusion method via determination of the surrounding inhibition zones, as well as by evaluating the MIC using the broth micro dilution method. In disk diffusion test, compound land well known anti-bacterial drug, ciprofloxacin were dissolved in DMSO and 10 µl was added to sterile 6 mm diameter paper disk. Bacteria were grown in Mueller Hinton agar (Difco) for 18 h at 37° C. in an incubator. After incubation, inhibition zones were visually measured along the edge of the disks and the plates were photographed. Compound 1 showed antimicrobial activity against all the MRSA strains at 5 µg concentration as determined by disc diffusion method, especially three of the tested bacteria strains are ciprofloxacin resistant strains (FIG. 5, the average diameter of the inhibition zone is 25.5 mm). Similarly, the MIC for Compound 1 ranged from 1 to 4 µg/mL (FIG. 6). See also Table 4 and Table 5 below:

TABLE 4

Qualitative antibacterial activity of 5 µg Ciprofloxacin and Compound 1

| | Inhibition zone (mm) | | |
|---|---|---|---|
| Strain | Ciprofloxacin | Compound 1 | Resistances or genotypes |
| ATCC25923 | 28 | 26 | MSSA |
| NTUH-2102 | 6 | 26 | MRSA (SCCmec II, ST5, FA-S) |
| NTUH-9383 | 6 | 29 | MRSA (SCCmec III, ST239, FA-R) |
| NTUH-4578 | 30 | 27 | MRSA (SCCmec IV, ST59) |
| PM1 | 30, 23 | 25 | MRSA (SCCmec $V_T$, ST59) |
| NTUH-104-2 | 6 | 24 | MRSA (SCCmec $V_T$, ST45) |
| SA10451 | 26 | 24 | |
| SA10780 | 27 | 25 | |
| SA11863 | 28 | 25 | |
| MRSA14979 | 28 | 25 | |
| MRSA15211 | 28 | 26 | |

TABLE 5

Quantitative Antibacterial activity of compound 1 by MIC determination assays

| | | | MIC (µg/ml) Compound I | | | |
|---|---|---|---|---|---|---|
| No. | Species | Strain | 100% | 50% | Resistances or genotypes | Source |
| 1 | Staphylococcus aureus | ATCC29213 | 4 | 1 | MSSA | |
| 2 | Staphylococcus aureus | ATCC12598 | 4 | 0.5 | MSSA | |
| 3 | Staphylococcus aureus | ATCC25923 | 4 | 2 | MSSA | |
| 4 | Staphylococcus aureus | ATCC33592 | 1 | 0.5 | MRSA (SCCmec III) | |
| 5 | Staphylococcus aureus | ATCC49476 | 1 | 0.5 | MRSA (SCCmec III) | |
| 6 | Staphylococcus aureus | TSHR17 | 4 | 0.5 | MRSA (SCCmec $V_T$) | |

TABLE 5-continued

Quantitative Antibacterial activity of compound 1 by MIC determination assays

| No. | Species | Strain | MIC (µg/ml) Compound I 100% | MIC (µg/ml) Compound I 50% | Resistances or genotypes | Source |
|---|---|---|---|---|---|---|
| 7 | Staphylococcus epidermidis | ATCC12228 | 2 | 0.5 | methicillin-susceptible | |
| 8 | Staphylococcus epidermidis | ATCC35984 | 1 | 0.25 | methicillin-resistant | |
| 9 | Staphylococcus haemolyticus | ATCC29970 | 4 | 2 | methicillin-susceptible | |
| 10 | Streptococcus gallolyticus subsp. gallolyticus | ATCC43143 | 4 | 2 | | S. bovis |
| 11 | Streptococcus gallolyticus subsp. pasteurianus | ATCC43144 | 4 | 2 | | S. bovis |
| 12 | Streptococcus infantarius subsp. infantarius | ATCC BAA-102 | 8 | 4 | | S. bovis |
| 13 | Streptococcus infantarius subsp. coli | ATCC BAA-103 | 4 | 2 | | S. bovis |
| 14 | Enterococcus faecium | ATCC19434 | 16 | 2 | | |
| 15 | Enterococcus faecalis | ATCC19433 | 32 | 16 | | |
| 17 | Escherichia coli | ATCC33625 | >32 | >32 | | gram negative |
| 18 | Pseudomonas aeruginosa | ATCC27853 | >32 | >32 | | gram negative |
| 19 | Shigella sonnei | ATCC9290 | >32 | >32 | | gram negative |
| 20 | Klebsiella pneumoniae | ATCC700603 | >32 | >32 | | gram negative |
| 21 | Acinetobacter baumannii | ATCC19606 | >32 | >32 | | gram negative |
| 22 | Staphylococcus aureus | NTUH-4400 | 2 | 1 | MRSA (SCCmec II, ST5, FA-R) | clinical isolate |
| 23 | Staphylococcus aureus | NTUH-2102 | 4 | 1 | MRSA (SCCmec II, ST5, FA-S) | clinical isolate |
| 24 | Staphylococcus aureus | NTUH-560 | 4 | 1 | MRSA (SCCmec II, GM-S) | clinical isolate |
| 25 | Staphylococcus aureus | NTUH-9383 | 1 | 0.5 | MRSA (SCCmec III, ST239, FA-R) | clinical isolate |
| 26 | Staphylococcus aureus | NTUH-2417 | 1 | 0.5 | MRSA (SCCmec III, SXT-S) | clinical isolate |
| 27 | Staphylococcus aureus | NTUH-1-2868 | 1 | 0.5 | MRSA (SCCmec III, ST239, FA-R) | clinical isolate |
| 28 | Staphylococcus aureus | NTUH-4578 | 4 | 1 | MRSA (SCCmec IV, ST59) | clinical isolate |
| 29 | Staphylococcus aureus | NTUH-406-2 | 4 | 0.5 | MRSA (SCCmec IV, spa type t008) | clinical isolate |
| 30 | Staphylococcus aureus | NTUH-2643 | 4 | 1 | MRSA (SCCmec IV, spa type t015) | clinical isolate |
| 31 | Staphylococcus aureus | NTUH-8038 | 4 | 1 | MRSA (SCCmec IV, spa type t189) | clinical isolate |
| 32 | Staphylococcus aureus | PM1 | 4 | 1 | MRSA (SCCmec $V_T$, ST59) | clinical isolate |
| 33 | Staphylococcus aureus | NTUH-104-2 | 1 | 0.5 | MRSA (SCCmec $V_T$, ST45) | clinical isolate |
| 34 | Staphylococcus aureus | NTUH-2967 | 4 | 1 | MRSA (SCCmec $V_T$, ST1) | clinical isolate |
| 35 | Staphylococcus lugdunensis | NTUH-4179 | 4 | 0.5 | methicillin-resistant | clinical isolate |
| 36 | Staphylococcus lugdunensis | NTUH-6767 | 4 | 0.5 | methicillin-resistant | clinical isolate |

Thus, results of this study demonstrated that GRC4583 (Compound 1) showed stronger antibacterial activity against MRSA as compared to ciprofloxacin.

Example 4: Anti-Cancer and Anti-Bacterial Activity of Compound I and Analogues Thereof Compound 1 and its analogues shown in Table 6 below were tested for their activities on cancer cells and bacterial cells using assays described herein. H1975, MDA-MB231, and MCF7 cells were incubated in the presence of the compounds in cell growth medium containing 10% fetal bovine serum for two days in a mammalian cell culture incubatoe. Cell viability were monitored by using Cell-TiterGlo. Staphylococcus aureus and Escherichia coli were incubated in the presence of the compounds in Muller-Hinton broth for 16-24 hours in a 37° C. incubator. Bacterial growth was monitored by using Alamar Blue (Invitrogen).

The results are provided in Table 7.

TABLE 6

Structures of Compound 1 Analogues

| Compound Name | Structure |
|---|---|
| 00056034583 (compound 1) 00055727872 | 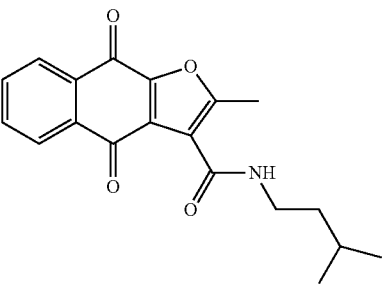 [SMILES: Cc1oc2c(c1C(=O)NCCC(C)C)C(=O)c1ccccc1C2=O] |
| 00053891400 | 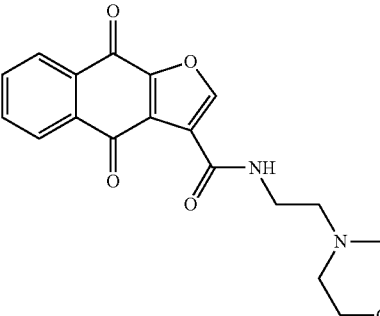 |
| 00056034607 | 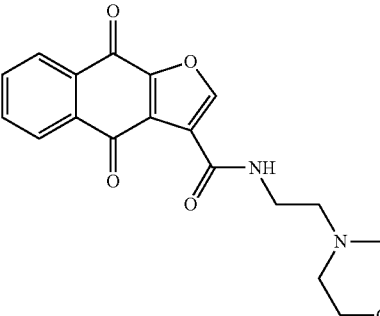 |

TABLE 6-continued

Structures of Compound 1 Analogues

| Compound Name | Structure |
|---|---|
| 00054506228 | 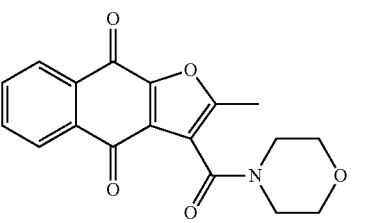 [SMILES: Cc1oc2c(c1C(=O)N1CCOCC1)C(=O)c1ccccc1C2=O] |
| 00055422996 | 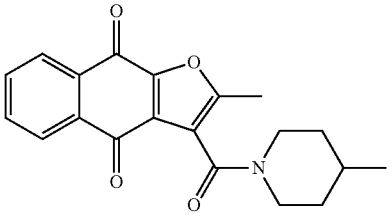 [SMILES: Cc1oc2c(c1C(=O)N1CCC(C)CC1)C(=O)c1ccccc1C2=O] |
| 00055422098 | 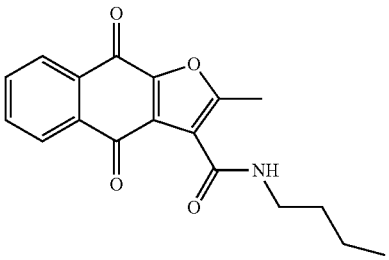 [SMILES: CCCCNC(=O)c1c(C)oc2c1C(=O)c1ccccc1C2=O] |
| 00054811255 | 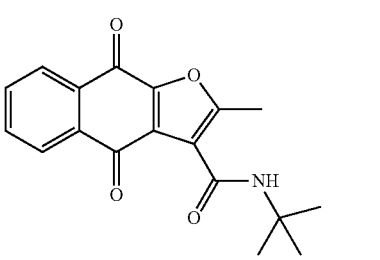 [SMILES: Cc1oc2c(c1C(=O)NC(C)(C)C)C(=O)c1ccccc1C2=O] |

TABLE 7

Anti-Cancer and Anti-Bacterial Activities of Compound 1 and Analogues Thereof

| | % of the activities in the presence of ~10 μM compound | | | | |
|---|---|---|---|---|---|
| Compounds | Lung Cancer Cells (H1975) | Breast Cancer Cells (MDA-MB231) | Breast Cancer Cells (MCF) | *Staphylococcus aureus* | *Escherichia coli* |
| 00056034583 (compound 1) | 4.2% | 13.7% | 6.0% | 38.1% (MIC = 2 μg/ml) | >100% |
| 00055727872 | 4.2% | 72.0% | 44.3% | >100% | >100% |
| 00053891400 | 4.0% | 12.2% | 6.1% | >100% | >100% |
| 00056034607 | 4.4% | 61.2% | 12.9% | 75.8% | >100% |
| 00054506228 | 4.6% | 54.4% | 13.6% | 65.4% | >100% |
| 00055422996 | 4.3% | 20.9% | 6.9% | >100% | >100% |
| 00055422098 | 3.7% | 69.8% | 35.0% | >100% | >100% |
| 00054811255 | 4.2% | 13.4% | 6.5% | >100% | >100% |

Example 5: Anti-Tumor Efficacy of Exemplary Compounds

Figure 8:
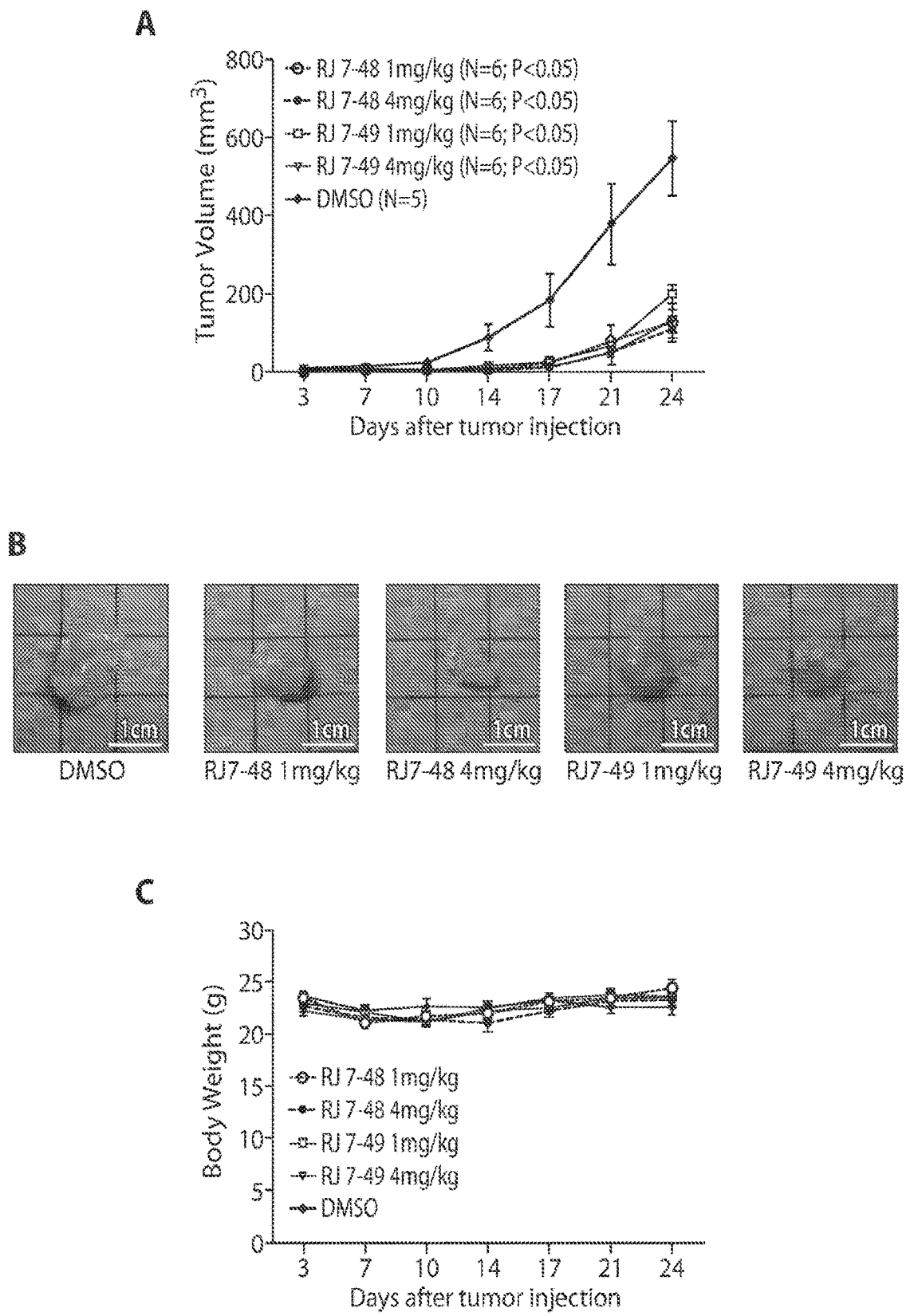
FIG. 8 shows the in vivo antitumor effects of treatment of athymic nude mice that bear established subcutaneous H1975 tumors with compounds 48 and 49 (RJ7-48 or RJ7-49), including marked reduction of the H1975 xenograft tumor growth compared with the control group. Panel (A): A chart showing the mean±SEM tumor volumes of mice in the treatment and vehicle groups on the days of pretreatment. The tumor size was measured with a caliper rule every time before compound delivery. Panel (B): Photos showing the representative tumor images taken from mice treated for 24 days with DMSO or exemplary compounds 48 and 49. Panel (C): A chart showing the body weight of each tested mice were measured and presented on the indicated day after tumor cells injection. H1975 cells were injected subcutaneously into the right flank region of nude mice. Three days after the injection, the mice were daily treated with vehicle (DMSO) or compound 48 or compound 49 at 1 mg/kg or 4 mg/kg intraperitoneally for 24 days. Exemplary compounds 48 and 49 inhibit H1975 lung cancer cell growth in vivo.

Exemplary compounds 48 and 49 were tested for their in vivo effect on tumor growth by measuring H1975 tumor growth following treatment of compounds 48 and 49. To explore the in vivo antitumor efficacy of exemplary compounds 48 and 49, athymic nude mice that bear established subcutaneous H1975 tumors were treated daily intraperitoneally with compounds 48 or 49 at 1 mg/kg or 4 mg/kg versus DMSO control for 4 weeks (n=6 for each group). Results of the in vivo anti-tumor effects of exemplary compounds 48 and 49 are shown in FIG. 8 (See FIG. 8, Panels (A)-(C)).

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound selected from the group consisting of

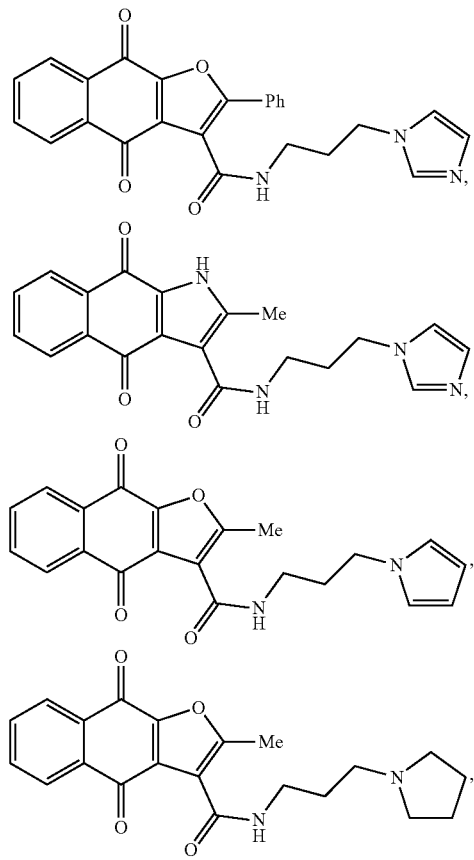

or a pharmaceutically acceptable salt thereof.

2. A pharmaceutical composition comprising a compound of claim 1, or a pharmaceutically acceptable salt thereof, and a pharmaceutically acceptable excipient.

3. A compound having the following formula:
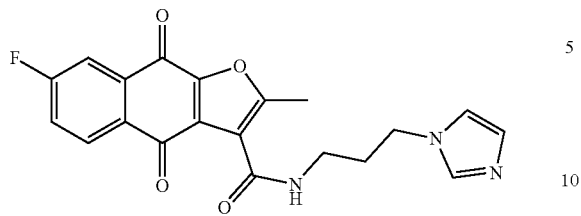
or a pharmaceutically acceptable salt thereof.
* * * * *